(12) United States Patent
Dienno et al.

(10) Patent No.: US 10,653,521 B2
(45) Date of Patent: *May 19, 2020

(54) PROSTHETIC VALVES WITH MECHANICALLY COUPLED LEAFLETS

(71) Applicant: W. L. Gore & Associates, Inc., Newark, DE (US)

(72) Inventors: Dustin V. Dienno, Flagstaff, AZ (US); Michael G. Dunham, Flagstaff, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 203 days.

This patent is subject to a terminal disclaimer.

(21) Appl. No.: 15/829,595

(22) Filed: Dec. 1, 2017

(65) Prior Publication Data

US 2018/0110619 A1    Apr. 26, 2018

Related U.S. Application Data

(63) Continuation of application No. 14/973,589, filed on Dec. 17, 2015, now Pat. No. 9,855,141.

(60) Provisional application No. 62/093,930, filed on Dec. 18, 2014.

(51) Int. Cl.
*A61F 2/24*    (2006.01)

(52) U.S. Cl.
CPC .......... *A61F 2/2418* (2013.01); *A61F 2/2412* (2013.01); *A61F 2/2415* (2013.01); *A61F 2210/0014* (2013.01); *A61F 2220/0033* (2013.01); *A61F 2220/0075* (2013.01); *A61F 2220/0083* (2013.01); *A61F 2230/0069* (2013.01); *A61F 2240/001* (2013.01)

(58) Field of Classification Search
CPC ................................. A61F 2/24; A61F 2/2418
USPC .................................................. 623/2.1–2.19
See application file for complete search history.

(56) References Cited

U.S. PATENT DOCUMENTS

| 5,163,955 A | 11/1992 | Love et al. |
| 5,708,044 A | 1/1998 | Branca |
| 6,334,873 B1 | 1/2002 | Lane et al. |
| 6,541,589 B1 | 4/2003 | Baillie |

(Continued)

FOREIGN PATENT DOCUMENTS

| JP | 2013-540467 | 11/2013 |
| WO | 00/18333 | 4/2000 |

(Continued)

OTHER PUBLICATIONS

International Search Report for PCT/US2015/066865 dated Mar. 22, 2016, corresponding to U.S. Appl. No. 14/973,515 and U.S. Appl. No. 14/973,589; 6 pages.

*Primary Examiner* — Suzette J Gherbi
(74) *Attorney, Agent, or Firm* — Paul J. Fordenbacher, Esq.

(57) ABSTRACT

Described embodiments are directed toward centrally-opening leaflet prosthetic valve devices having a leaflet frame and a mechanically coupled leaflet. The described leaflet frames have projections that are configured to couple with apertures located within the leaflet attachment region of a leaflet. Some embodiments are further directed toward pulmonary valved conduits incorporating such leaflet and leaflet frame constructs. Methods of making and using such prosthetic valve devices are also described amongst others.

40 Claims, 38 Drawing Sheets

(56) References Cited

U.S. PATENT DOCUMENTS

| | | | |
|---|---|---|---|
| 6,951,571 B1 * | 10/2005 | Srivastava | A61F 2/2418 623/1.24 |
| 7,306,729 B2 | 12/2007 | Bacino et al. | |
| 7,462,675 B2 | 12/2008 | Chang et al. | |
| 7,531,611 B2 | 5/2009 | Sabol et al. | |
| 8,409,274 B2 | 4/2013 | Li et al. | |
| 8,637,144 B2 | 1/2014 | Ford | |
| 8,801,779 B2 * | 8/2014 | Seguin | A61F 2/2418 623/2.1 |
| 8,961,599 B2 | 2/2015 | Bruchman et al. | |
| 8,992,608 B2 | 3/2015 | Haug et al. | |
| 9,139,669 B2 | 9/2015 | Xu et al. | |
| 9,301,835 B2 | 4/2016 | Campbell et al. | |
| 9,504,568 B2 * | 11/2016 | Ryan | A61F 2/2418 |
| 9,579,196 B2 * | 2/2017 | Morriss | A61F 2/2418 |
| 9,622,862 B2 * | 4/2017 | Lashinski | A61F 2/2463 |
| 9,855,141 B2 * | 1/2018 | Dienno | A61F 2/2418 |
| 9,937,037 B2 * | 4/2018 | Dienno | A61F 2/2418 |
| 2006/0276888 A1 | 12/2006 | Lee et al. | |
| 2008/0082161 A1 | 4/2008 | Woo | |
| 2009/0112309 A1 | 4/2009 | Jaramillo et al. | |
| 2009/0157175 A1 | 6/2009 | Benichou | |
| 2010/0161040 A1 | 6/2010 | Braido et al. | |
| 2010/0168839 A1 | 7/2010 | Braido et al. | |
| 2011/0276128 A1 * | 11/2011 | Cao | A61F 2/2409 623/2.11 |
| 2011/0282440 A1 * | 11/2011 | Cao | A61F 2/2412 623/2.18 |
| 2012/0323315 A1 | 12/2012 | Bruchman et al. | |
| 2013/0245753 A1 * | 9/2013 | Alkhatib | A61F 2/2418 623/2.18 |
| 2013/0268066 A1 * | 10/2013 | Rowe | A61F 2/2418 623/2.11 |
| 2013/0282114 A1 * | 10/2013 | Schweich, Jr. | A61F 2/243 623/2.19 |
| 2013/0304199 A1 * | 11/2013 | Sutton | A61F 2/2439 623/2.18 |
| 2013/0310928 A1 * | 11/2013 | Morriss | A61F 2/2418 623/2.12 |
| 2014/0128968 A1 * | 5/2014 | Benichou | A61F 2/2415 623/2.17 |
| 2014/0243958 A1 * | 8/2014 | Yang | A61F 2/2418 623/2.11 |
| 2014/0324160 A1 | 10/2014 | Benichou et al. | |
| 2015/0224231 A1 * | 8/2015 | Bruchman | A61F 2/2418 623/2.17 |
| 2016/0074161 A1 * | 3/2016 | Bennett | A61F 2/2418 623/2.17 |
| 2016/0175095 A1 * | 6/2016 | Dienno | A61F 2/2418 623/2.17 |
| 2017/0119523 A1 * | 5/2017 | Cao | A61F 2/2412 |

FOREIGN PATENT DOCUMENTS

| | | |
|---|---|---|
| WO | 02/49540 | 6/2002 |
| WO | 2008/133852 | 11/2008 |
| WO | 2011/147849 | 12/2011 |
| WO | 2012/032187 | 3/2012 |

* cited by examiner

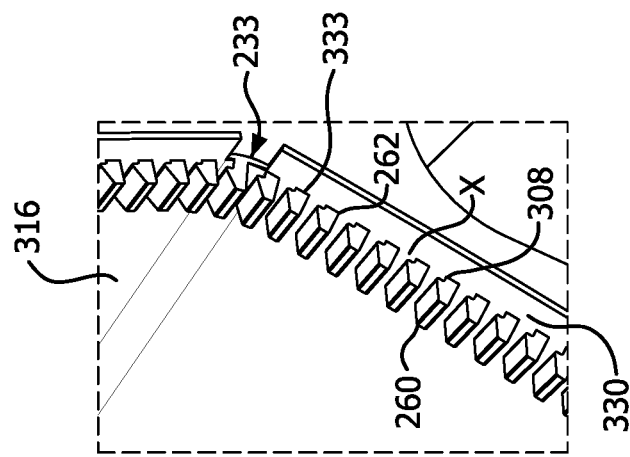
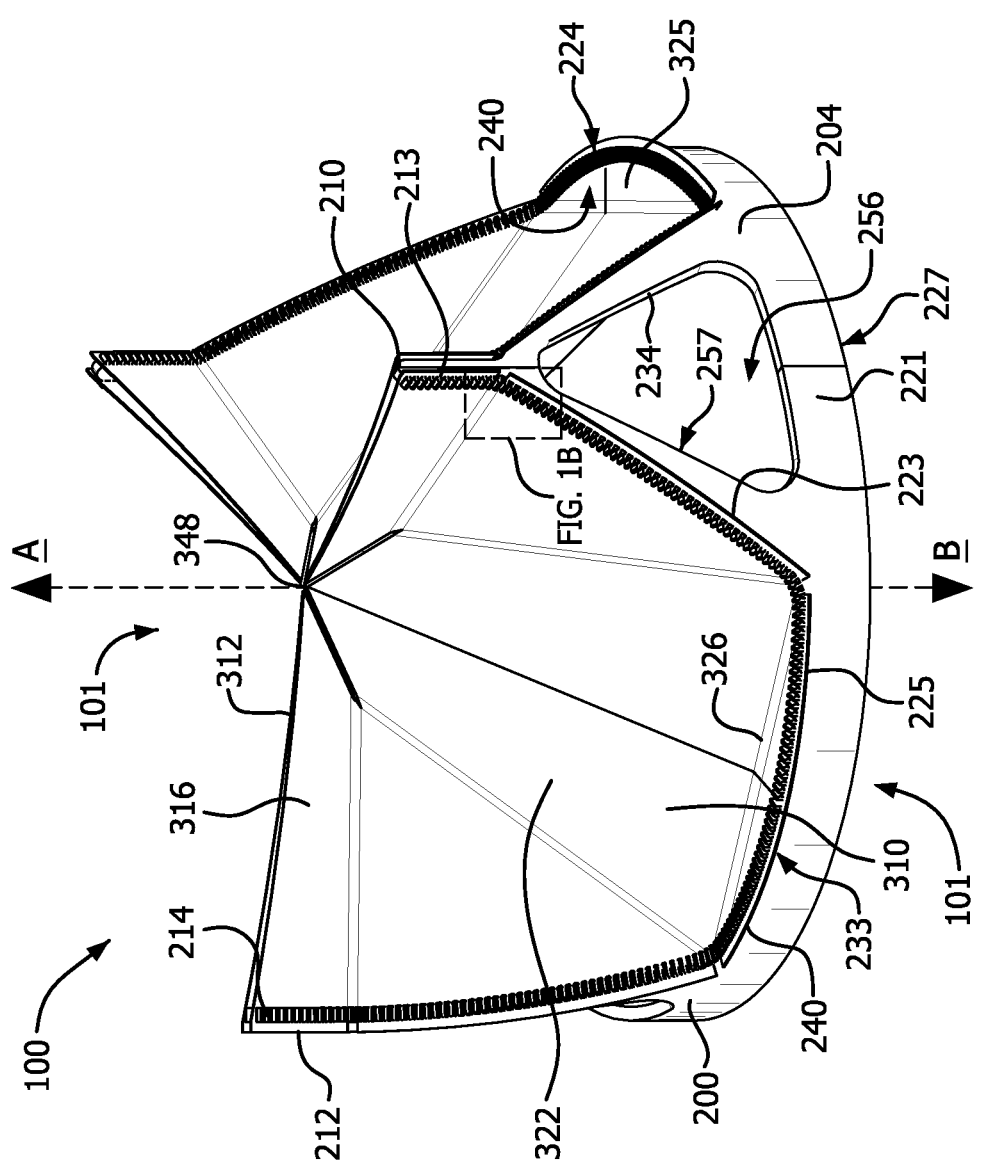

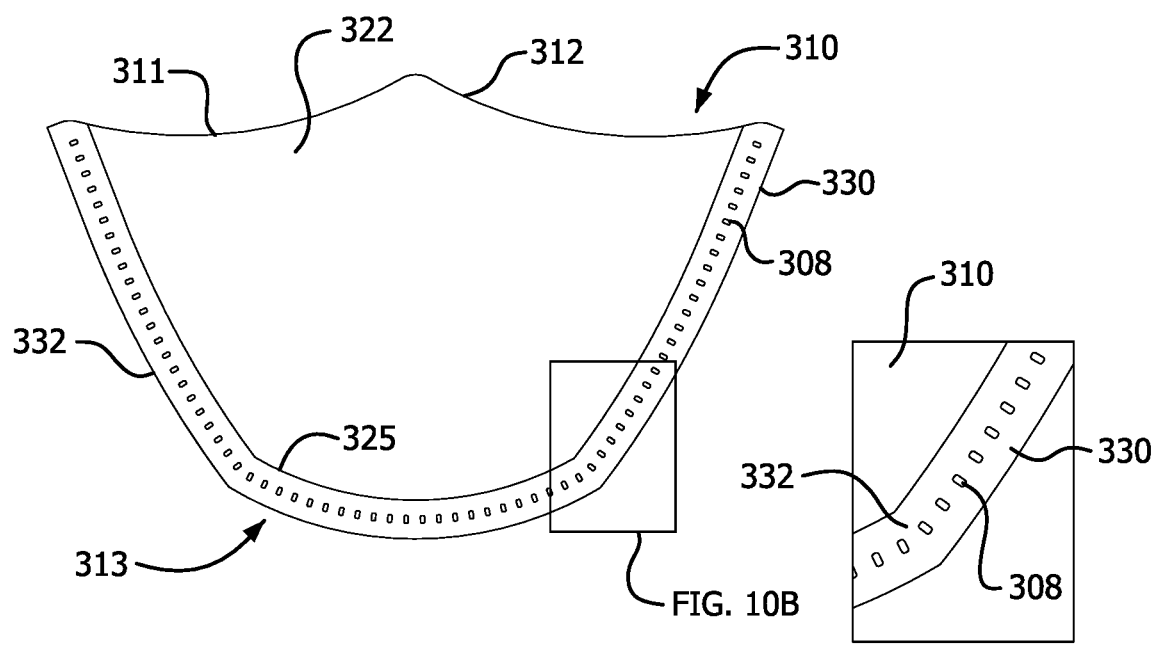
FIG. 10A
FIG. 10B
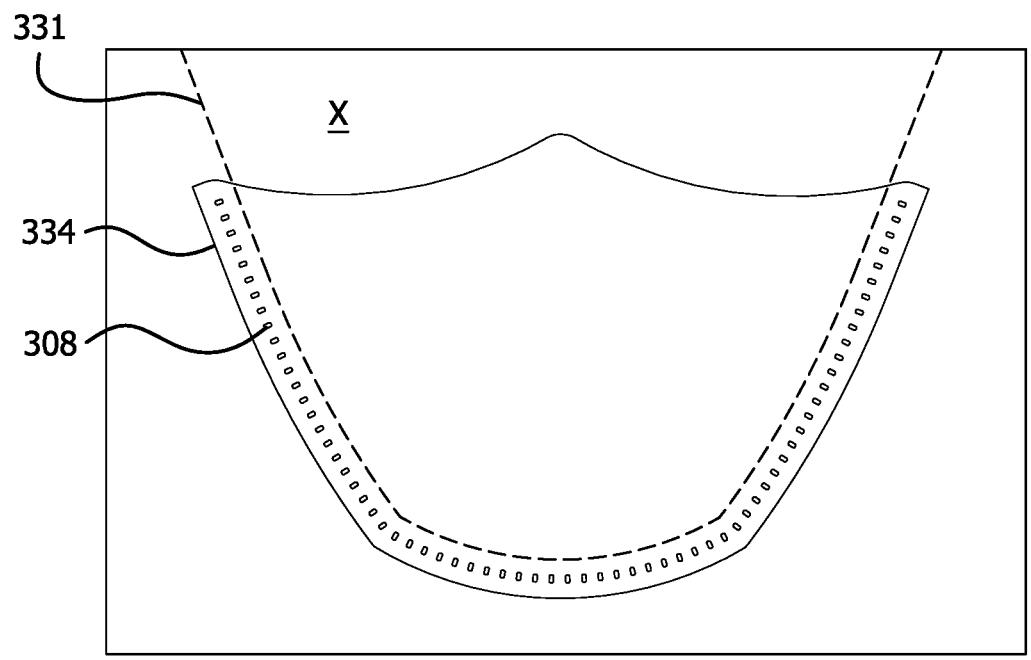
FIG. 10C

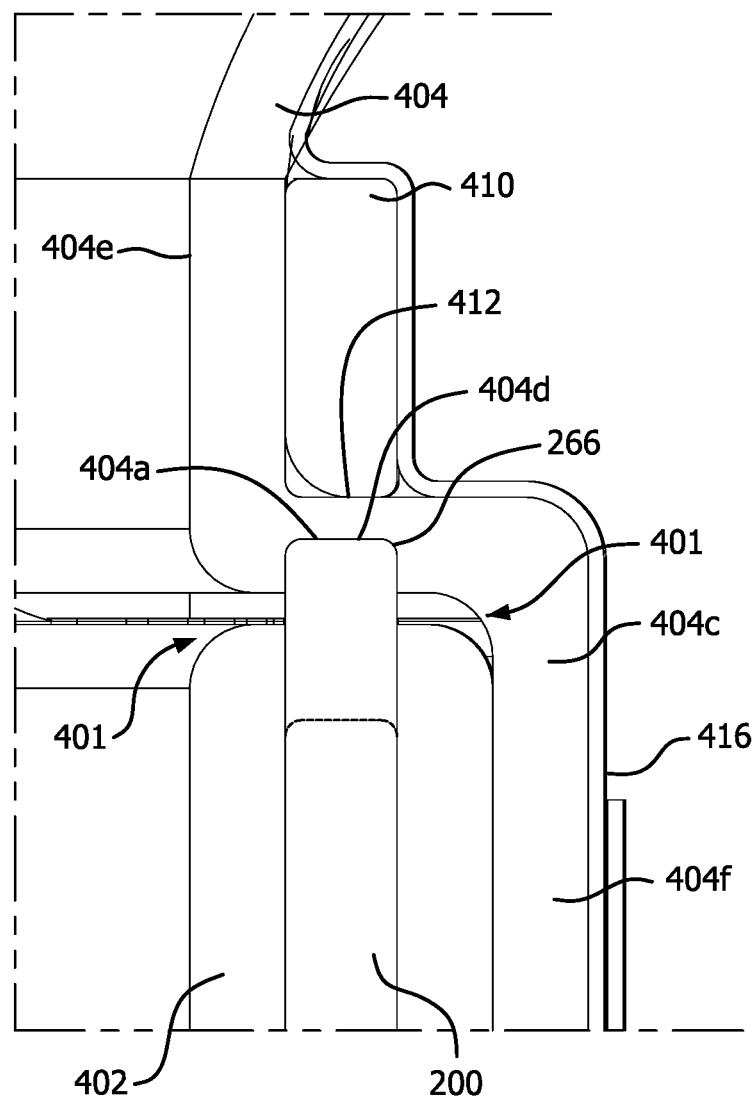
FIG. 20B(ii)

PROSTHETIC VALVES WITH MECHANICALLY COUPLED LEAFLETS

FIELD

The present disclosure relates generally to prosthetic valves and more specifically flexible leaflet-type prosthetic valve devices.

BACKGROUND

Prosthetic valves with flexible leaflets typically require some means for securing the leaflets to a support structure, such as a leaflet frame. The most common way for doing this is through suturing or adhesive/thermal bonding. Both techniques have disadvantages that affect the life and performance of a prosthetic valve.

In particular, the integrity of adhesive bonds tends to be negatively impacted in an aqueous environment, particularly on the time scale of a prosthetic valve. The suturing process tends to be labor-intensive, and the quality of the result may depend on the skill-level of the assembler. Moreover, the tension applied to the suture may not be well-controlled, which can affect the local geometries of the leaflet. All of these factors may adversely impact the functionality and structural integrity of the leaflets over the long term.

New ways of securing leaflets to support structures can be beneficial.

SUMMARY

Described embodiments are directed to apparatus, system, and methods for valve replacement, such as cardiac valve replacement, using a prosthetic valve. More specifically, described embodiments are directed toward flexible leaflet prosthetic valve devices with leaflets that are mechanically coupled to a leaflet frame.

More particularly, prosthetic valves of the present disclosure can comprise a leaflet frame and one or more leaflets that are each coupled to the leaflet frame with the assistance of a leaflet frame projection. The leaflet frame projections are configured to extend through an aperture defined by the leaflet in the leaflet attachment region. The leaflet frame projections can be disposed on one or more leaflet retention surfaces. Such surfaces are at least a portion of a leaflet frame edge, external and/or internal. The described structures impede leaflet decoupling from the leaflet frame during valve use.

Some embodiments of the present disclosure are directed to prosthetic valves comprising a leaflet frame defining an annular shape having a leaflet frame inner surface, a leaflet frame outer surface opposite the leaflet frame inner surface, and at least two leaflet frame edges extending between the leaflet frame inner surface and the leaflet frame outer surface, the leaflet frame having a plurality of leaflet frame projections extending from each of one or more leaflet retention surfaces, wherein the one or more leaflet retention surfaces comprises at least a portion of the one or more of the leaflet frame edges, the plurality of leaflet frame projections being spaced apart from each other; and one or more leaflets, each leaflet having a leaflet attachment region and a leaflet free edge, the leaflet attachment region defining a plurality of leaflet apertures spaced apart from each other such that each of the leaflet frame projections extends through a corresponding one of the plurality of leaflet apertures, and wherein the leaflets are retained on the leaflet frame.

Other prosthetic valve embodiments of the present disclosure can comprise one or more leaflets, each leaflet having a leaflet attachment region, the leaflet attachment region defining a plurality of leaflet apertures spaced apart from each other; and a leaflet frame defining an annular shape having one or more leaflet frame edges, wherein the leaflet frame has a plurality of leaflet frame projections extending from at least one leaflet frame edge and each of the leaflet frame projections extend through a corresponding one of the plurality of leaflet apertures. The prosthetic valve further comprises more restraining members coupled to or unitary with the leaflet frame projections configured to impede decoupling of the leaflets from the leaflet frame. Further embodiments of the leaflet frame can define one or more slots that extend through one or more frame elements that define the leaflet frame windows. Each slot is dimensioned to receive at least a single thickness of the leaflet, e.g., the leaflet attachment region. The slot can be a base receiving slot or a side receiving slot corresponding to respective portions of the leaflet attachment region. In addition, each commissure post defines a post slot dimensioned to receive a double thickness of the leaflet. In further embodiments, the frames can comprise attachment slot or other opening that defines an internal edge from which leaflet frame projections can extend.

Some embodiments of the present disclosure are directed to prosthetic valves comprising a leaflet frame defining an annular shape having a leaflet frame inner surface, a leaflet frame outer surface opposite the leaflet frame inner surface, and at least two leaflet frame edges extending between the leaflet frame inner surface and the leaflet frame outer surface. The leaflet frame having a plurality of leaflet frame projections extending from each of one or more leaflet retention surfaces, wherein each leaflet frame projection includes a projection base portion and a projection head portion opposite the projection base portion, the plurality of leaflet frame projections being spaced apart from each other. Including one or more leaflets, each leaflet having a leaflet attachment region and a leaflet free edge, wherein the one or more leaflet retention surfaces includes at least a portion of the one or more of the leaflet frame edges. Wherein each leaflet frame projection is coupled to the leaflet retention surface at the projection base portion. Each of the leaflet frame projections extends through the leaflet attachment region, and wherein the leaflets are retained on the leaflet frame. Further including a restraining element configured to provide a mechanical interference to impede decoupling of a respective leaflet from a respective leaflet frame projection. The restraining element is a deformable locking bar restraining element comprising a deformable locking bar including a bar base end and a bar free end opposite the bar base end, the deformable locking bar extending from the leaflet retention surface at the bar base end, and a locking clip coupled to the leaflet retention surface, wherein the locking clip is operable to couple with the bar free end. The deformable locking bar having a length that spans a distance between the bar base end and the locking clip. Wherein at least one leaflet frame projection is located between the bar base end and the locking clip. Wherein the deformable locking bar extends over the projection head portion of the at least one leaflet frame projection so as to impede decoupling of a respective leaflet from the respective leaflet frame projections.

Some embodiments of the present disclosure are directed to prosthetic valves comprising a leaflet frame defining an annular shape having a leaflet frame inner surface, a leaflet frame outer surface opposite the leaflet frame inner surface, and at least two leaflet frame edges extending between the leaflet frame inner surface and the leaflet frame outer surface. The leaflet frame having a plurality of leaflet frame projections extending from each of one or more leaflet retention surfaces, wherein each leaflet frame projection includes a projection base portion and a projection head portion opposite the projection base portion, the plurality of leaflet frame projections being spaced apart from each other. Including one or more leaflets, each leaflet having a leaflet attachment region and a leaflet free edge, wherein the one or more leaflet retention surfaces includes at least a portion of the one or more of the leaflet frame edges. Wherein each leaflet frame projection is coupled to the leaflet retention surface at the projection base portion. Each of the leaflet frame projections extends through the leaflet attachment region, and wherein the leaflets are retained on the leaflet frame. Further including a restraining element configured to provide a mechanical interference to impede decoupling of a respective leaflet from a respective leaflet frame projection. Wherein the restraining element is an attachable locking bar restraining element comprising an attachable locking bar including a bar-shaped element with a retention hook at each end, and a pair of locking clips spaced apart and coupled to the leaflet retention surface, wherein each of the locking clips is operable to couple with a respective retention hook of the locking bar. The attachable locking bar having a length that spans a distance between the pair of locking clips. Wherein at least one leaflet frame projection is located between the pair of locking clips. Wherein the attachable locking bar extends over the projection head portion of the at least one leaflet frame projection so as to impede decoupling of a respective leaflet from the respective leaflet frame projections.

Further embodiments of the present disclosure comprise valved conduits where such leaflet frames can be coupled to one or more conduits. For example, the valved conduit can comprise a first frame defining an annular shape having a first frame first edge and a first frame second edge opposite the first frame first edge, wherein the first frame first edge is substantially complementary to the leaflet frame second edge and a first conduit defining a tubular shape having a first conduit first luminal end, a first conduit second luminal end, and a first conduit lumen therethrough, wherein the first conduit has a first conduit mating surface at the first conduit second luminal end that defines a plurality of first conduit apertures spaced apart from each other such that each of the leaflet frame projections extends through a corresponding one of the plurality of leaflet apertures, wherein the first conduit mating surface is disposed between the leaflet frame second edge and the leaflet attachment region, and wherein the leaflet frame is fixedly coupled to the first frame such that the first conduit mating surface and the leaflet attachment region are retained therebetween.

Other valved conduit embodiments of the present disclosure can comprise a first conduit; a second conduit; a leaflet frame defining an annular shape having a leaflet frame first edge and a leaflet frame second edge opposite the leaflet frame first edge; a first frame defining an annular shape having a first frame first edge and a first frame second edge opposite the first frame first edge, wherein the first frame first edge is substantially complementary to the leaflet frame second edge; one or more leaflets, each leaflet having a leaflet attachment region and a leaflet free edge, wherein the leaflet attachment region of each leaflet is disposed between the leaflet frame second edge and the first frame first edge, the leaflet attachment region disposed at a junction between the first conduit and the second conduit; the first conduit defining a tubular shape having a first conduit first luminal end, a first conduit second luminal end, and a lumen therethrough, wherein the first conduit defines a first conduit mating surface at the first conduit second luminal end that is disposed between the leaflet frame second edge and the leaflet attachment region; and the second conduit defining a tubular shape having a second conduit first luminal end, a second conduit second luminal end, and a lumen therethrough, wherein the second conduit defines a second conduit mating surface at the second conduit first luminal end that is disposed between the first frame first edge and the leaflet attachment region, wherein the leaflet frame is fixedly coupled to the first frame whereby retaining the leaflet attachment region between the first conduit mating surface and the second conduit mating surface.

Yet other valved conduit embodiments of the present disclosure can comprise a first conduit; a second conduit; and a prosthetic valve comprising a leaflet frame defining an annular shape having a leaflet frame first edge and a leaflet frame second edge opposite the leaflet frame first edge, and one or more leaflets, each leaflet having a leaflet attachment region and a leaflet free edge, wherein the leaflet attachment region of each leaflet coupled to the leaflet frame second edge, the leaflet attachment region disposed at a junction between the first conduit and the second conduit, each leaflet having a leaflet inflow side and a leaflet outflow side opposite the leaflet inflow side, the first conduit extending between a first conduit first end and a first conduit second end and defining a first conduit lumen on the leaflet inflow side of the leaflets, wherein the leaflet frame circumscribes a section of the first conduit and is coupled to the first conduit second end, and the second conduit extending between a second conduit first end and a second conduit second end and defining a second conduit inner surface, with a second conduit first portion nearer the second conduit second end defining a lumen on the leaflet outflow side of the leaflets and a second conduit second portion nearer the second conduit first end defining a circumferential recess on the second conduit inner surface, the circumferential recess having a shape that substantially complements the shape of the leaflet frame, wherein the leaflet frame is disposed within the circumferential recess, and wherein the first conduit is coupled to the second conduit.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The features and advantages of the present disclosure will become more apparent from the detailed description set forth below when taken in conjunction with the drawings.

FIG. 1A is an outflow-side, perspective view of a prosthetic valve in accordance with an embodiment;

FIG. 1B is a magnified view of Box 1B in FIG. 1A;

FIG. 10A is a top view of the leaflet of the prosthetic valve embodiment of FIG. 1A in a flattened configuration;

FIG. 10B is a magnified view of Box 10B in FIG. 10A;

FIG. 10C is a top view of a coupon template illustrating the cut lines that were made on two coupons in the making of a leaflet, as described in Example 1;

FIG. 20B(ii) is a cross-sectional view of the valved conduit shown in FIG. 9A in the vicinity of a junction between the prosthetic valve, a first conduit, and a second conduit at the base of a leaflet frame concavity and at a leaflet frame projection;

DETAILED DESCRIPTION

Figure 1C:
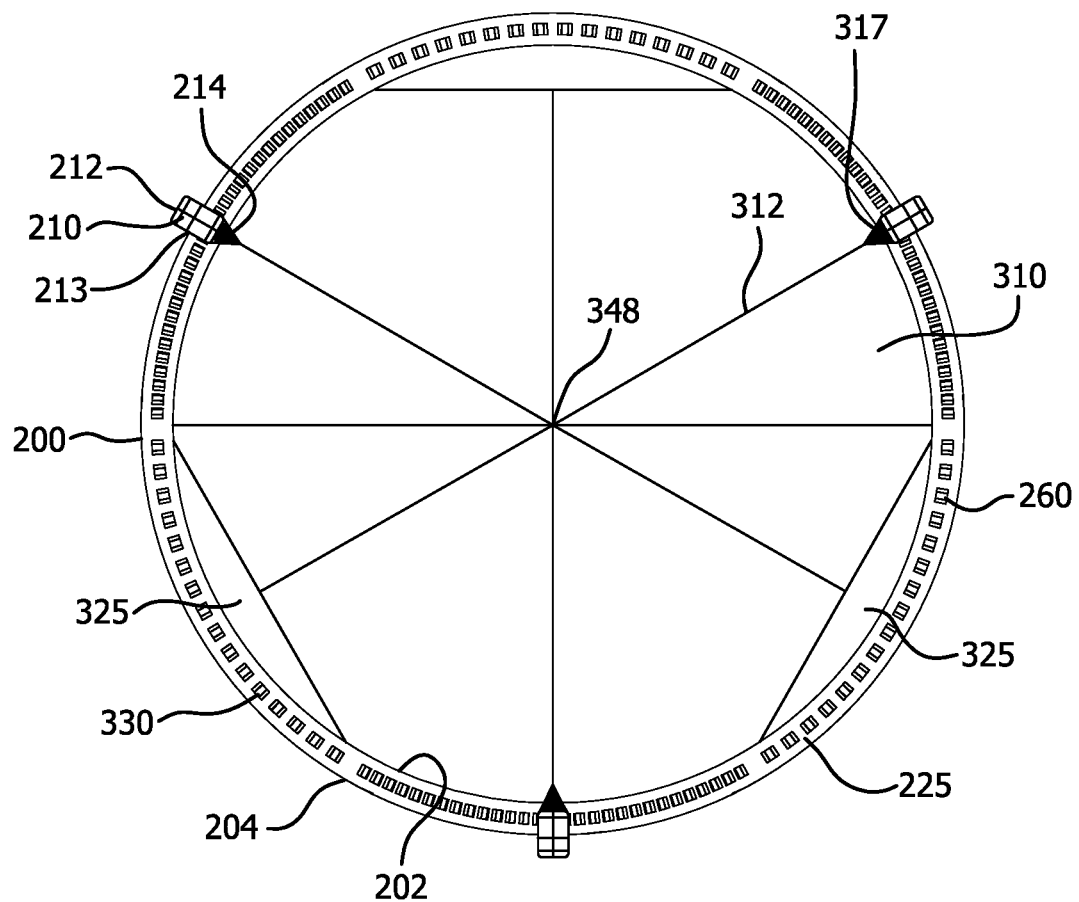
FIG. 1C is a top view of the prosthetic valve embodiment of FIG. 1A.

Persons skilled in the art will readily appreciate that various aspects of the present disclosure can be realized by any number of methods and apparatuses configured to perform the intended functions. Stated differently, other methods and apparatuses can be incorporated herein to perform the intended functions. Furthermore, a structure that is capable of performing a function or that is configured in a certain way is capable or configured in at least that way, but may also be capable or configured in ways that are not listed. It should also be noted that the accompanying drawing figures referred to herein are not all drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves and prosthetic valved conduits, particularly for cardiac applications. Embodiments within the scope of this disclosure can be applied toward any cardiac or non-cardiac valve or mechanism of similar structure and/or function.

The term "leaflet" as used herein in the context of prosthetic valves is a component of a one-way valve wherein the leaflet is operable to move between an open and closed position under the influence of a pressure differential. In an open position, the leaflet allows blood to flow through the valve orifice. In a closed position, the leaflet substantially blocks retrograde flow through the valve orifice. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the prosthetic valve rises above the pressure on the outflow side of the prosthetic valve, the leaflets will open and blood will flow therethrough. As blood flows through the prosthetic valve into a neighboring chamber or blood vessel, the pressure on the inflow side equalizes with the pressure on the outflow side. As the pressure on the outflow side of the prosthetic valve rises above the blood pressure on the inflow side of the prosthetic valve, the leaflet returns to the closed position generally preventing retrograde flow of blood through the prosthetic valve.

The term "membrane" as used herein refers to a sheet of material comprising a single composition, such as, but not limited to, expanded fluoropolymer.

The term "composite material" as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term "laminate" as used herein refers to multiple layers of membrane, composite material, or other materials, such as elastomer, and combinations thereof.

The term "film" as used herein generically refers to one or more of the membrane, composite material, or laminate.

The term "leaflet frame element" as used herein refers to any portion of a leaflet frame, such as, but not limited to, those portions that define a leaflet window. A leaflet frame element can be a commissure post, a leaflet window side, and/or a leaflet window base.

A leaflet frame "edge" is defined as a surface or surfaces of the leaflet frame that extends between a leaflet frame inner surface and a leaflet frame outer surface. An internal edge is an edge that is enclosed by frame elements such that it is bounded by the frame elements, whereas an external edge is not enclosed by frame element such that it is not bounded by frame elements.

The term "leaflet window" is defined as the space that a leaflet frame defines within which a leaflet contacts the leaflet frame. The leaflet can contact the leaflet frame at an edge that is either an internal edge or an external edge.

The term "leaflet attachment region" as used herein refers to a portion of the film that contacts the leaflet frame.

The term "spatial pattern" as used herein refers to the arrangement of objects/features in two- or three-dimensional space, such as in a cluster of points.

The terms "native valve orifice" and "tissue orifice" refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a prosthetic valve.

As used herein, "couple" means to join, connect, attach, adhere, affix, or bond, whether directly or indirectly, and whether permanently or temporarily.

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The preposition "between," when used to define a range of values (e.g., between x and y) means that the range includes the end points (e.g., x and y) of the given range and the values between the end points.

Embodiments herein include various apparatus, systems, and methods for a prosthetic valve suitable for surgical and transcatheter placement, such as, but not limited to, cardiac valve replacement. The prosthetic valve is operable as a one-way valve wherein the prosthetic valve defines a valve orifice into which leaflets open to permit flow and close so as to occlude the valve orifice and prevent flow in response to differential fluid pressure.

Various embodiments provided herein relate to a non-sewn or minimally sewn, mechanically coupled leaflet that is coupled, in this mechanical manner, to a leaflet frame along a leaflet attachment region or a section thereof. Described leaflet frame projections allow for simple, reproducible coupling of a leaflet to a leaflet frame, which can be beneficial in either a manufacture or a research setting. A leaflet frame projection on the leaflet frame can be an integral part of the leaflet frame that projects from one or more leaflet retention surfaces. The leaflet frame projections are configured to extend through an aperture defined by the leaflet in the leaflet attachment region.

Some embodiments provided herein relate to leaflets made from a flat pattern. The leaflet can be made separately from the leaflet frame and then upon attachment to the leaflet frame, the leaflet obtains its operable shape, as the shape of leaflet frame elements that define a leaflet window, the two-dimensional shape of the leaflet, and the line of attachment are the primary determinants of the resulting three-dimensional operable shape of the leaflet. Thus, in some embodiments, this aspect can negate the need for leaflet shape-setting to a three-dimensional shape.

As the leaflets and leaflet frames can be manufactured independently and the attachment process does not require sewing or adhesion/thermal bonding, the process of producing a prosthetic valve may be simplified, which can translate to manufacturing efficiencies. Moreover, embodiments provided herein can be particularly useful in a research context because of the option of a simplified process in making a leaflet and the leaflet frame and coupling the two together, allowing for quick prototyping.

In accordance with a present disclosure, a prosthetic valve can comprise a leaflet frame defining an annular ring and having a leaflet contact surface configured to impart a shape to the leaflet that provides proper function of the valve and one or more leaflet retention surfaces to facilitate leaflet retention to the leaflet frame. The leaflet contact surface can be the same as or different from the leaflet retention surface. A plurality of leaflet frame projections that are spaced from each other can be coupled to or integral with the leaflet retention surface. The leaflet frame projections are configured to assist in retaining the leaflet to the leaflet frame.

The prosthetic valve also comprises one or more leaflets with each leaflet having a leaflet attachment region and a region terminating at a leaflet free edge. The leaflet attachment region can define a plurality of leaflet apertures spaced apart from each other such that each of the leaflet frame projections extend through a corresponding one of the plurality of leaflet aperture when the two components are coupled. In other words, a spatial pattern of the leaflet frame projections is the same as a spatial pattern of the leaflet apertures. The coupling of the leaflet frame projections to the leaflets facilitates the retention of the leaflet on the leaflet frame. It is appreciated that embodiments of this disclosure are suitable for prosthetic valves having one, two, three or more leaflets.

Other embodiments provided herein include various apparatus, systems, and methods for prosthetic valved conduits, such as, but not limited to, prosthetic pulmonary valved conduits, that can incorporate the above described prosthetic valve. The described prosthetic valved conduits provide for a generally smooth inner surface transition at a junction between the conduit-valve-conduit, as compared with a stepped-transition. A smoother transition can facilitate improved hemodynamics and provide a less irregular surface where thrombus formation might occur. In addition, the method of making the described prosthetic valves and prosthetic valved conduits is accurately repeatable and semi-automatable.

Prosthetic Valve

FIG. 1A is an outflow perspective view of a prosthetic valve 100, in accordance with an embodiment, shown in a closed configuration. FIG. 1B is a magnified view of Box 1B in FIG. 1A. FIG. 1C is a top view of the prosthetic valve 100 in FIG. 1A, also shown in a closed configuration. The components of the prosthetic valve 100 that can be observed in FIG. 1A include a plurality of leaflets 310 and a leaflet frame 200 that includes a plurality of commissure posts 210 flanked on each side by leaflet window frame element(s) (e.g., two leaflet window sides 223 and a leaflet window base 225 therebetween) that define the leaflet window 222 (labeled in FIG. 2A). Leaflet free edges 312 of the leaflets 310 come together at a coaptation region 316 in a Y-shaped pattern (when viewed from above, e.g., in FIG. 1C) to close the prosthetic valve 100. The prosthetic valve 100 closes in this fashion when the pressure of the blood on the leaflet outflow side A is greater than the pressure of the blood on the leaflet inflow side B of the prosthetic valve 100. The leaflet free edges 312 of the leaflets 310 move apart to open the prosthetic valve 100 and to let blood flow through the prosthetic valve 100 from the leaflet inflow side B when the pressure of the blood on the leaflet inflow side B is greater than the pressure on the outflow side A.

FIG. 1B shows a magnified view of a leaflet frame projection 260 on the leaflet frame 200 about which a leaflet aperture 308 is disposed. In the embodiment shown, the leaflet frame projections 260 are located on a leaflet frame second edge 224.

Figure 2A:
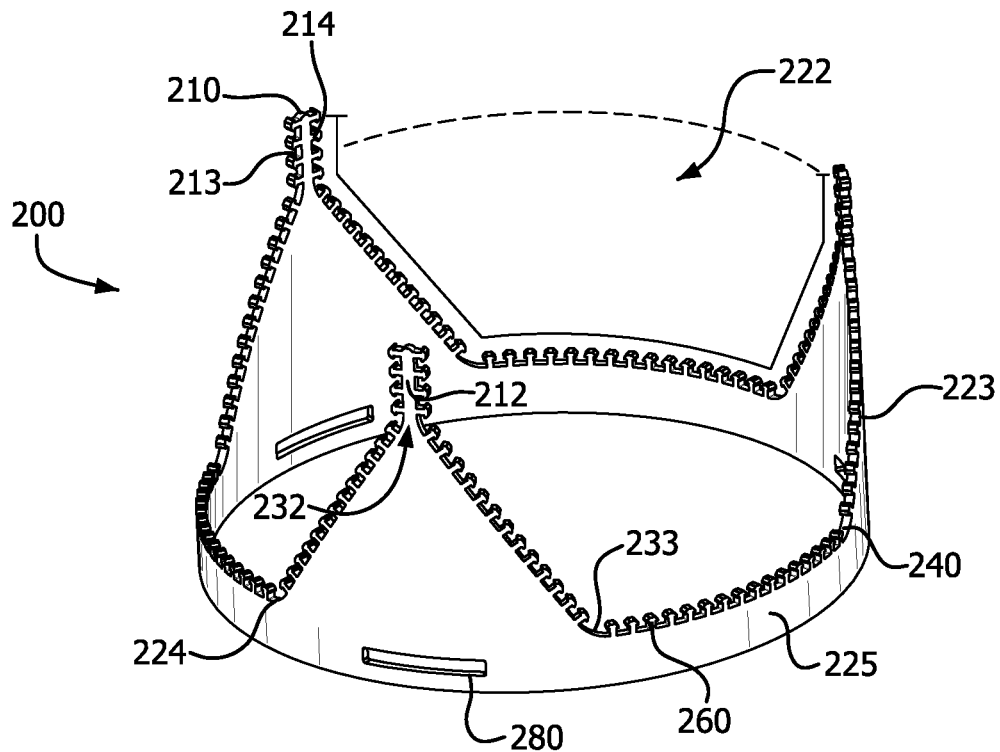
FIG. 2A is an outflow-side, perspective view of a leaflet frame in accordance with an embodiment.
Figure 2B:
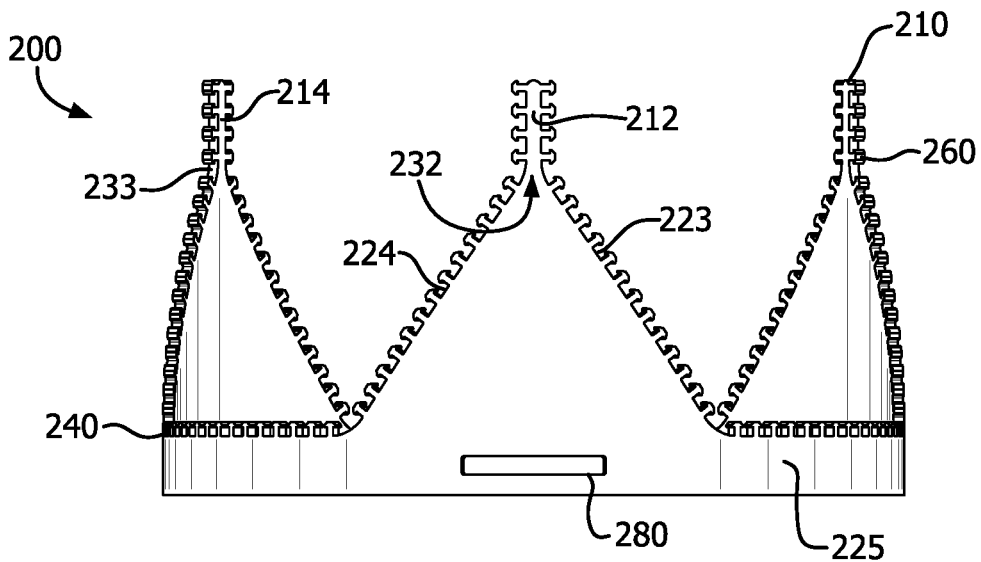
FIG. 2B is a side view of the leaflet frame embodiment of FIG. 2A.

FIGS. 2A and 2B show a perspective view and a side view, respectively, of the leaflet frame 200 in accordance with an embodiment. FIGS. 3A-3D show various views of another embodiment of the leaflet frame 200. FIGS. 4A-4D show various views of yet another embodiment of the leaflet frame 200. The exploded view shows the annular components longitudinally cut, opened, and laid flat so as to better illustrate the elements of the leaflet frame 200. FIG. 5 shows an exploded, perspective view of still another embodiment of the leaflet frame 200 that is configured to couple with a leaflet frame jacket 290 for retaining the leaflets 310.

Figures 7A, 7B:
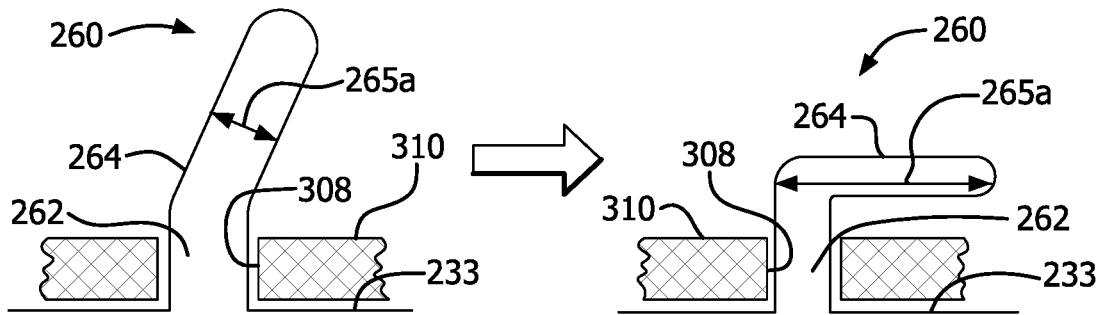
FIGS. 7A and 7B are side views of an embodiment of a leaflet frame projection.

FIG. 10A shows a top view of the leaflet of FIG. 1A in a flat configuration, and FIG. 7B shows a magnified view of Box 10B of FIG. 10A. While the leaflets 310 of FIG. 10B are shown flat to better show the shape and features, it is understood that the shape of the leaflet when coupled to the frame is determined, at least in part, by the shape of the leaflet frame, the shape of the leaflet attachment edge, and the fluid pressure that the leaflet encounters during operation.

Leaflet Frame

The leaflet frame 200 is operable to mechanically couple and support the leaflets 310 by way of, at least in part, a plurality of leaflet frame projections 260 that are spaced-apart and project from one or more leaflet retention surfaces 233 of the leaflet frame 200. In various embodiments, the one or more leaflet retentions surfaces 233 are one or more leaflet frame edges, external edges or internal edges, such as a leaflet frame first edge 227, a leaflet frame second edge 224, and a leaflet frame internal edges 234. The leaflet frame projections 260 are each configured to extend through a leaflet aperture 308 defined by the leaflet 310 within the leaflet attachment region 330. In some embodiments, the leaflet frame projections 260 can have a tenon-like shape.

The leaflet frame 200 defines an annular shape and has a central longitudinal axis A-B. The leaflet frame comprises a plurality of commissure posts 210 that are spaced from one another and substantially parallel with axis A-B. Between two commissure posts 210 is a leaflet window 222. The portion of the leaflet frame 200 disposed adjacent each commissure post 210 can be an opening, an open framework, or a continuous wall, which may be further defined in part by the leaflet window sides 223. The leaflet retention surface 233 in the embodiment shown in FIG. 1A is the leaflet frame second edge 224 (an example of a leaflet frame external edge), but it is understood that a leaflet retention surface 233 can include any leaflet frame surface including, but not limited to, a leaflet frame second edge 224, a leaflet frame first edge 227, and/or a leaflet frame internal edge 234, such as the side internal edge 257 defining triangular opening 256.

Figure 4A:
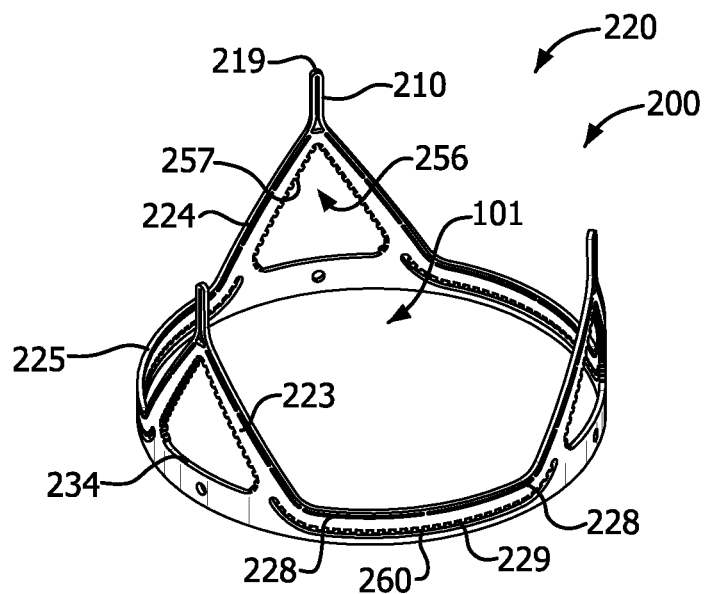
FIG. 4A is an outflow-side, perspective view of a leaflet frame in accordance with an embodiment.
Figure 5:
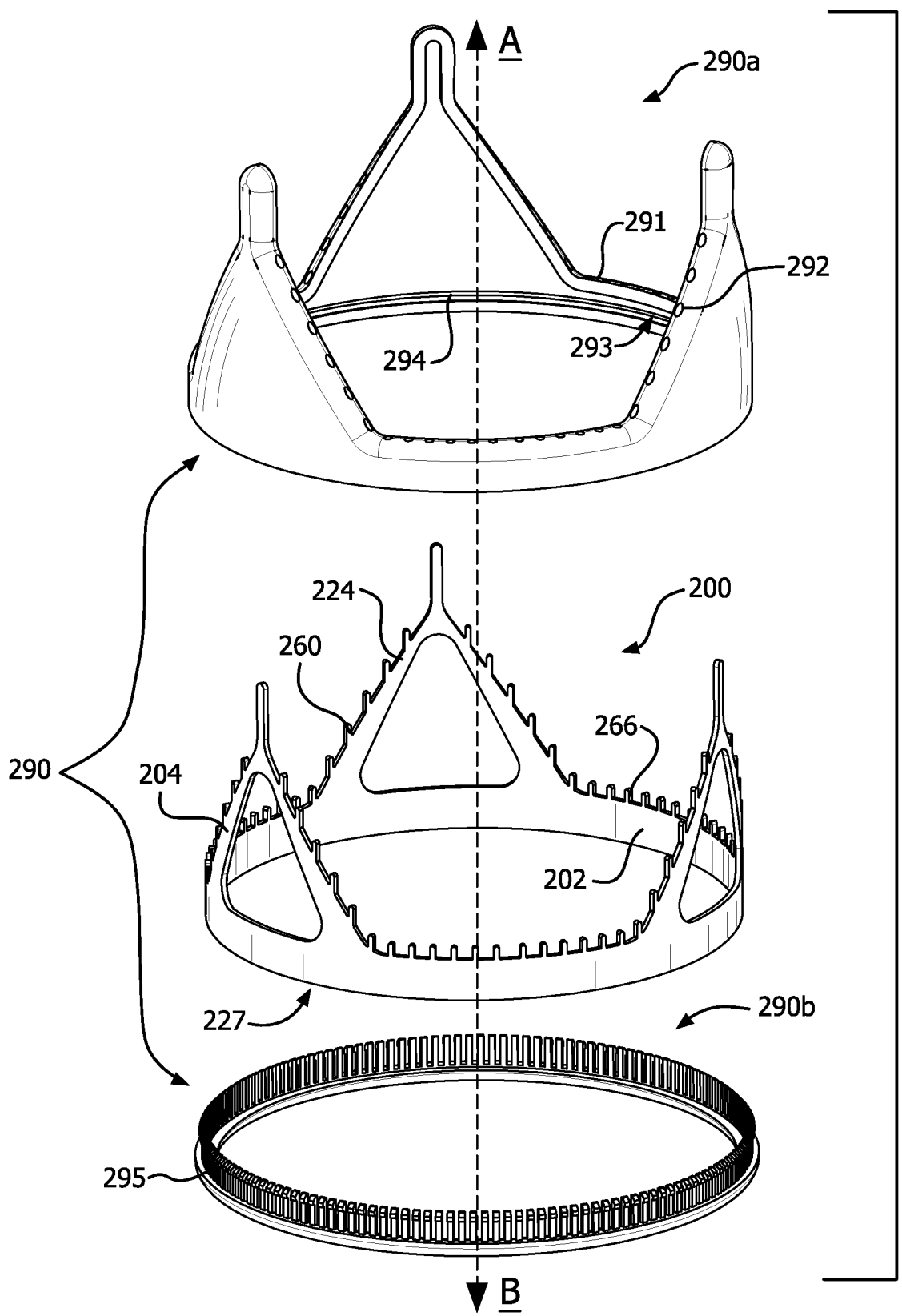
FIG. 5 is an exploded, perspective view of a leaflet frame and a leaflet frame jacket, in accordance with an embodiment.

In the embodiments shown in FIGS. 1A, 4A, each of the leaflet windows 222 is defined by the leaflet frame second edge 224. In particular, the leaflet frame second edge 224 defines a leaflet frame concavity 240 corresponding to each leaflet window 222. The leaflet frame concavity 240 can be curved or angular. The shown embodiment has an angular leaflet frame concavity 240. A set of leaflet frame elements that, along with the commissure post 210, define each leaflet window 222 are referred to as leaflet window frame elements. A set of leaflet window frame elements can flank each side of a commissure post 210. The set of leaflet window frame elements can include two leaflet window sides 223 and a leaflet window base 225 therebetween. The leaflet window base 225 and the leaflet window sides 223 are configured to couple to and support, along with the commissure posts 210, each leaflet 310 around the perimeter thereof except for the leaflet free edge 312. The commissure post 210 extends from an apex 232 in the outflow direction that is formed at the convergence between two leaflet window sides 223 of adjacent leaflet windows 222. The extent of leaflet attachment along the commissure post 210 can affect the leaflet free edge 312 so as to create a narrower or wider coaptation region 316 between the adjacent leaflets free edges 312 where the extent is less or more, respectively. It is also understood that the shape of the leaflet free edge 312 and dimensions of the leaflet belly region 322 influence wider or narrower coaptation.

The leaflet frame 200 defines an annular shape having a leaflet frame inner surface 202 and a leaflet frame outer surface 204 opposite the leaflet frame inner surface 202. Further, the leaflet frame 200 has a leaflet frame first edge 227 and a leaflet frame second edge 224 opposite the leaflet frame first edge 227. Similarly, each commissure post 210 has a post outer side 212 and a post inner side 214 opposite the post outer side 212. Further, each commissure post 210 has two post lateral sides 213 that are opposite each other and extending between the post inner side 214 and the post outer side 212 such that all sides, namely, the post outer side 212, the two post lateral sides 213, and the post inner side 214, define a perimeter of each commissure post 210.

In accordance with an embodiment, the leaflet frame 200 is annular about a central longitudinal axis A-B of the prosthetic valve 100 as shown in FIG. 1A. The leaflet frame 200 defines three leaflet windows 222, each of which follow the shape of the leaflet attachment region 330 of the leaflet 310. In the embodiment shown, a leaflet window base 225 is flanked on each side by two leaflet window sides 223 that together define three sides of an arced isosceles trapezoid, wherein the leaflet frame second edge 224 at the leaflet window base 225 is substantially flat. The leaflet attachment region 330 is coupled to the leaflet window base 225, each of the two leaflet window sides 223, and the commissure posts 210. The commissure posts 210 can be equally spaced from one another around the leaflet frame 200. The portion of the leaflet frame 200 that is disposed under each commissure post 210 and between adjacent leaflet windows 222 is a framed triangular opening 256 defined by leaflet frame internal edges 234 of neighboring leaflet window sides 223 and the leaflet frame base 221. While the triangular opening 256 is shown as open, it can be capped or sealed in various embodiments.

On portions of the leaflet frame second edge 224 at the leaflet window sides 223, the leaflet window base 225, and the commissure post 210, referred to as leaflet retention surfaces 233, are located a plurality of leaflet frame projections 260. Each of a plurality of the leaflet frame projections 260, but not necessarily all of the leaflet frame projections 260, is disposed within a corresponding one of a plurality of leaflet apertures 308. The projection-aperture junctions 333 are made more discernible in the magnified view of Box 1B shown in FIG. 1B. The leaflet frame projections 260 can extend from one or more leaflet retention surfaces 233 and can be configured to each extend through one of the leaflet apertures 308 to restrain the leaflet 310 and/or impede leaflet uplift away from the leaflet retention surface 233. The leaflet frame projections 260 can be an integral part of or unitary with the leaflet frame 200 and project from the one or more leaflet retention surfaces 233, such as the leaflet frame second edge 224, in a direction normal to the surface (as shown) or off-normal (i.e. at an angle of less than 90 degrees to the leaflet retention surface 233). In various leaflet frame embodiments, such as the leaflet frame 200 shown in FIG. 2A, all the leaflet frame projections 260 project from the leaflet retention surface 233 in a direction that is substantially normal to the leaflet retention surface 233. In other leaflet frame embodiments, such as the leaflet frame 200 shown in FIG. 5, all the leaflet frame projections 260 are substantially parallel with central longitudinal axis A-B. Various configurations of leaflet frame projections 260 are shown in FIGS. 1B, 6A-6E, 7A-7B, 8A-8B, and 9A-9B.

Two neighboring leaflet frame projections 260 can be spaced-apart from each other a distance X (e.g., see FIG. 1B) that sufficiently disperses the load on the leaflet attachment region 330 without significantly affecting the structural integrity thereof. In addition, the distance can be small enough for the leaflet attachment region 330 to abut sufficiently with the leaflet retention surface 233 so that fluid leakage between the two is insignificant or non-existent. In various embodiments, this distance can be between 0.5 mm to 2 mm, such as 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2 mm.

In various embodiments, the leaflet frame projection 260 is coupled to or unitary with a restraining element configured to provide a mechanical interference to impede leaflet decoupling from each leaflet frame projection 260. For example, the leaflet frame projection 260 itself can be configured to impede leaflet decoupling. In particular, the leaflet frame projection 260 can define a projection base portion 262 and a projection head portion 264 that defines a projection tip 266 (e.g., a projection head portion tip). The projection base portion 262 meets the leaflet retention surface 233 (in this case, the leaflet frame second edge 224) at one end and the projection head portion 264 at its opposite end. The projection head portion 264 meets the projection base portion 262 at one end and terminates at the projection tip 266 at its opposite end.

Figure 6A:
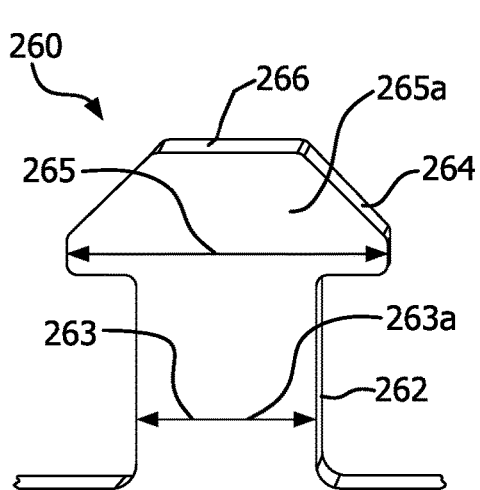
FIGS. 6A to 6E are perspective views of various embodiments of leaflet frame projections defining various tenon-like shapes.
Figure 6B:
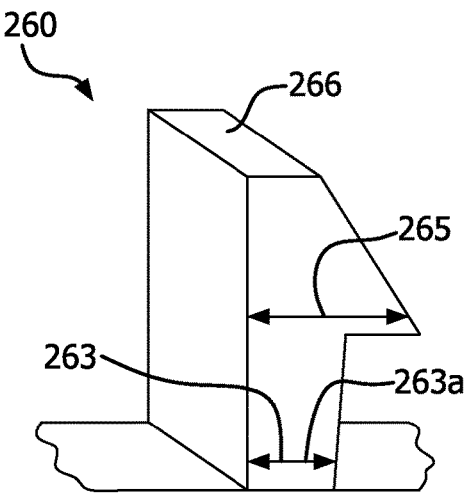
Figure 6C:
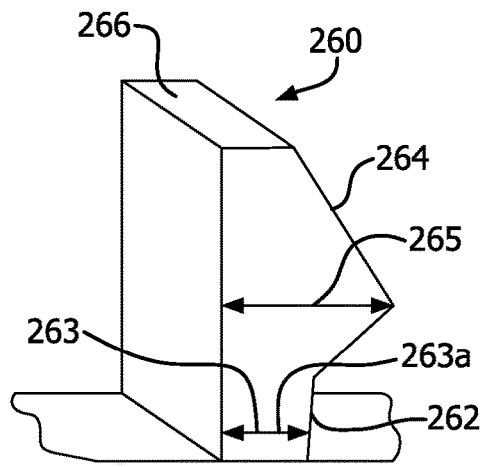
Figure 6D:
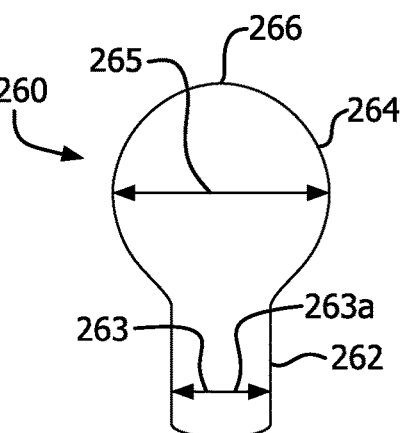

In various embodiments, the projection head portion 264 has a wider transverse dimension 265 than a transverse dimension 263 of the projection base portion 262. The transition between the wider projection head portion 264 and the narrower projection base portion 262 can be gradual, abrupt, or something therebetween. For example, the projection head portion 264 can define a bulbous shape (as shown in FIG. 6D), or an angular overhang, such as on one or both post lateral sides 213 (as shown in FIGS. 6A to 6C). In various embodiments, the relative difference in the largest transverse dimension 265 within the projection head portion 264, referred to as a projection head portion transverse dimension 265*a*, compared to the narrowest transverse dimension 263 within the projection base portion 262, referred as the projection base portion transverse dimension 263*a*, can be between 20% to 160%, such as greater than 30%, 40%, 50%, 60%, 70%, 80%, 90, 100%, 110%, 120%, 130% 140%, 150%, or any value or range derivable therein. In various embodiments, the narrowest transverse dimension 263 within the projection base portion 262 can be directly adjacent the leaflet retention surface 233 with which the projection base portion 262 meets.

Figure 6E:
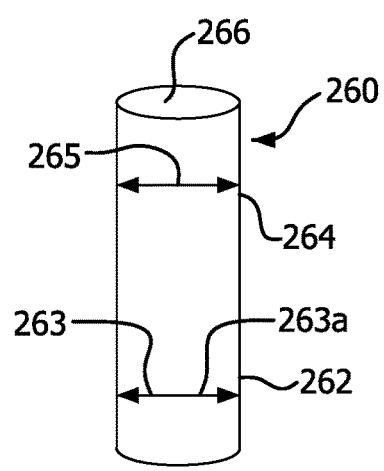

Other projection configurations are also contemplated. In other embodiments, the projection head portion 264 and the projection base portion 262 have the substantially same transverse dimension or cross-sectional area. For example, the leaflet frame projections 260 may define a helical column. In another variation, the leaflet frame projection 260 is a straight post projecting from the leaflet retention surface 233, an embodiment of which is shown in FIG. 6E.

In various embodiments, the projection head portion 264 can be tapered such that the projection head portion tip 266 has a smaller surface area than the cross-sectional area at the largest, transverse cross-section of the projection head portion 264. In addition, the projection tip 266 is dimensioned such that the surface area of the projection tip 266 is less than the area of the leaflet aperture 308. This shape guides the leaflet 310 at one of the leaflet apertures 308 onto the leaflet frame projection 260 during the attachment process in manufacturing.

In some embodiments, the projection head portion 264 can be pointed to facilitate puncturing of the leaflets 310 to form the leaflet apertures 308 during the attachment process. Pointed head portions can also facilitate puncturing of a conduit in the formation of a prosthetic valved conduit described hereafter.

The cross-sectional shape of the projection base portion 262 can be any shape, such as triangular, rectangular (e.g., square) or rounded (e.g., oval or circle). In various embodiments, the shape and dimension of the projection base portion 262, particularly at the leaflet retention surface 233, is substantially the same as the shape and dimension of the leaflet aperture 308, except the leaflet aperture 308 can be slightly larger in dimension such that no strain or only negligible strain is placed on that portion of the leaflet attachment region 330 that defines the leaflet aperture 308 when seated adjacent the leaflet retention surface 233 of the leaflet frame 200 about the projection base portion 262.

Other embodiments of the leaflet frame projections 260 are operable to change shape or deform so as to retain the leaflet 310 to the leaflet retention surfaces 233. In the embodiment of FIGS. 7A-7B, the projection head portion 264 has a projection head portion transverse dimension 265*a* that is uniform along the length, as shown in FIG. 7A, over which the leaflet aperture 308, shown in FIG. 1B, may be disposed. Subsequent to disposing the leaflet aperture 308 over the projection head portion 264, the projection head portion 264 may be deformed operable to retain the leaflet 310 to the leaflet retention surface 233, as shown in FIG. 7B, essentially providing the projection head portion 264 with a largest projection head portion transverse dimension 265*a* that is larger than a dimension of the leaflet aperture 308.

Figures 8A, 8B:
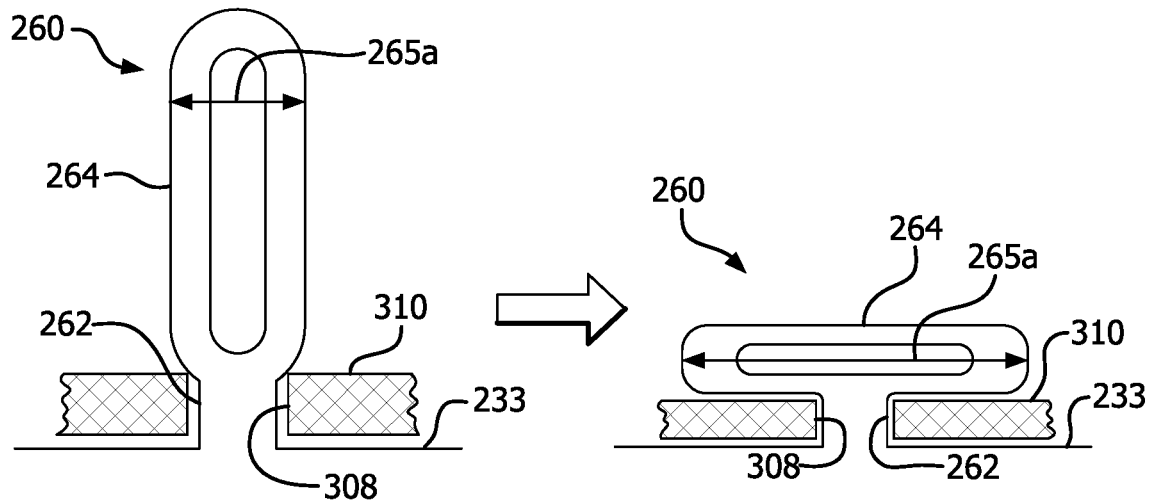
FIGS. 8A and 8B are side views of an embodiment of a leaflet frame projection.

Similarly, in the embodiment of FIGS. 8A-8B, the projection head portion 264 has a shape of an "O" having a largest projection head portion transverse dimension 265*a* that is the same or slightly larger than a dimension of the leaflet aperture 308, as shown in FIG. 8A, over which the leaflet aperture 308 may be disposed. Subsequent to disposing the leaflet aperture 308 over the projection head portion 264, the projection head portion 264 may be deformed so as to retain the leaflet 310 to the leaflet retention surface 233, as shown in FIG. 8B, essentially providing the projection head portion 264 with a largest projection head portion transverse dimension 265*a* that is larger than a dimension of the leaflet aperture 308.

Figures 9A, 9B:
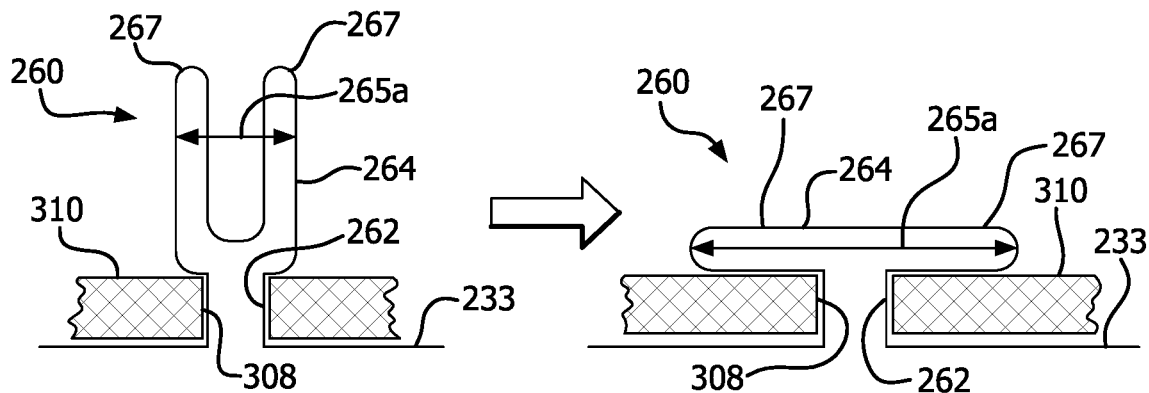
FIGS. 9A and 9B are side views of an embodiment of a leaflet frame projection.

Similarly, in the embodiment of FIGS. 9A-9B, the projection head portion 264 has a shape of two prongs 267 having a largest projection head portion transverse dimension 265*a* that is the same or slightly larger than a dimension of the leaflet aperture 308, as shown in FIG. 9A, over which the leaflet aperture 308 may be disposed. Subsequent to disposing the leaflet aperture 308 over the projection head portion 264, the two prongs 267 may be deformed away from each other and down toward the leaflet retention surface 233 so as to retain the leaflet 310 to the leaflet retention surface 233, as shown in FIG. 9B, essentially providing the projection head portion 264 with a largest projection head portion transverse dimension 265*a* that is larger than a dimension of the leaflet aperture 308.

In the embodiments of FIGS. 7A-7B through 9A-9B, the projection head portion 264 may be deformed in a number of ways. In one embodiment, the projection head portion 264 may be plastically deformed using mechanical means, such as, but not limited to, crimping. In another embodiment, the projection head portion 264 may comprise a shape memory material that may be deformed when exposed to an elevated temperature.

Figure 11A:
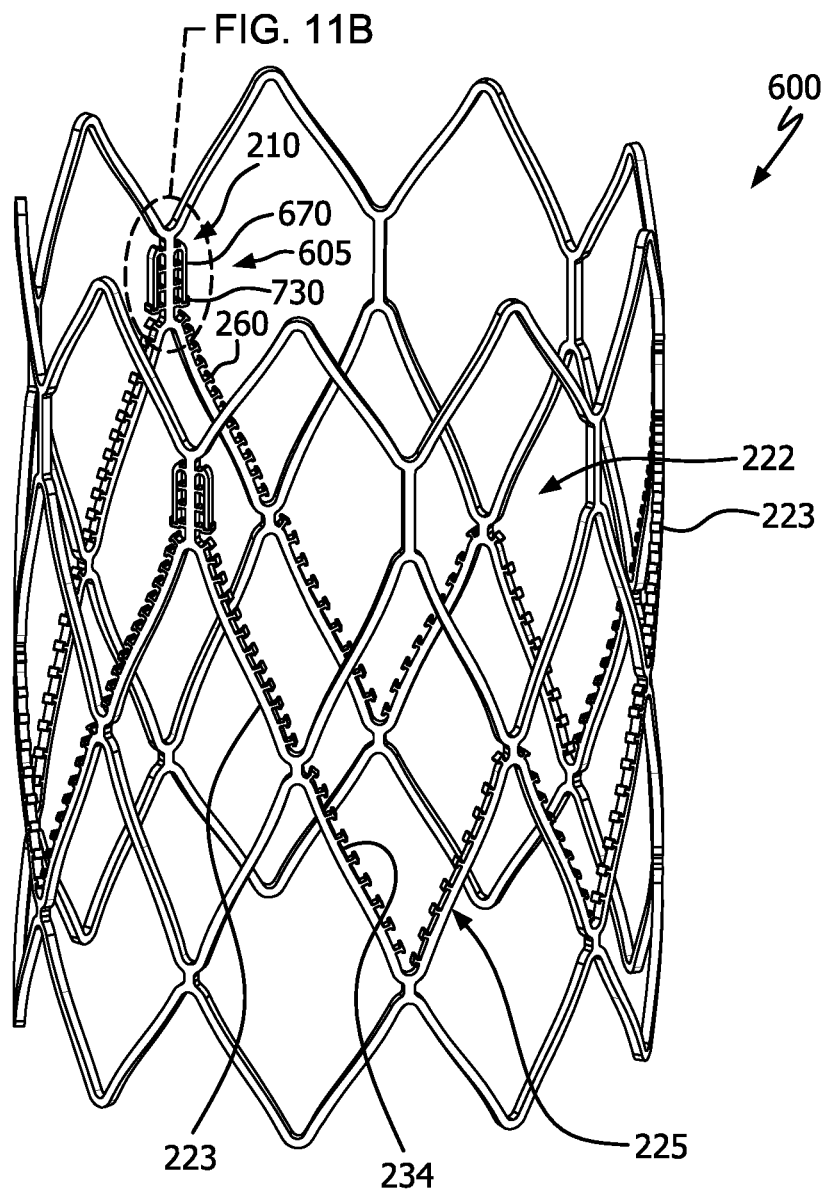
FIG. 11A is a perspective view of a leaflet frame that includes deformable locking bars and locking clips that are adjacent the leaflet frame projections, in accordance with an embodiment.

Other restraining elements can be used to impede leaflet decoupling from the leaflet frame projections 260, such as by impeding leaflet uplift away from the leaflet retentions surface. In accordance with another embodiment, FIG. 11A is a perspective view of a leaflet frame 600 that includes deformable locking bars 670 and locking clips 672 that are adjacent the leaflet frame projections 260. Each deformable locking bar 670 extends from the leaflet retention surface 233 at a bar base end 674 and is operable to extend over the projection head portion 264 of one or more adjacent leaflet frame projections 260 so as to retain the leaflet 310 onto the leaflet retention surface 233.

Figure 11B:
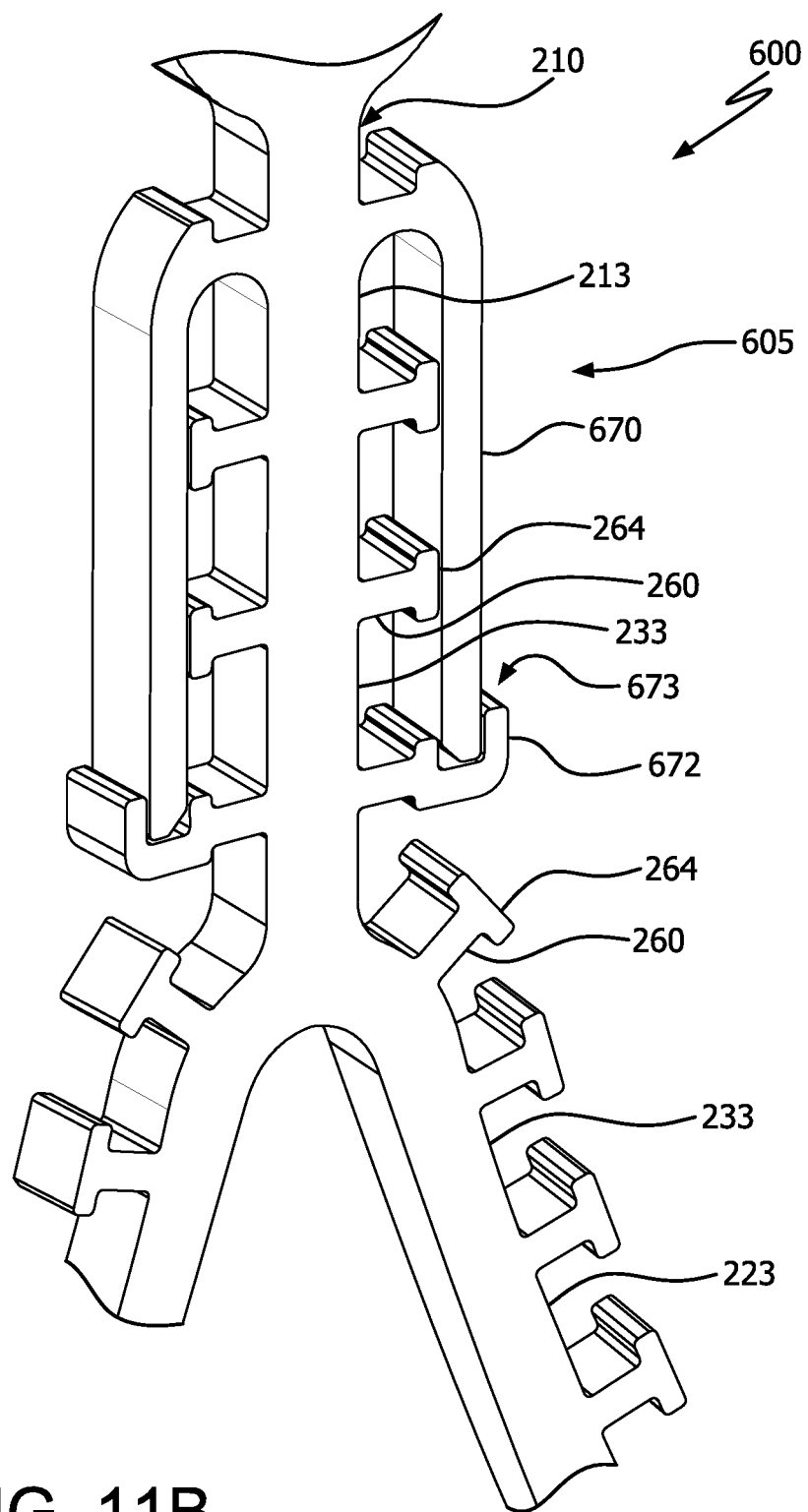
FIG. 11B is a magnified view of Box B in FIG. 11A showing a deformable locking bar restraining element in a closed position.

The leaflet frame 600 includes three leaflet windows 222 each defined by a pair of commissure posts 210, leaflet window sides 223 and a leaflet window base 225. The leaflet frame further comprises a plurality of deformable locking bar restraining elements 605 at the commissure posts 210. FIG. 11B is a magnified view of Box B in FIG. 11A showing a deformable locking bar restraining element 605 in a closed position.

It is appreciated that FIG. 11A shows a leaflet frame 600 that is operable to be used in a transcatheter procedure, wherein the leaflet frame 600 can be expanded from a smaller pre-deployment diameter to a larger deployed diameter. By way of example, FIGS. 11A and 11B show the leaflet frame 600 in the deployed state having a deployed diameter with the leaflet frame elements in a spread-apart configuration.

Figure 11C:
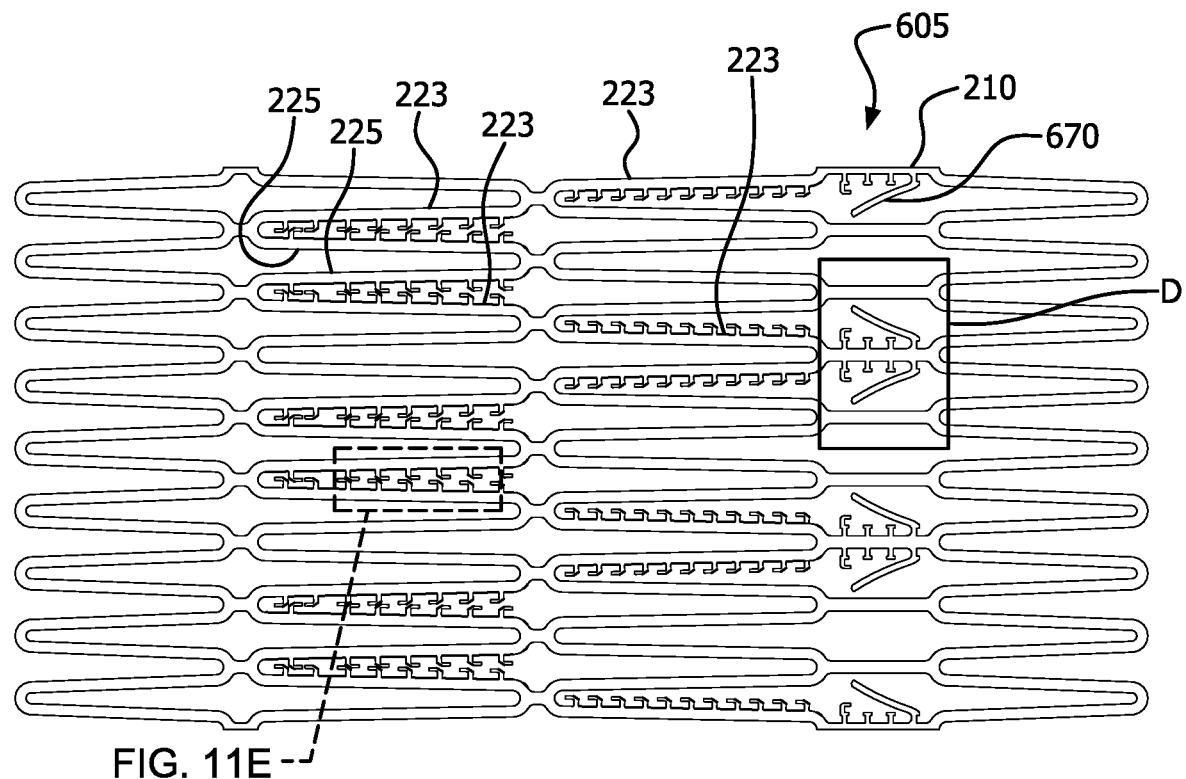
FIG. 11C is a representation of the leaflet frame shown in FIG. 11A that has been longitudinally cut, opened, and laid flat to better illustrate the elements of the leaflet frame.

FIG. 11C is a representation of the leaflet frame 600 shown in FIG. 11A that has been longitudinally cut, opened, and laid flat to better illustrate the elements of the leaflet frame 600. FIG. 11C, by way of example, shows the leaflet frame 600 in the pre-deployed state wherein the frame elements are compressed together in close proximity. FIG. 11D is a magnified view of rectangle D in FIG. 11C showing the deformable locking bar restraining element 605 in an open position. The leaflet is not shown for clarity. See Example 3 for details of leaflet attachment. The leaflet frame 600 includes leaflet frame projections 260 on the post lateral sides 213 of the commissure posts 210. Each deformable locking bar restraining element 605 includes a deformable locking bar 670 and a locking clip 672 that cooperates with the deformable locking bar 670 so as to couple the deformable locking bar 670 to the locking clip 672. The deformable locking bar includes a bar base end 674 and a bar free end 671 opposite the bar base end 674. The deformable locking bar 670 extends from the leaflet retention surface 233 at the bar base end 674. The deformable locking bar 670 has a length that spans a distance between the bar base end 674 and the locking clip 672. The locking clip 672 includes a clip groove 673 that is operable to engage the bar free end 671 so as to couple the deformable locking bar 670 to the locking clip 672. The bar base end 674 and the locking clip 672 are adjacent to and aligned with the leaflet frame projections 260 with one or more leaflet frame projections 260 therebetween. Each deformable locking bar 670 extends from the leaflet retention surface 233 on the post lateral side 213 and is operable to extend over the projection head portion 264 of the one or more leaflet frame projections 260 and couple with the locking clip 672 so as to impede decoupling of the respective leaflet from the respective leaflet frame projections whereby retaining the leaflet (not shown) onto the leaflet retention surface 233.

The bar free end 671 may engage the clip groove 673 in a number of ways. In accordance with an embodiment, the deformable locking bar 670 may be advanced out of the plane of FIG. 11D so that the bar free end 671 may be advanced over the locking clip 672 and into the clip groove 673. In another embodiment, the locking clip 672 may be resilient such that the free end 671 may deflect the locking clip 672 away from the bar free end 671 such that the bar free end 671 may snap into the clip groove 673 with the locking clip 672 resiliently returning to the pre-assembled position. In another embodiment, the bar free end 671 may be coupled to the locking clip, such as but not limited to welded, whether or not the locking clip 672 has a clip groove 673. In accordance with another embodiment, the locking clip 672 may simply be another leaflet frame projection 260 onto which the bar free end 671 is coupled, such as but not limited to welded.

Figure 11E:
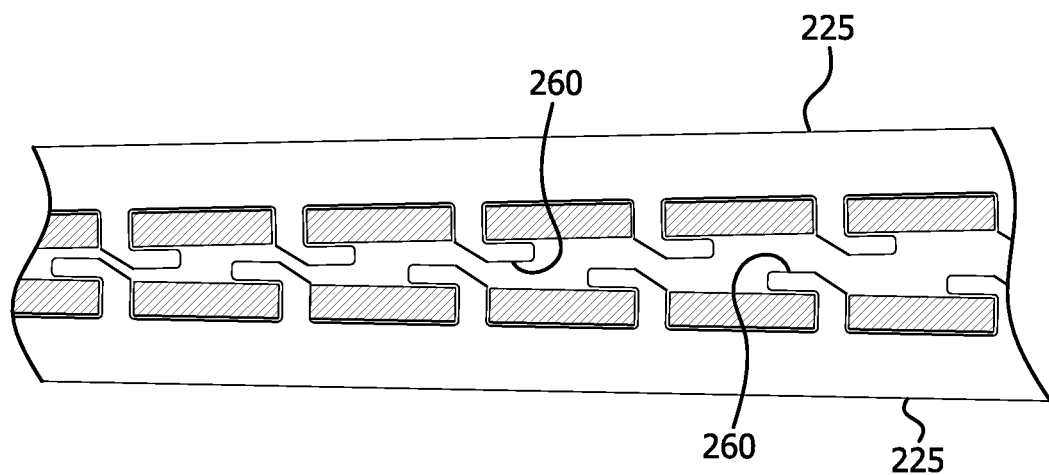
FIG. 11E is a magnified view of rectangle E in FIG. 11C showing a portion of the leaflet window base.
Figure 11D:
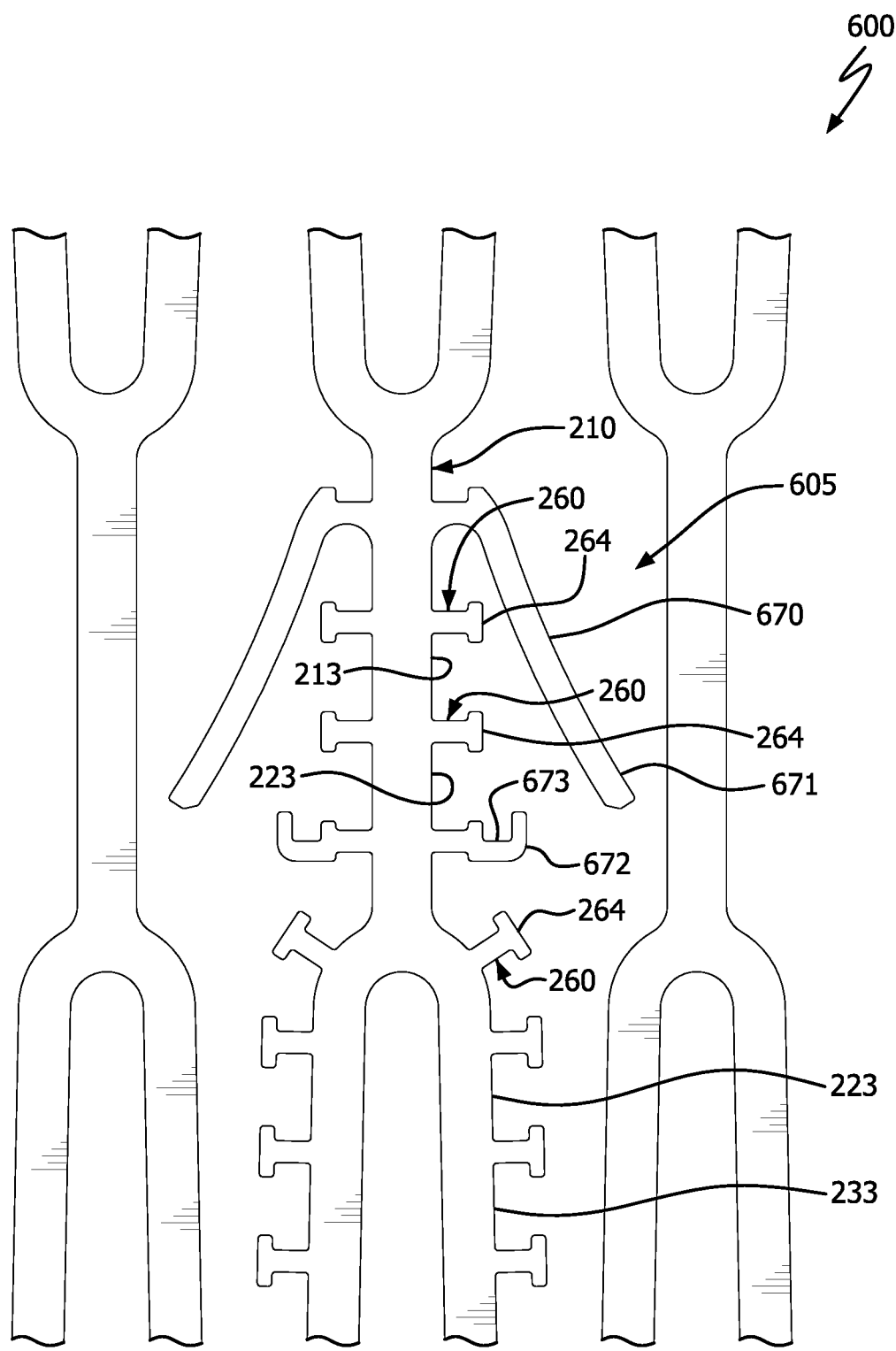
FIG. 11D is a magnified view of rectangle D in FIG. 11C showing the deformable locking bar restraining element in an open position.

FIG. 11E is a magnified view of rectangle E in FIG. 11C showing a portion of the leaflet window base 225. As can more easily be seen in FIG. 11A, the leaflet window base 225 has a V shape with an apex extending in the outflow direction. As such, as shown in the embodiment of FIG. 11E, there are leaflet frame projections 260 that, in the compressed state, oppose each other on adjacent frame elements that defines the leaflet window base 225. Opposing leaflet frame projections 260 abut each other so as to prevent further compression of the leaflet frame elements preventing the crushing of the leaflet 310. In other words, the opposing leaflet frame projections 260 act as crush stoppers. It is appreciated that in other embodiments, the leaflet frame projections 260 are in a staggered arrangement with the adjacent frame elements so as to prevent abutment of the leaflet frame projections 260 and thus allow a closer spacing of the frame elements.

It is appreciated that the deformable locking bar restraining elements 605 of FIG. 11A may be used at other locations on the leaflet retention surfaces 233. The deformable locking bar restraining elements 605 may be used on the leaflet window sides 223, the leaflet window base 225 as well as or instead of on the commissure posts 210, or any combination thereof. It is also appreciated that the deformable locking bar restraining elements 605 may be used separately or in combination with a leaflet frame projection 260 that is operable to retain the leaflet 310. In other words, the deformable locking bar restraining elements 605 may be used with the embodiments of leaflet frame projections 260 as shown in FIGS. 6A-6E, 7A-9B.

Figure 24:
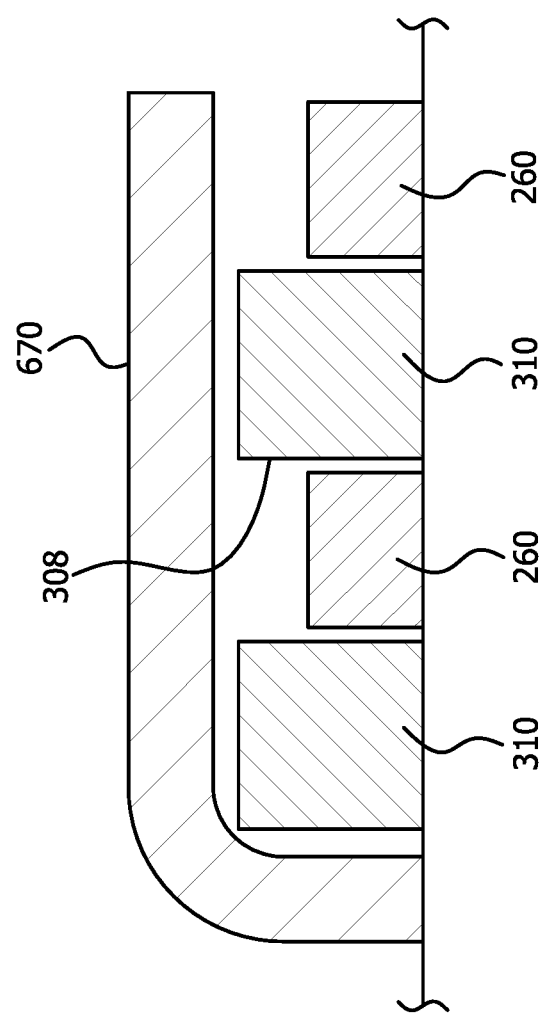
FIG. 24 is a cross sectional view of a deformable locking bar, leaflet frame projections and leaflet, in accordance with an embodiment.
Figure 25:
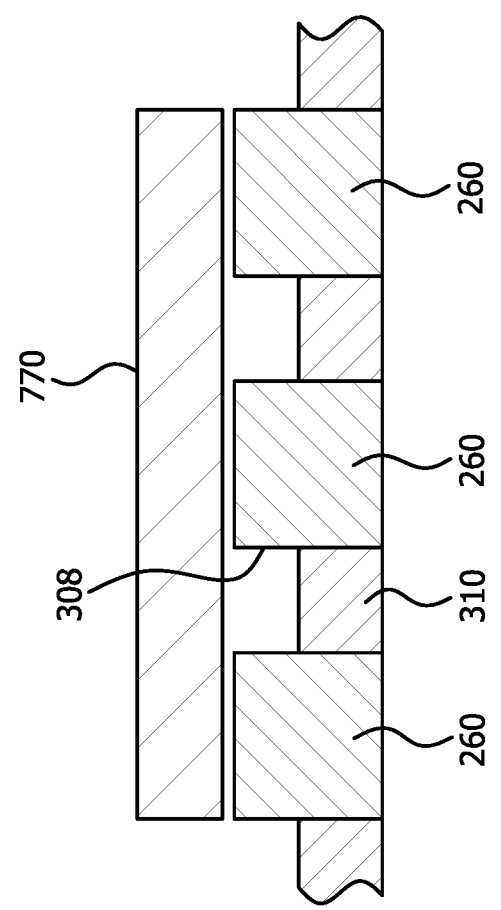
FIG. 25 is a cross sectional view of an attachable locking bar, leaflet frame projections and leaflet, in accordance with an embodiment.

FIG. 24 is a cross sectional view of a deformable locking bar 670, leaflet frame projections 260 and leaflet 310, in accordance with an embodiment. The deformable locking bar 670 is operable to extend across the leaflet frame projections 260 so as to impede leaflet 310 decoupling from the leaflet frame projections 260. It is noted that the leaflet frame projections 260 are located within a portion of the leaflet aperture 308 but do not extend through the leaflet aperture 308. In accordance with other embodiments, the leaflet frame projections 260 are located within and extend through the leaflet aperture 308.

In accordance with an embodiment, the deformable locking bar 670 and the locking clip 672 may also be leaflet frame projections, in that, the deformable locking bar 670 and the locking clip 672 may also pass through the leaflet attachment region 330.

Figure 12A:
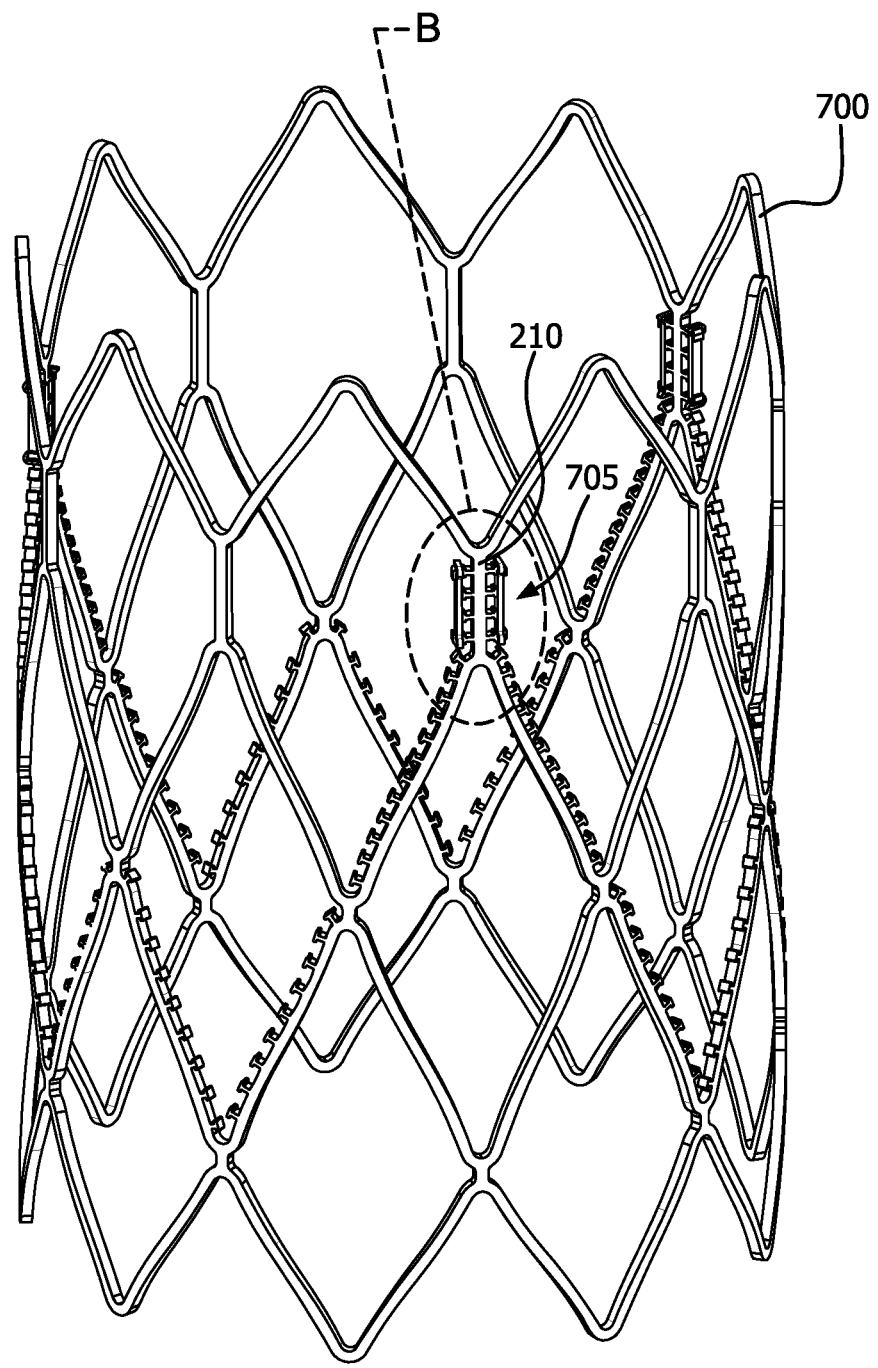
FIG. 12A is a perspective view of a leaflet frame that includes a plurality of attachable locking bar restraining elements at the commissure posts, in accordance with an embodiment.
Figure 12B:
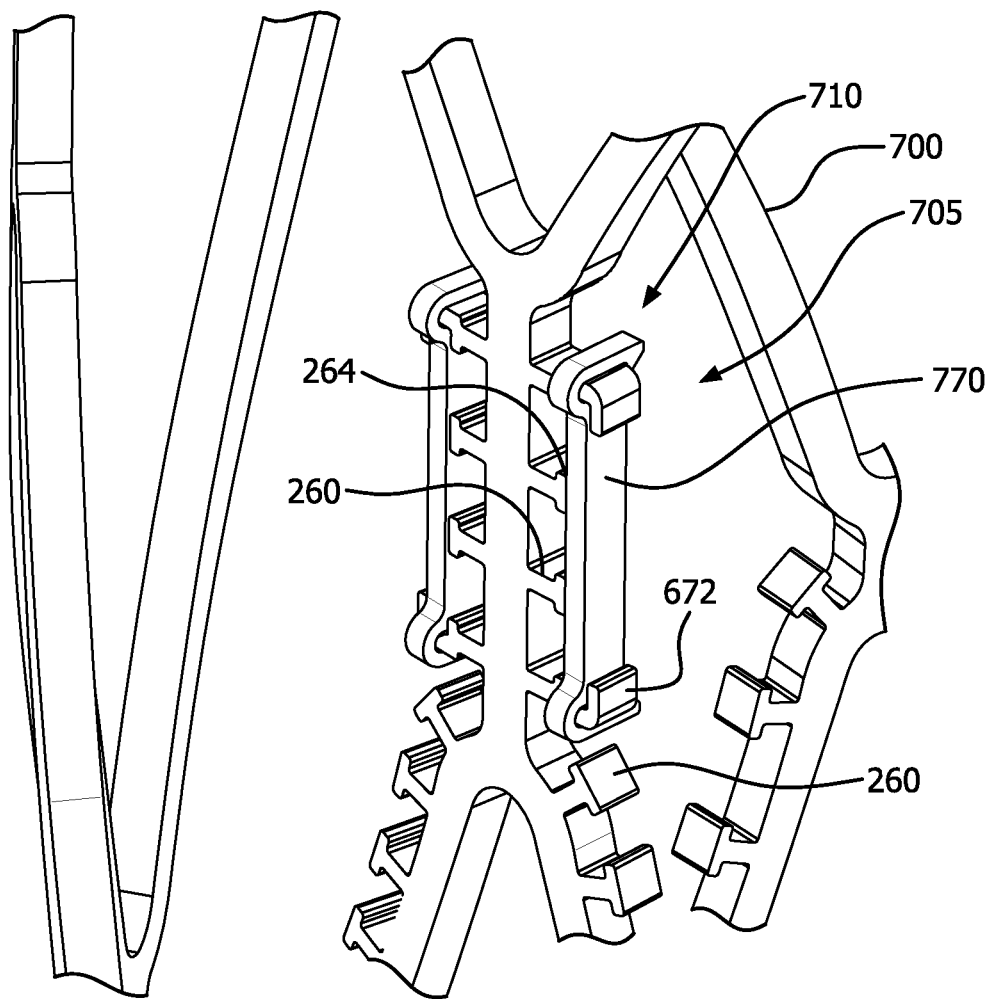
FIG. 12B is a magnified view of Box B in FIG. 12A showing the attachable locking bar restraining elements in a closed position.
Figure 12C:
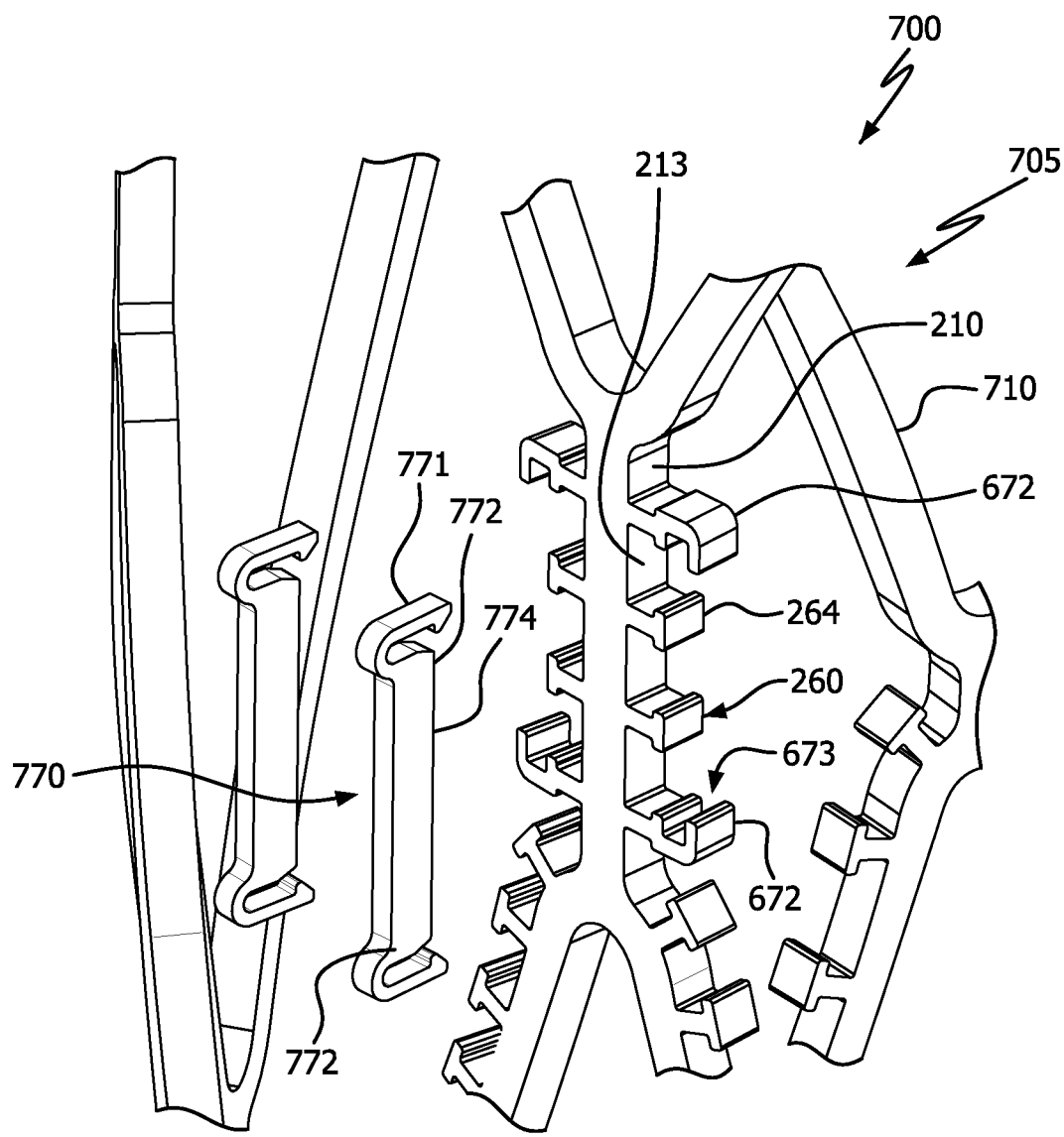
FIG. 12C is a magnified view of Box B in FIG. 12A showing an exploded view of the attachable locking bar restraining elements prior to assembly.

In accordance with another embodiment, FIG. 12A is a perspective view of a leaflet frame 700 that includes a plurality of attachable locking bar restraining elements 705 at the commissure posts 210. FIG. 12B is a magnified view of Box B in FIG. 12A showing the attachable locking bar restraining elements 705 in a closed position. FIG. 12C is a magnified view of Box B in FIG. 12A showing an exploded view of the attachable locking bar restraining elements 705 prior to assembly. The leaflet is not shown for clarity. The leaflet frame 700 includes leaflet frame projections 260 on the post lateral sides 213 of the commissure posts 210. Each attachable locking bar restraining element 705 includes an attachable locking bar 770 and a respective spaced-apart pair of locking clips 672 that cooperate with the attachable locking bar 770 so as to couple the attachable locking bar 770 to the pair of locking clips 672. The attachable locking bar 770 includes a bar-shaped element 774 with a retention hook 771 at each end. Each retention hook 771 defines a C shape. Each locking clip 672 includes a clip groove 673 that is operable to engage one of the retention hooks 771 of the attachable locking bar 770 so as to couple the attachable locking bar 770 to the pair of locking clips 672. The clip groove 673 is operable to receive and retain a portion of the bar-shaped element 774 that is adjacent the retention hook 771 therein so as to couple the deformable locking bar 770 to the locking clip 672 by capturing the locking clip 672 between the bar-shaped element 774 and the retention hook 771. The pair of locking clips 672 are adjacent to and aligned with the leaflet frame projections 260 with one or more leaflet frame projections 260 therebetween. Each locking clip 672 extends from the leaflet retention surface 233 on the post lateral sides 213. The attachable locking bar 770 has a length that spans a distance between the pair of locking clips 672. The attachable locking bar 770, when engaged with the locking clips 672, is operable to extend over the projection head portion 264 of the one or more leaflet frame projections 260 adjacent the projection head portion 264 so as to retain the leaflet (not shown) onto the leaflet retention surface 233.

The retention hooks 771 may engage the locking clips 672 in a number of ways. In accordance with an embodiment, the bar-shaped element 774 may be advanced into the clip groove 673 with the retention hook 771 advanced over the locking bar clip 672 and securely retained on the locking clip 672 by a retention flange 776. The retention hook 771 may be resilient such that the locking bar retention hook 771 may spread apart, by virtue of the C-shape, such that the retention hook 771 may snap over the locking clip 672, with the retention hook 771 resiliently returning to the pre-assembled position with the retention flange 776 retaining the retention hook 771 onto the locking clip 672. In another embodiment, the attachable locking bar 770 may be coupled to the locking clip 672, such as but not limited to welding, whether or not the locking clip 672 has a clip groove 673 and whether or not the attachable locking bar 770 has retention hooks 771. In accordance with another embodiment, the locking clip 672 may simply be another leaflet frame projection 260 onto which the attachable locking bar 770 is coupled, such as but not limited to welding, whether or not the attachable locking bar 770 includes retention hooks 771.

It is appreciated that the attachable locking bar restraining elements 705 of FIG. 12A may be used at other locations on the leaflet retention surfaces 233. The attachable locking bar restraining elements 705 may be used on the leaflet window sides 223, the leaflet window base 225 as well as or instead of on the commissure posts 210, or any combination thereof. It is also appreciated that the deformable locking bar restraining elements 605 may be used separately or in combination with a leaflet frame projection 260 that is operable to retain the leaflet 310. In other words, the deformable locking bar restraining elements 605 may be used with the embodiments of leaflet frame projections 260 as shown in FIGS. 6A-6E, 7A-9B.

In accordance with an embodiment, the locking clips 672 may also be leaflet frame projections, in that, the locking clips 672 may also pass through the leaflet attachment region 330.

It is appreciated that FIGS. 11A and 12A show leaflet frame 600 and leaflet frame 700, respectively, that are operable to be used in a transcatheter procedure, wherein the leaflet frame 600 and leaflet frame 700 will have a smaller pre-deployment diameter and a larger deployed diameter. It is understood that embodiments of leaflet frame projections 260 and restraining elements 605, 705 may be used for either surgical or transcatheter prosthetic heart valves.

As previously discussed, FIG. 11A is an outflow-side, perspective view of an embodiment of a leaflet frame 600. FIG. 11D is a representation of the leaflet frame 600 shown in FIG. 11A that has been longitudinally cut, opened, and laid flat to better illustrate the elements of the leaflet frame 600. FIG. 11E is a magnified view of rectangle E in FIG. 11C. The leaflet frame 600 defines three leaflet windows 222, each of which follow the shape of the leaflet attachment region 330 of the leaflet. The leaflet windows 222 are defined by leaflet frame internal edges 234.

Figure 13A:
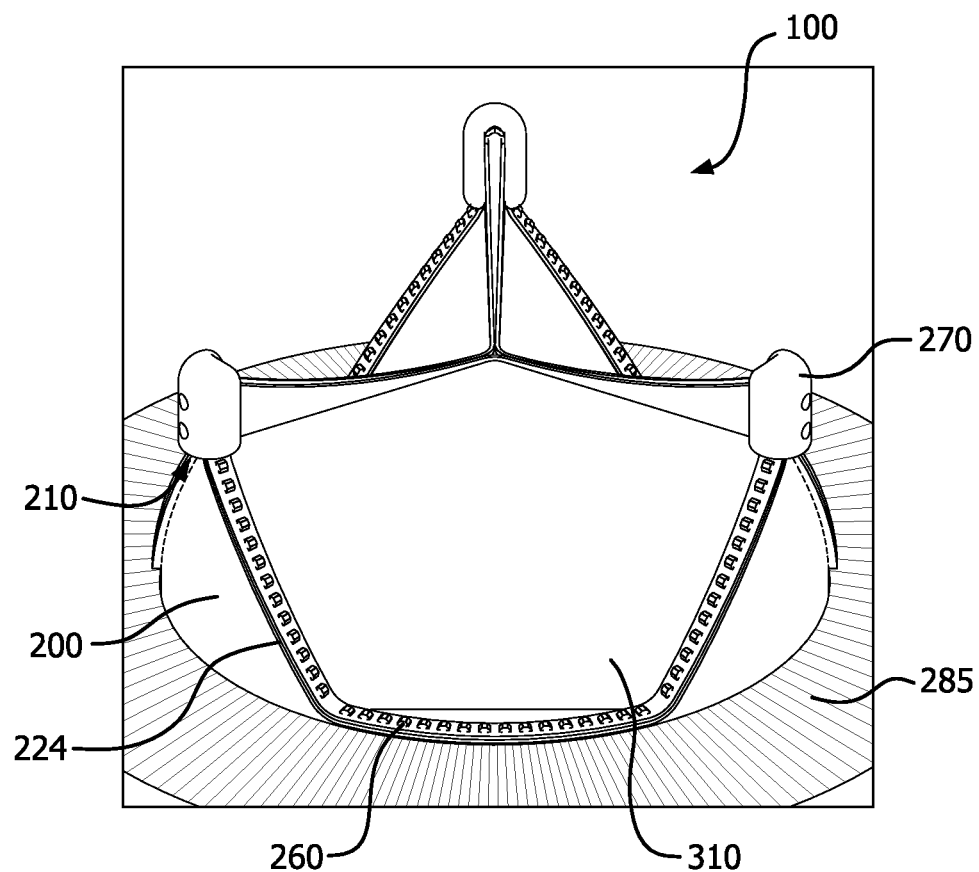
FIG. 13A is an outflow-side, perspective view of a prosthetic valve in accordance with an embodiment comprising a sewing cuff and commissure post caps.
Figure 13B:
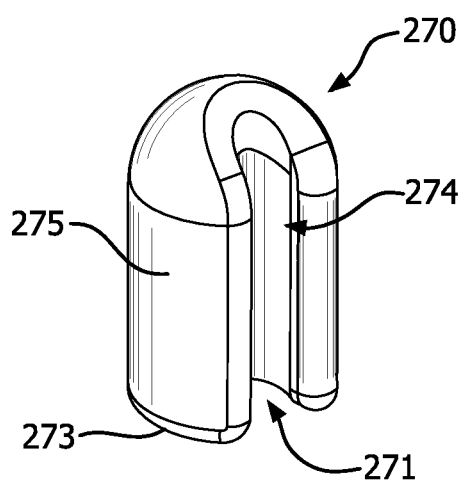
FIG. 13B is a perspective view of a commissure post cap embodiment shown in FIG. 13A.

Other restraining elements can be used to impede leaflet decoupling from the leaflet frame projections 260, such as by impeding leaflet uplift away from the leaflet retentions surface. FIG. 13A is an outflow perspective view of a prosthetic valve 100, in accordance with an embodiment, shown in a closed configuration. The components of the prosthetic valve 100 observed in FIG. 13A comprise the leaflet frame 200, the plurality of leaflets 310, a sewing cuff 285, and a commissure post cap 270 disposed on each commissure post 210. FIG. 13B is a perspective view of the commissure post cap 270 shown in FIG. 1D. For example, with specific reference to FIGS. 13A and 13B, the prosthetic valve 100 can comprise a commissure post cap 270 disposed over each commissure post 210. Each commissure post cap 270 can define an interior cavity 271 that is open at a cap end 273 and can be configured to receive a commissure post 210 in the interior cavity 271. The commissure post cap 270 further defines a sidewall slot 274 in the sidewall 275 of the commissure post cap 270 that is open at the cap end 272 and is configured to receive two leaflet free edges 312. The commissure post cap 270 can be coupled to the leaflet frame 200 by a mechanical attachment, by an adhesive, or through thermal bonding. The commissure post cap 270 is a restraining element that can be used to impede leaflet 310 decoupling from the leaflet frame projections 260 that are on the commissure post 210, such as by impeding leaflet 310 uplift away from the leaflet retention surface 233. Although the embodiment of FIG. 13B is of a surgical prosthetic valve, the commissure post cap 270 may also be used for a transcatheter prosthetic valve.

Alternatively, with reference to FIG. 5, a restraining element can be a leaflet frame jacket 290. The leaflet frame jacket 290 defines an annular ring and can be shaped so that a portion of it extends along the leaflet frame second edge 224 (e.g., a lip 291 shaped to cover the projection tip 266) and is coupleable to the leaflet frame 200. When coupled to the leaflet frame 200, the leaflets 310 are impeded from being decoupled from the leaflet frame projections 260. In addition, in various embodiments, the inner side of the lip 291 can have a rounded edge to minimize abrasion on the leaflet 310 during use.

In the embodiment shown in FIG. 5, the leaflet frame jacket 290 comprises an upper jacket portion 290a and a lower jacket portion 290b that together define an annular form and are shaped to encase the leaflet frame 200. The upper jacket portion 290a comprises a lip 291 that projects inward toward valve orifice 101. The lip 291 defines one or more recesses 292 (e.g., a plurality of apertures) on the lip surface 293 that faces the leaflet frame second edge 224 when assembled. The recesses 292 can be dimensioned to receive one or more projection tips 266. The lower jacket portion 290b is coupleable to the upper jacket portion 290a so as to encase the leaflet frame 200 at the leaflet frame outer surface 204, leaflet frame first edge 227, and leaflet frame second edge 224 but not the leaflet frame inner surface 202. The lower jacket portion 290b comprises one or more attachment features that are configured to couple with one or more attachment feature on the upper jacket portion 290a. In the embodiment shown, the lower jacket portion 290b comprises a plurality of clips 295 that are extendible into a circumferential recess (not shown) in the inner surface 294 of the upper jacket portion 290a. The upper jacket portion 290a and lower jacket portion 290b may be coupled together by pressing together, which causes a resilient deformation of the clips 295, to affect engagement.

The leaflet frame 200 can be etched, cut, laser cut, stamped, three-dimensional printed, among other suitable processes, into an annular structure or a sheet of material, with the sheet then formed into an annular structure. The leaflet frame shape can be configured for transcatheter or surgical devices.

The leaflet frame 200 can comprise any rigid or semi-rigid biocompatible material. Materials suitable for the leaflet frame 200 include, but not limited to, titanium alloys, stainless steel, cobalt-nickel alloy, polypropylene, acetyl homopolymer, acetyl copolymer, other alloys or polymers, or any other material that is generally biocompatible having adequate physical and mechanical properties to function as the leaflet frame 200 as described herein. In some embodiments, the leaflet frame 200 can be a shape-memory material, such as nitinol, a nickel-titanium alloy.

FIGS. 2A and 2B are a perspective view and a side view, respectively, of the leaflet frame 200 that defines an annular shape, in accordance with another embodiment. This embodiment is similar to the embodiment described above and shown in FIG. 1A, except that the portions of leaflet frame 200 below the commissure posts 210 are a continuous wall instead of an opening, such as the triangular opening 256. Sewing cuff attachment apertures 280 are provided near the leaflet frame first edge 227 below the commissure post 210. Similarly, a plurality of leaflet frame projections 260 that are spaced apart and project from the leaflet frame second edge 224, namely at the leaflet window sides 223, the leaflet window base 225, and the post lateral sides 213. Unlike the embodiment of FIG. 1A, the projection head portion 264 defines an overhang on both lateral sides of the projection head portion 264 instead of one.

Figure 3A:
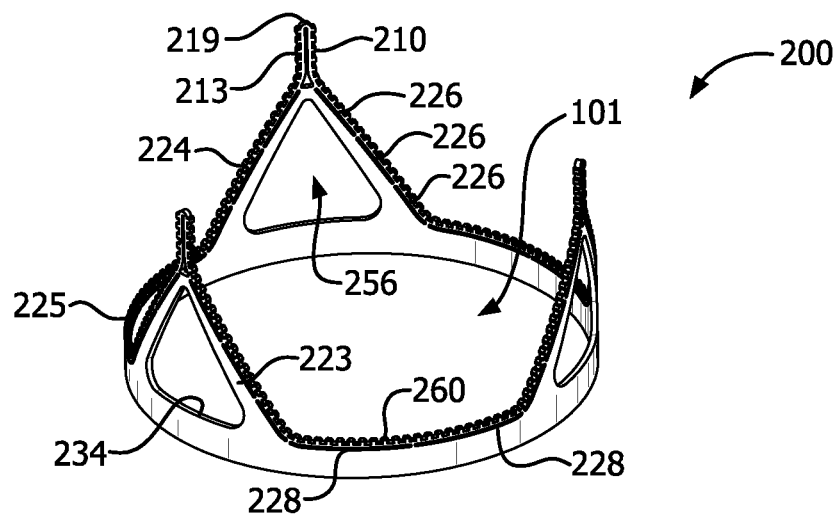
FIG. 3A is an outflow-side, perspective view of a leaflet frame in accordance with an embodiment.
Figure 3B:
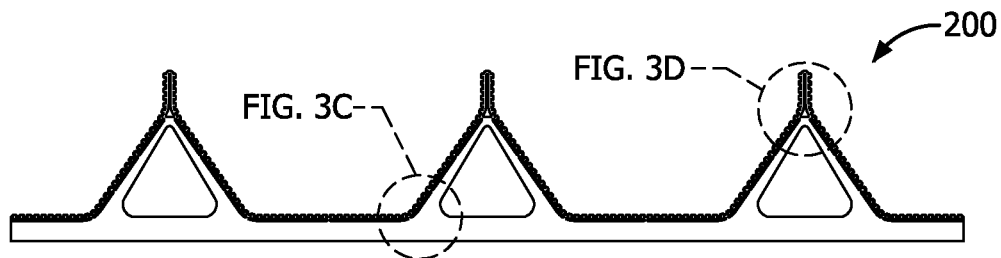
FIG. 3B is a representation of the leaflet frame shown in FIG. 3A that has been unrolled to a flat orientation.
Figures 3C, 3D:
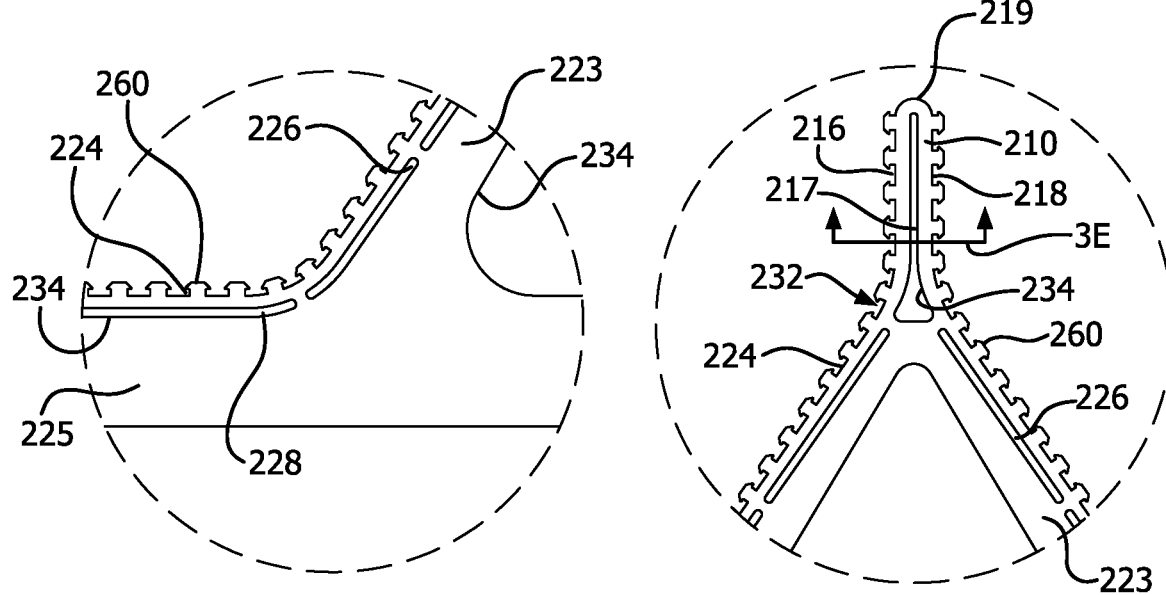
FIG. 3C is a magnified view of circle 3C in FIG. 3B.
FIG. 3D is a magnified view of circle 3D in FIG. 3B.

FIG. 3A is an outflow-side, perspective view of a leaflet frame 200 in accordance with yet another embodiment. FIG. 3B is a representation of the leaflet frame shown in FIG. 3A that has been longitudinally cut, opened, and laid flat to better illustrate the elements of the leaflet frame 200. FIG. 3C is a magnified view of circle 3C in FIG. 3B. FIG. 3D is a magnified view of circle 3D in FIG. 3B. Similar to the embodiment shown in FIG. 1A, the leaflet frame 200 defines three leaflet windows 222, each of which follow the shape of the leaflet attachment region 330. However, in the embodiment shown, the leaflet windows 222 are defined by leaflet frame internal edges 234 which define leaflet frame slots (e.g., post slot 217, side receiving slot 226, and base receiving slots 228 described below). The leaflet window 222 is defined by two commissure posts 210, two leaflet window sides 223, and a leaflet window base 225 extending between the two leaflet window sides. The leaflet window sides 223 and the leaflet window base 225 together define three sides of an arced isosceles trapezoid. A plurality of spaced apart leaflet frame projections 260 are spaced apart and project from the leaflet frame second edge 224 at the leaflet window sides 223, the leaflet window base 225, and the post lateral sides 213.

Figure 3E:
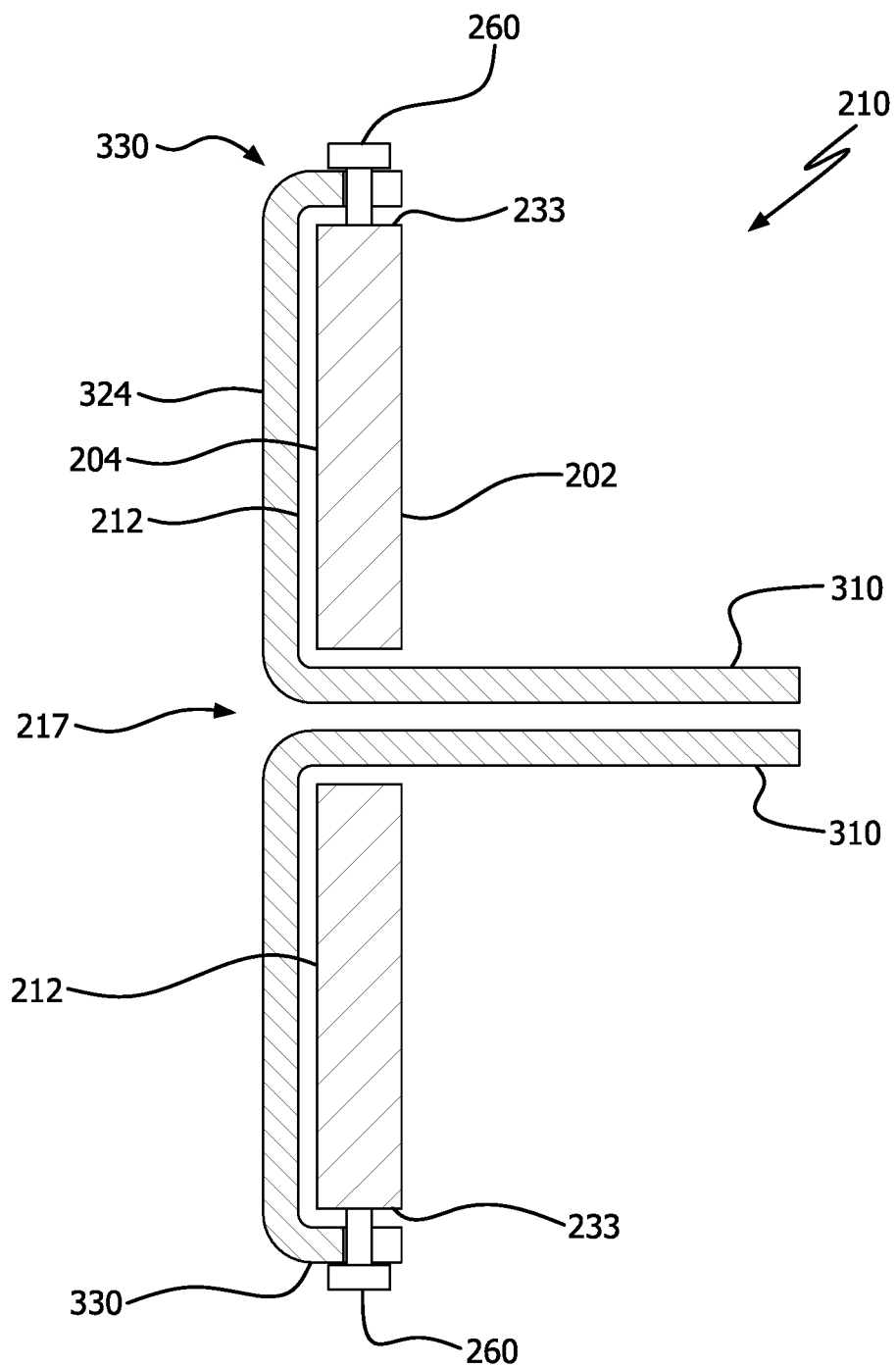
FIG. 3E is a cross-sectional view of FIG. 3D, along line 3E, of the commissure post showing a fold-over portion of the leaflet.

As described later in reference to FIG. 14, a leaflet attachment region 330 of each leaflet 310 is the portion that is passed through the respective post slot 217, side receiving slot 226, and base receiving slots 228 and is used to secure the leaflet 310 to the two commissure posts 210, the two leaflet window sides 223, and the leaflet window base 225 of the leaflet frame 200 with the fold-over portion 324 of the leaflet base 325 wrapping partially around the leaflet frame outer surface 204 of the respective leaflet frame elements: the commissure posts 210, the leaflet window sides 223, and the leaflet window base 225. FIG. 3E is a cross-sectional view of FIG. 3D, along line 3E, of the commissure post 210 showing a fold-over portion 324 of the leaflet 310, also refer to FIG. 14, passing through the post slot 217 from the leaflet frame inner surface 202, and wrapped along the leaflet frame outer surface 204 with the leaflet attachment region 330 advanced over the leaflet frame projections 260 to be received on the leaflet retention surface 233. In an assembled prosthetic valve, the leaflet attachment region 330 would be coupled to the leaflet window base 225 each of the two leaflet window sides 223 and the commissure posts 210, facilitated by the leaflet frame projections 260.

The commissure posts 210 are equally spaced from one another around the leaflet frame 200 between two adjacent leaflet windows 222. The portion of the leaflet frame 200 disposed under each commissure post 210 and between adjacent leaflet windows 222 is an open triangular frame defined by the leaflet frame internal edges 234 of neighboring leaflet window sides 223 and the leaflet frame base 221.

Each commissure post 210 defines a post slot 217 therethrough that is oriented lengthwise to be substantially parallel with the central longitudinal axis A-B. More particularly, the commissure post 210 is defined by a first post leg 216 and a second post leg 218 separated by the post slot 217 therebetween. The first post leg 216 and the second post leg 218 converge to form a commissure tip 219. The neighboring leaflet window sides 223 meet at the base of the commissure post 210. The post slot 217 can be dimensioned to have a width that accommodates the thickness of one or two leaflets 310, and the length that accommodates the length of the leaflet attachment region 330 that is coupleable to the commissure post 210. A portion of the leaflet attachment region 330 that is adjacent to the leaflet free edge 312 extends through a post slot 217, specifically, the post slot 217 adjacent to it, such that two leaflets extend through each post slot 217.

Each leaflet window side 223 defines one or more side receiving slots 226 therethrough that are oriented to substantially align lengthwise with the leaflet frame second edge 224 at leaflet window side 223. Similarly, each leaflet window base 225 defines one or more base receiving slots 228 therethrough that are oriented to substantially align lengthwise with the leaflet frame second edge 224 at leaflet window base 225. The side receiving slots 226 and the base receiving slots 228 are dimensioned to accommodate the thickness of the leaflet 310, and in the embodiment shown, have a length that is close to but slightly less than that of leaflet window side 223 and leaflet window base 225, respectively. It is understood that various embodiments may define a plurality of side receiving slots 226 and/or a plurality of base receiving slots 228 oriented end-to-end to extend the approximate length of leaflet window side 223 or leaflet window base 225.

Figure 4B:
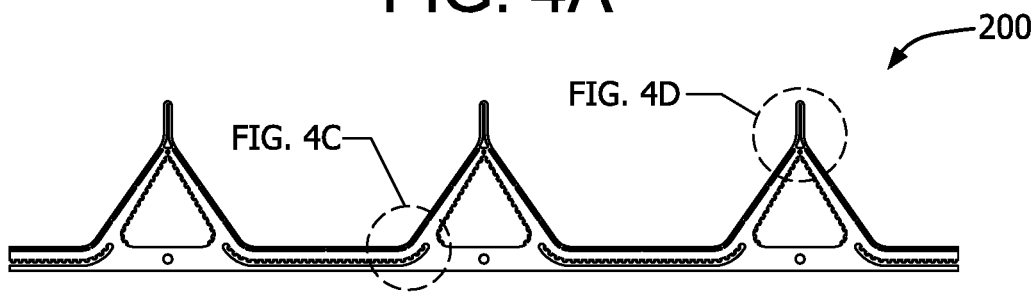
FIG. 4B is a representation of the leaflet frame shown in FIG. 4A that has been unrolled to a flat orientation.
Figures 4C, 4D:
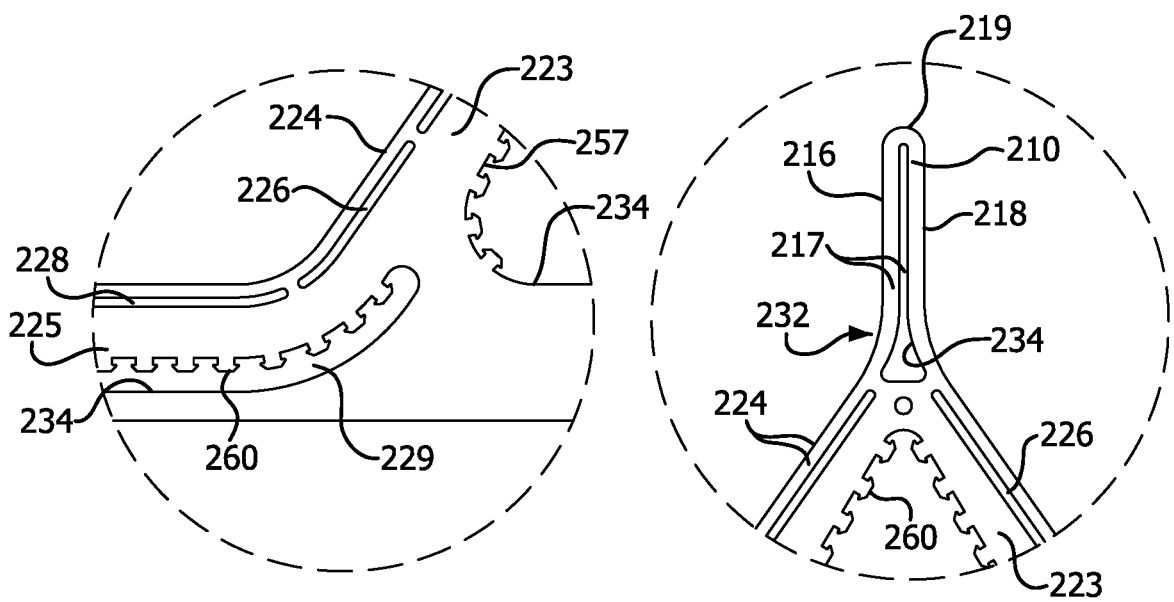
FIG. 4C is a magnified view of circle 4C in FIG. 4B.
FIG. 4D is a magnified view of circle 4D in FIG. 4B.

FIG. 4A is an outflow-side, perspective view of a leaflet frame 200 in accordance with yet another embodiment. FIG. 4B is a representation of the leaflet frame shown in FIG. 4A that has been longitudinally cut, opened, and laid flat to better illustrate the elements of the leaflet frame 200. FIG. 4C is a magnified view of circle 4C in FIG. 4B. FIG. 4D is a magnified view of circle 4D in FIG. 4B. This embodiment is the same as the embodiment described above and shown in FIG. 3A, except that the leaflet frame projections 260 are located on a leaflet frame internal edge 234 of leaflet frame 200 and the leaflet frame projections 260 are not on the commissures posts 210.

Similar to the embodiment shown in FIG. 3A, the leaflet frame 200 defines three leaflet windows 222, each of which follow the shape of the leaflet 310. Each leaflet window 222 is defined by two commissure posts 210, two leaflet window sides 223, and a leaflet window base 225 extending between the two leaflet window sides. The leaflet window sides and the leaflet window base 225 together define three sides of an arced isosceles trapezoid. The commissure posts 210 are equally spaced from one another around the leaflet frame 200 between two adjacent leaflet windows 222. The portion of leaflet frame 200 disposed under each commissure post 210 and between the adjacent leaflet windows 222 is a triangular opening 256 defined by the leaflet frame internal edges 234 of neighboring leaflet window sides 223 and the leaflet frame base 221.

Each commissure post 210 defines a post slot 217 therethrough that is oriented lengthwise to be substantially parallel to the axis A-B. More particularly, the commissure post 210 is defined by the first post leg 216 and the second post leg 218 separated by the post slot 217 therebetween. The first post leg 216 and the second post leg 218 converge to form the commissure tip 219. The neighboring leaflet window sides 223 converge at the apex 232 which is the commissure post base of the commissure post 210. The post slot 217 can be dimensioned to have a width that accommodates the thickness of one or two leaflets 310 at the leaflet attachment region 330 and the length to accommodate the length of the leaflet attachment region 330 that couples to the commissure post 210.

Each leaflet window side 223 defines one or more side receiving slots 226 therethrough that are oriented to substantially align lengthwise with the leaflet frame second edge 224 at the leaflet window side 223. Similarly, each leaflet window base 225 defines one or more base receiving slots 228 therethrough that are oriented to substantially align lengthwise with the leaflet frame second edge 224 at the leaflet window base 225. The side receiving slots 226 and the base receiving slot 228 are dimensioned to accommodate the thickness of the leaflet 310, and in the embodiment shown, have a length that is close to but slightly less than that of the corresponding leaflet window side 223 and leaflet window base 225, respectively. It is understood that various embodiments may define a plurality of the side receiving slots 226 and/or a plurality of the base receiving slot 228 oriented end-to-end to extend the approximate length of the leaflet window side 223 or the leaflet window base 225, respectively.

Unlike the embodiment of FIG. 3A, the leaflet window base 225 defines a second slot, specifically, a leaflet attachment slot 229, that is also oriented to substantially align lengthwise with the leaflet frame second edge 224 at the leaflet window base 225. The base receiving slot 228 is disposed between the leaflet attachment slot 229 and the leaflet frame second edge 224. A plurality of the leaflet frame projections 260 are spaced apart and project from the attachment slot internal edge 230 defining the leaflet attachment slot 229. In addition, the leaflet frame projections 260 are located on the side internal edge 257 adjacent to the leaflet window side 223 that partially defines a triangular opening 256. In the embodiment shown, no leaflet frame projections 260 are located on the commissure posts 210, although in other embodiments, there are leaflet frame projections 260 on the commissure posts 210, such as the embodiment of FIG. 3A.

As described later in reference to FIG. 14, a leaflet attachment region 330 of each leaflet 310 is the portion that is passed through the respective post slot 217, side receiving slot 226, and base receiving slots 228 and is used to secure the leaflet 310 to the two commissure posts 210, the two leaflet window sides 223, and the leaflet window base 225 of the leaflet frame 200 with the fold-over portion 324 wrapping partially around the respective leaflet frame elements: the commissure posts 210, the leaflet window sides 223, and the leaflet window base 225. In an assembled prosthetic valve, the leaflet attachment region 330 would be coupled to the leaflet window base 225 and each of the two leaflet window sides 223 facilitated by the leaflet frame projections 260.

In various embodiments, the leaflet frame 200 can be configured to couple to the leaflets 310 in a manner which distributes the load to portions of the leaflet attachment region 330 that are not disposed adjacent the leaflet retention surface 233. Stated differently, it reduces stress concentrations within the leaflet attachment region 330 as compared with the configuration shown in FIG. 1. Such force distribution can be facilitated by the leaflet attachment region 330 being wrapped around the respective leaflet frame elements, namely, the leaflet window sides 223, the leaflet window base 225, and the post lateral sides 213. For example, this is facilitated by the leaflet passing through the respective post slot 217, side receiving slot 226, and base receiving slots 228 and is used to secure the leaflet 310 to the two commissure posts 210, the two leaflet window sides 223, and the leaflet window base 225 of the leaflet frame 200 with the fold-over portion 324 wrapping partially around the respective leaflet frame elements: the commissure posts 210, the leaflet window sides 223, and the leaflet window base 225. Also, the force distribution can be facilitated by increasing the distance between the leaflet aperture 308 and the leaflet base 325, which is the intersection between the leaflet attachment region 330 and the leaflet belly region 322.

While the depicted embodiments all show a leaflet window in the shape of an isosceles trapezoid, it is understood that the leaflet frame elements can be configured to define other leaflet window shapes. In particular, in some embodiments, the two leaflet window sides and leaflet window base therebetween can together define a parabolic curve. Also, while the depicted embodiments all show commissure posts that are equally spaced around the leaflet frame, it is understood that the commissure posts can be unequally spaced. Similarly, while the depicted embodiments all show only three leaflets, it is understood that prosthetic valves and valved conduits of the present disclosure can have more or less than three leaflets, such as 2, 4, or 5.

In various embodiments, the leaflet frame 200 can be wrapped with a material, such as an ePTFE membrane, suitable for promoting tissue in-growth. All surfaces of the leaflet frame can be wrapped with a film prior to leaflet attachment. Alternatively, a polyethylene terephthalate fabric (e.g., Dacron fabric) suitable for promoting tissue ingrowth could be coupled to the leaflet frame inner surface and the leaflet frame outer surface of the leaflet frame and optionally between the leaflet frame projections prior to leaflet attachment.

Leaflet

Each leaflet window 222 is provided with one of the leaflets 310 that are coupleable to the leaflet frame 200 at one or more leaflet retention surfaces 233 of the leaflet window sides 223, the leaflet window base 225, and/or the commissure posts 210, as shown in FIG. 1A. The leaflets 310 extend radially inward from the leaflet frame 200 when coupled to the leaflet frame 200. The leaflet 310, in accordance with the present disclosure, is configured to couple to the leaflet frame 200 by way of a plurality of leaflet apertures 308 located in the leaflet attachment region 330 that are each configured to receive a leaflet frame projection 260. Each leaflet 310 defines a leaflet attachment region 330, a leaflet belly region 322, and a leaflet free edge 312; the leaflet belly region 322 terminates at the leaflet free edge 312. The leaflet base 325 refers to the intersection between the leaflet attachment region 330 and the leaflet belly region 322.

In accordance with an embodiment, the leaflet attachment region 330 is coupleable to the leaflet frame 200 at the commissure post 210, the leaflet window side 223 and the leaflet window base 225. More particularly, the leaflet attachment region 330 defines a plurality of leaflet apertures 308 that are configured to each receive a leaflet frame projection 260, like the embodiment shown in FIG. 1A. As previously described, in various embodiments, the shape and dimensions of the leaflet aperture 308 can be substantially the same as the shape and dimensions of the projection base portion 262.

The leaflet 310 can be reinforced about one or more leaflet apertures 308. A reinforcement can be, for example, a leaflet attachment region 330 comprising a thickened portion of leaflet material that defines the leaflet aperture 308. For example, the reinforcement can be a reinforcement strip 332 that is added to the leaflet 310 in the leaflet attachment region 330 and defines the leaflet apertures 308. In another example, the reinforcement can be a folded over portion to provide a double or triple, or more, layers of leaflet material and defines the leaflet apertures 308. In various embodiments, the reinforcement strip 332 can comprise leaflet material, that is, the same material as the leaflet 310. When coupled to the leaflet frame 200, the reinforcement strip 332 can be located on a leaflet first side 311 of the leaflet 310 that is facing the leaflet retention surface 233, or alternatively it can be on a leaflet second side 313 that is opposite from the leaflet first side 311, or alternatively, it can be on both the leaflet first side 311 and the leaflet second side 313.

In accordance with an embodiment, when the leaflets 310 are in a fully open position, the prosthetic valve 100 presents a valve orifice 101 that is substantially circular. Fluid flow is permitted through the valve orifice 101 when the leaflets 310 are in the open position. In the open position, it can be said that each leaflet 310 is extended from the leaflet frame inner surface 202 at an angle of greater than 45 degrees. When the prosthetic valve 100 is closed, generally about half of each leaflet free edge 312 abuts an adjacent half of a leaflet free edge 312 of an adjacent leaflet 310, as shown in FIG. 1C. The three leaflets 310 of the embodiment of FIG. 1A meet or nearly meet at a triple point 348. The valve orifice 101 is occluded when the leaflets 310 are in the closed position stopping fluid flow. In the closed position, it can be said that each leaflet 310 is extended substantially perpendicular from a leaflet frame inner surface. The leaflets 310 exhibit a bias toward the closed position by virtue of the leaflet 310 extending from the leaflet frame inner surface 202 substantially normal to the central longitudinal axis A-B of the leaflet frame 200 which defines the central longitudinal axis of the prosthetic valve 100. This is beneficial in that the leaflets 310 will tend to close earlier during the phase of the cardiac cycle where the blood is decelerating or reversing. An earlier closure will tend to reduce back flow through the prosthetic valve 100.

The shape of each leaflet 310 when coupled to the leaflet is determined in part by the shape of the leaflet contact edge of the leaflet frame elements defining the leaflet window 222, in particular, the commissure posts 210, the two leaflet window sides 223, and the leaflet window base 225, as well as the shape of the leaflet attachment region 330 and the leaflet free edge 312. FIG. 10A shows a top view of the leaflet 310, as used in the prosthetic valve 100 of FIG. 1A, in a flat configuration. This view shows that the leaflet 310, at the leaflet attachment region 330, has substantially the shape of an isosceles trapezoid with bowed sides. The degree of bowing can correspond to the arc of the leaflet frame 200 at the two leaflet window sides 223 and the leaflet window base 225, respectively. Also, this view shows that the leaflet free edge 312 has a scallop-like shape with an apex at the center flanked on each side by a generally concave edge that is straight near the apex. By modifying the geometries and dimensions of this flat pattern, three-dimensional shape of a leaflet 310 can be altered. Of course, while not necessarily required, the shape of the leaflets 310 can also be influenced by other techniques, such as, but not limited to, leaflet molding and shape-setting.

Figure 14:
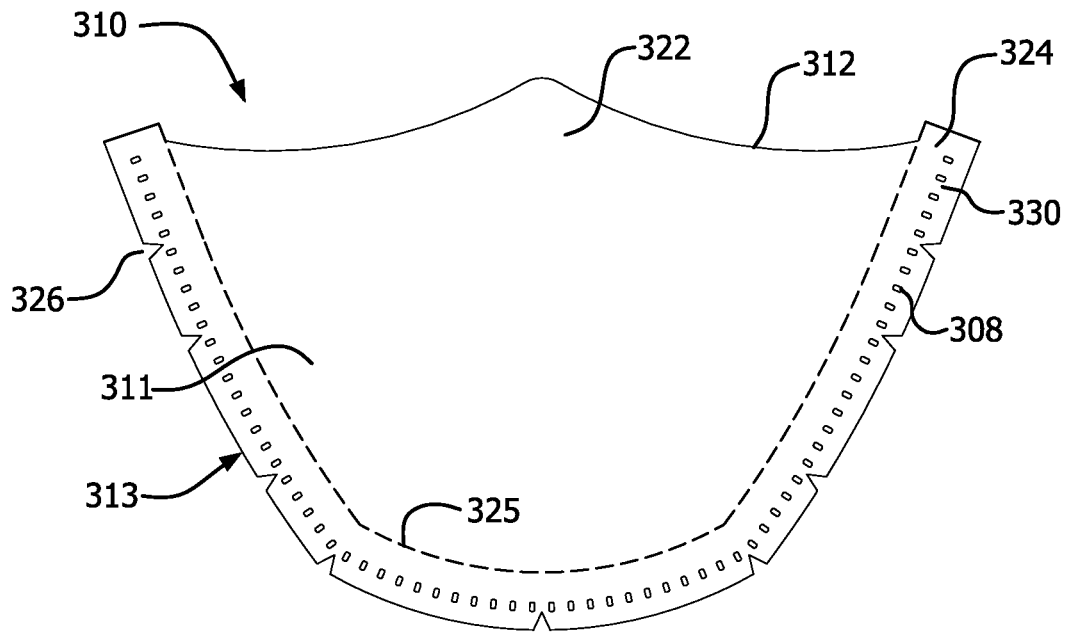
FIG. 14 is a top view of a leaflet in accordance with an embodiment that is coupleable to a leaflet frame embodiment similar to that shown in FIG. 3A.

FIG. 14 depicts an embodiment of a leaflet 310 configured for use with the embodiment of the leaflet frame 200 that is shown in FIGS. 3A-3E. The leaflet 310 has a leaflet belly region 322 and a leaflet attachment region 330 defining a plurality of leaflet apertures 308 and having a fold-over portion 324 that is adjacent to the leaflet base 325. The leaflet 310 can be configured to wrap around a portion of the following frame elements: the commissure posts 210, the leaflet window sides 223, and the leaflet window base 225.

The leaflet belly region 322 of each leaflet 310 is the operating portion of the leaflet 310 when assembled into a finished prosthetic valve 100. The leaflet attachment region 330 of each leaflet 310 is the portion that is used to secure the leaflet 310 to the two commissure posts 210, the two leaflet window sides 223, and the leaflet window base 225 of the leaflet frame 200 with the fold-over portion 324 wrapping partially around the respective leaflet frame elements: the commissure posts 210, the leaflet window sides 223, and the leaflet window base 225. To facilitate wrapping around the respective leaflet frame elements, the leaflet attachment region 330 can define a plurality of notches 326. A notch 326 can be located on the leaflet 310 such that when coupled to the leaflet frame 200, the notch 326 is at an intersection between two leaflet frame elements, namely, an intersection between the commissure posts 210 and the leaflet window sides 223, or the leaflet window side 223 and the leaflet window base 225. A notch 326 can also be located on the leaflet such that when coupled to the leaflet frame 200, the notch 326 is between two side receiving slots 226 or between two base receiving slots 228.

When coupled to the leaflet frame 200 of FIGS. 3A-3E, the post slot 217, the side receiving slots 226, and the base receiving slot 228 each receive respective portions of the leaflet attachment region 330. The fold-over portion 324 is disposed within the post slot 217, as shown in FIG. 3E, side receiving slots 226, and the base receiving slot 228, and wrapped around a post outer side 212 of the commissure posts 210, the leaflet window sides 223, and the leaflet window base 225. The leaflet attachment region 330 that defines the leaflet apertures 308 is seated on the leaflet frame second edge 224 such that each leaflet aperture 308 is disposed about a corresponding leaflet frame projection 260 on the leaflet retention surface 233, in this case, the leaflet frame second edge 224. Two of the fold-over portions 324 of neighboring leaflets 310 come together in each of the post slots 217 so that the leaflet free edge 312 can come together or coapt in the valve orifice 101 of the prosthetic valve 100 to close the prosthetic valve 100, without the slight gap 317 formed as the leaflets pass around the outside of the commissure post, as shown in FIGS. 1C and 3E.

Figure 15:
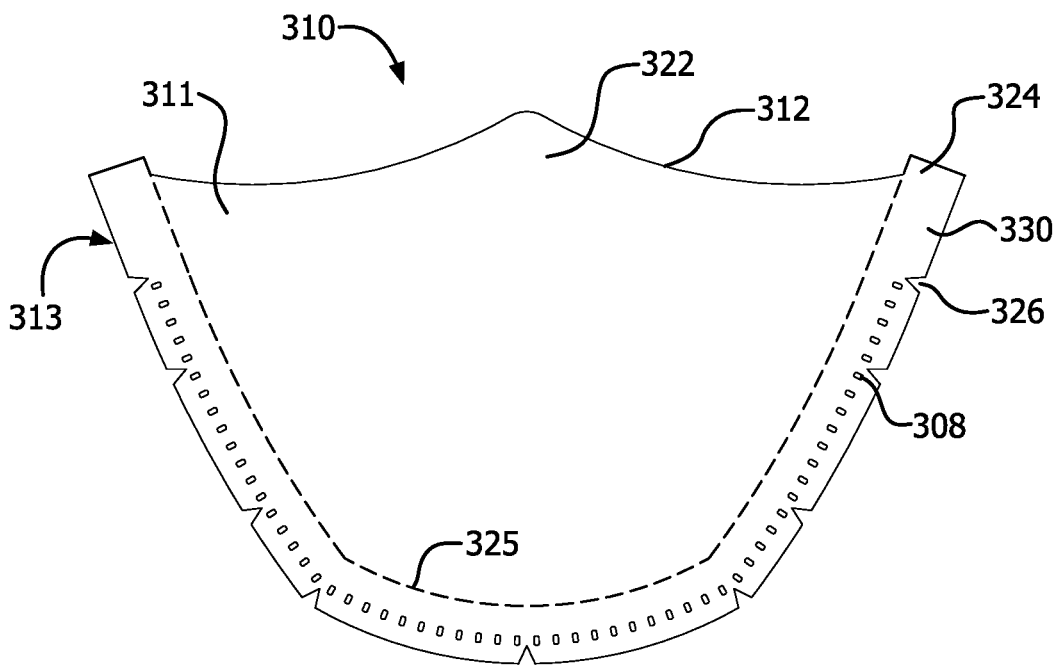
FIG. 15 is a top view of a leaflet in accordance with an embodiment that is coupleable to a leaflet frame embodiment similar to that shown in FIG. 4A.

FIG. 14 depicts an embodiment of the leaflet 310 configured for use with the embodiment of the leaflet frame 200 as shown in FIG. 4A. Similar to the embodiment that is shown in FIG. 14, the leaflet 310 has a leaflet belly region 322 and a leaflet attachment region 330 defining a plurality of leaflet apertures 308 and having a fold-over portion 324 that is adjacent to the leaflet base 325, but it is different from that of FIG. 14 in that the embodiment shown in FIG. 15 is configured only to wrap around the following frame elements: the leaflet window sides 223 and the leaflet window base 225. Thus, no apertures are located in the section of the leaflet attachment region 330 intended to couple to the commissure posts 210. The leaflet belly region 322 of each leaflet 310 is the operating portion of the leaflet 310 when in a finished prosthetic valve 100. The leaflet attachment region 330 of each leaflet 310 is the portion that is used to secure the leaflet 310 to the two commissure posts 210, two leaflet window sides 223 and the leaflet window base 225 of the leaflet frame 200. To facilitate wrapping around the respective leaflet window sides 223 and the leaflet window base 225, and extending into the post slot 217, the attachment region can define a plurality of notches 326. A notch 326 can be located on the leaflet 310 such that when coupled to the leaflet frame 200, it is at an intersection between two leaflet frame elements, namely, an intersection between the commissure posts 210 and the leaflet window sides 223 or the leaflet window side 223 and the leaflet window base 225.

When coupled to the leaflet frame 200 of FIG. 4A, the post slot 217, the side receiving slots 226, and the base receiving slot 228 each receive the respective portions of the leaflet attachment region 330. The fold-over portion 324 is disposed within the post slot 217, side receiving slots 226, and the base receiving slot 228, and wrapped around a leaflet frame outer surface 204 of the leaflet window sides 223 and the leaflet window base 225. The portion of the leaflet attachment region 330 that defines the leaflet apertures 308 is disposed adjacent a leaflet frame internal edge 234 of the respective leaflet frame elements with each leaflet aperture 308 being disposed about a corresponding leaflet frame projection 260. In this case, by way of example, the leaflet frame internal edges 234 that operate as the leaflet retention surfaces 233 can include the side internal edge 257 and the attachment slot internal edge 230.

The fold-over portion 324 that corresponds to the commissure post 210 is extendible through the post slot 217 and can be fixed at the commissure post 210, such as by an adhesive agent and/or the above-described commissure post cap. Two fold-over portions 324 of neighboring leaflets 310 come together in each post slot 217 so that the leaflet free edge 312 can come together or coapt in the valve orifice 101 of the prosthetic valve 100 to close the prosthetic valve 100 in a manner similar to that shown in FIG. 1A.

Leaflet Material

The leaflet 310 can be made of a polymer or biological tissue. More particularly, the leaflet 310 can also be made from a sheet of polymer material or biological tissue that has been cut into a shape with the leaflet apertures 308 like that shown in FIGS. 7-9. The leaflet 310 can become "shaped" upon attachment to the leaflet frame 200. Pre-shaped polymer leaflets can also be made by starting from a cylinder of polymer material that has been cut into a shape like that shown in FIGS. 7-9 with the leaflet apertures 308. A reinforcement strip 332 can also be bonded to the polymer material or biological material and the leaflet apertures 308 can be cut into both the leaflet 310 and reinforcement strip 332 simultaneously.

The leaflet 310 can comprise any biocompatible material sufficiently compliant and flexible, such as a biocompatible polymer and biological tissue. In various embodiments, the leaflet 310 can comprise a material that is synthetic or of animal origin. The leaflet 310 can comprise a membrane that is combined with an elastomer to form a composite material. The leaflet 310 can comprise, according to an embodiment, a composite material comprising an expanded fluoropolymer membrane that comprises a plurality of spaces within a matrix of fibrils, and an elastomeric material. It should be appreciated that multiple types of fluoropolymer membranes and multiple types of elastomeric materials can be combined to form a composite material while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure, such as pores, for achieving the desired leaflet performance. Other biocompatible polymers that can be suitable for use in the leaflet 310 include but are not limited to the groups of urethanes, silicones (organopolysiloxanes), copolymers of silicon-urethane, styrene/isobutylene copolymers, polyisobutylene, polyethylene copoly(vinyl acetate), polyester copolymers, nylon copolymers, fluorinated hydrocarbon polymers and copolymers or mixtures of each of the foregoing.

Further examples of leaflet materials include: wherein the leaflet 310 comprises at least one fluoropolymer membrane layer; wherein the leaflet 310 comprises a laminate having more than one fluoropolymer membrane layer; wherein the at least one fluoropolymer membrane layer is an expanded fluoropolymer membrane layer; wherein an elastomer is contained within the expanded fluoropolymer membrane layer; wherein the elastomer comprises perfluoromethyl vinyl ether and tetrafluoroethylene; wherein the expanded fluoropolymer membrane layer comprises ePTFE; wherein the leaflet 310 comprises a composite material having at least one fluoropolymer membrane layer having a plurality of pores and an elastomer present in the pores of at least one of the fluoropolymer membrane layers; wherein the composite material comprises fluoropolymer membrane by weight in a range of about 10% to 90%; wherein the elastomer comprises (per)fluoroalkylvinylethers (PAVE); wherein the elastomer comprises a copolymer of tetrafluoroethylene and perfluoromethyl vinyl ether; wherein the elastomer is silicone; wherein the elastomer is a fluoroelastomer; wherein the elastomer is a urethane; and wherein the elastomer is a TFE/PMVE copolymer; wherein the TFE/PMVE copolymer comprises essentially of between about 40 and 80 weight percent perfluoromethyl vinyl ether and complementally 60 and 20 weight percent tetrafluoroethylene; and wherein the leaflet 310 comprises silicone.

Subcomponent

Figure 16A:
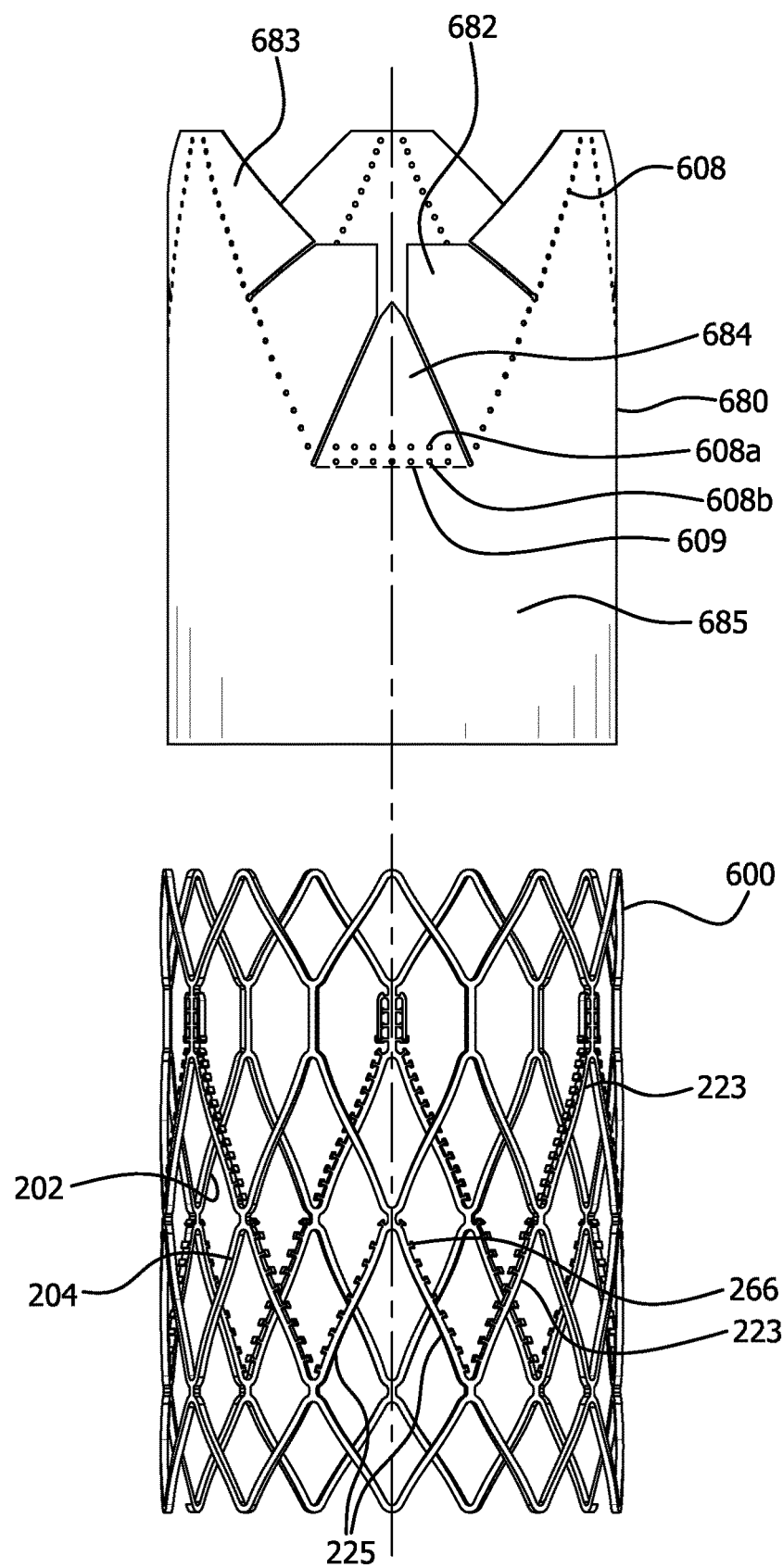
FIG. 16A is an exploded view of the leaflet frame of the embodiment of FIG. 12A, and a subcomponent, in accordance with an embodiment.

In accordance with embodiments, the leaflet frame projections may be used to couple other components onto the leaflet frame. FIG. 16A is an exploded view of the leaflet frame 600 of the embodiment of FIG. 12A, and a subcomponent 680, in accordance with an embodiment. By way of example, as also presented in Example 3, the leaflet frame 600 of FIG. 12A is provided with a skirt 685 which is part of the subcomponent 680 which is coupled to the leaflet frame 600 via the leaflet frame projections 260. By way of example, the skirt 685 provides a blood barrier to the leaflet inflow side B of the prosthetic valve 160, shown in FIG. 23, and as discussed in Example 3. It is understood that the subcomponent 680 may also or instead be disposed on the leaflet outflow side A of the prosthetic valve 160.

The subcomponent 680 includes subcomponent apertures 608 arranged to correspond to the leaflet frame projections 260 along the leaflet window sides 223 and, in some embodiments, the leaflet window base 225. The subcomponent 680, further includes a first row of sewing apertures 608*a* and a second row of sewing apertures 608*b*, which are parallel, that will be used to sew a portion of the leaflet base to the subcomponent. This is an example of an additional use of the subcomponent wherein other elements of the prosthetic valve, in this embodiment the leaflet base, may be attached, in this embodiment by way of sewing, to the subcomponent 680, and thus to the leaflet frame 600.

Figure 16B:
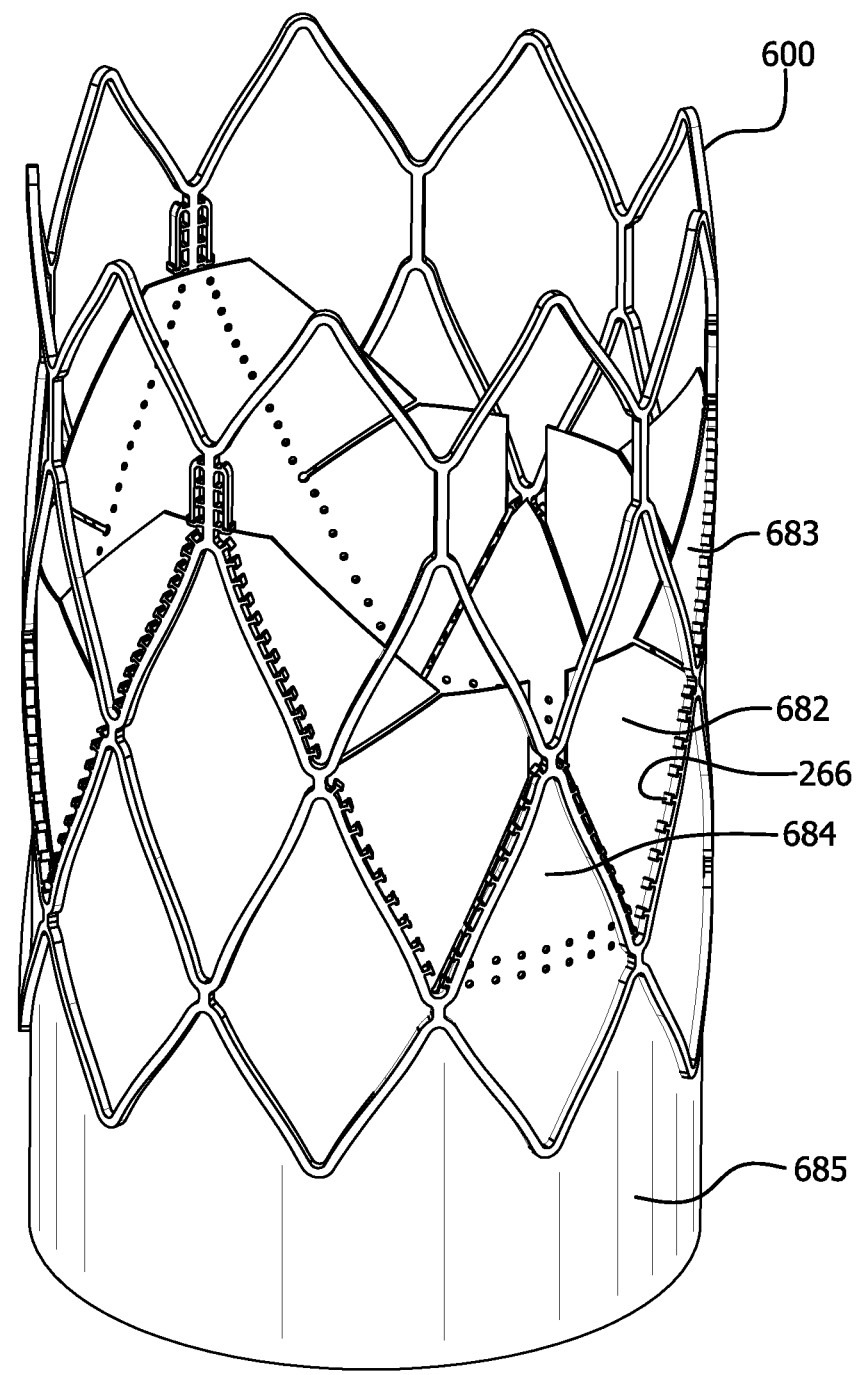
FIG. 16B is a perspective view of the subcomponent disposed within the leaflet frame of the embodiment of FIG. 16A, in accordance with an embodiment.
Figure 16C:
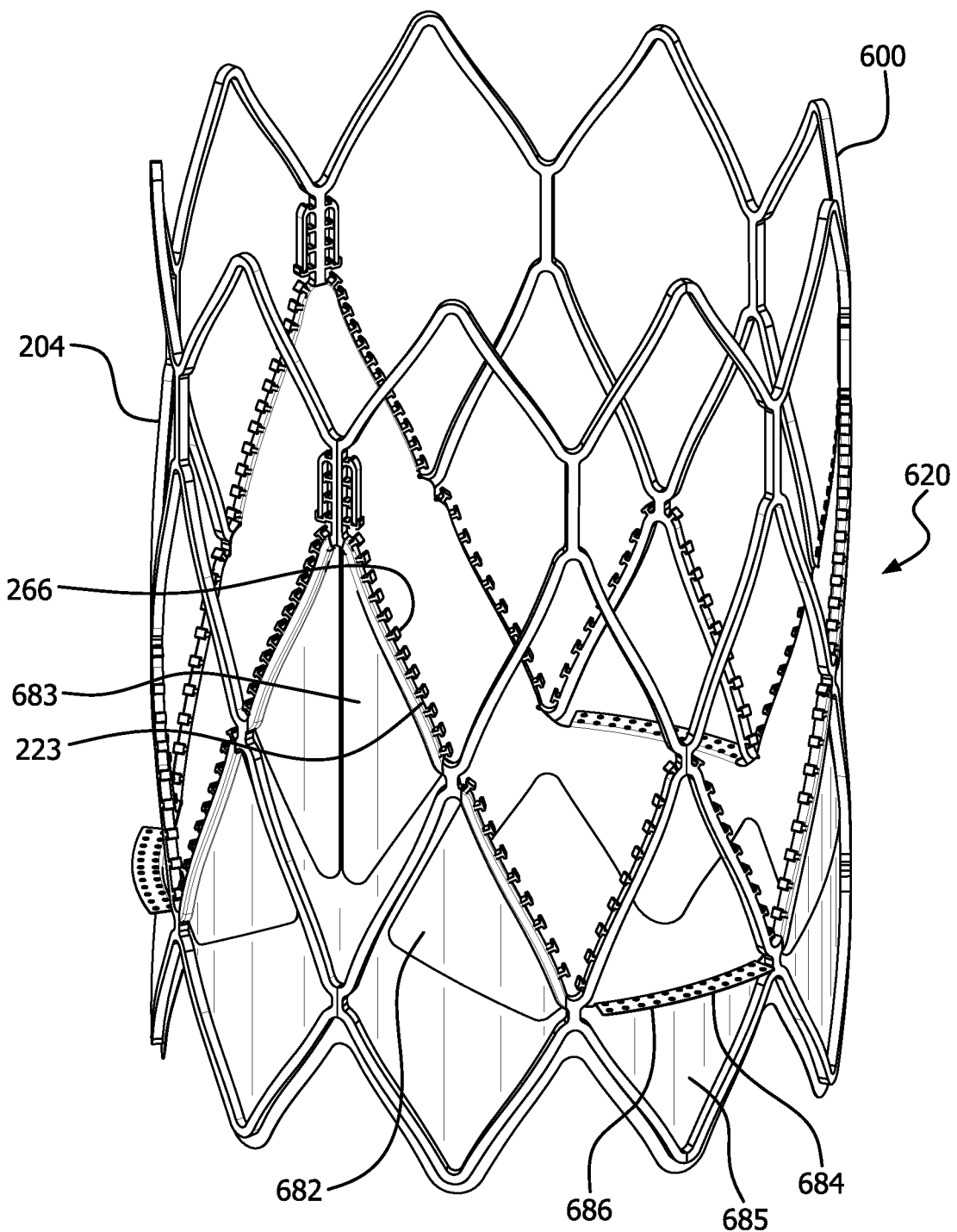
FIG. 16C is a perspective view of the subcomponent disposed within the leaflet frame of the embodiment of FIG. 16A, in accordance with an embodiment.

The subcomponent apertures 608 defines a portion of the subcomponent 680 that is the skirt 685 as well as first fold-over portions 683, second fold-over portions 682, and third fold-over portions 684. The third fold-over portions 684 are defined by the first row of sewing apertures 608*a* and the second row of sewing apertures 608*b*. As will also be described in Example 3, the subcomponent 680 is disposed within the leaflet frame 600, as shown in FIG. 16B, such that the skirt 685 is adjacent the leaflet frame inner surface 202, the subcomponent apertures 608 disposed over respective leaflet frame projections 260. FIG. 16C is a perspective view of the embodiment of FIG. 16B wherein the first fold-over portions 683 and second fold-over portions 682 folded over the leaflet window sides 223 and disposed adjacent the leaflet frame outer surface 204 and subsequently bonded to the skirt 685, effectively coupling the subcomponent 680 to the leaflet frame 600. The third fold-over portions 684 are folded about a fold line 609 adjacent the first row of sewing apertures 608*a* and trimmed to form a subcomponent flange 686 that includes the first row of sewing apertures 608*a* and the second row of sewing apertures 608*b* such that they may receive suture therethrough during a leaflet base attachment process. In an alternative embodiment, the third fold-over portions 684 may be folded about a fold line that is between the first row of sewing apertures 608*a* and the second row of sewing apertures 608*b* aligning the first row of sewing apertures 608*a* with the second row of sewing apertures 608*b* such that they may receive suture therethrough during a leaflet base attachment process. This produces a double thickness of the leaflet material at the portion of the leaflet base that is sewn to the subcomponent 680.

Transcatheter Prosthetic Valve

Figure 17:
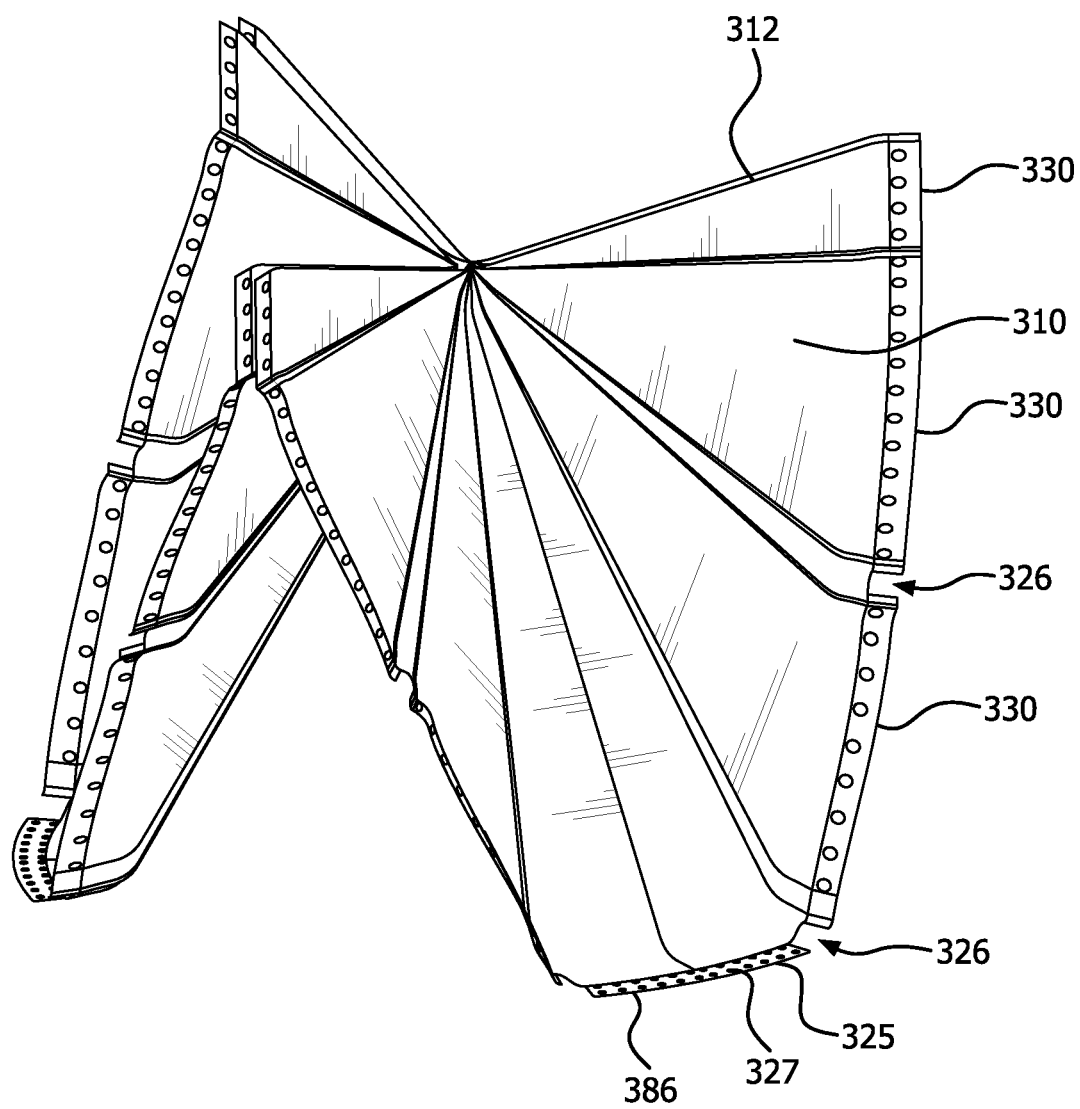
FIG. 17 is a perspective view of three leaflets, in accordance with an embodiment.
Figure 18A:
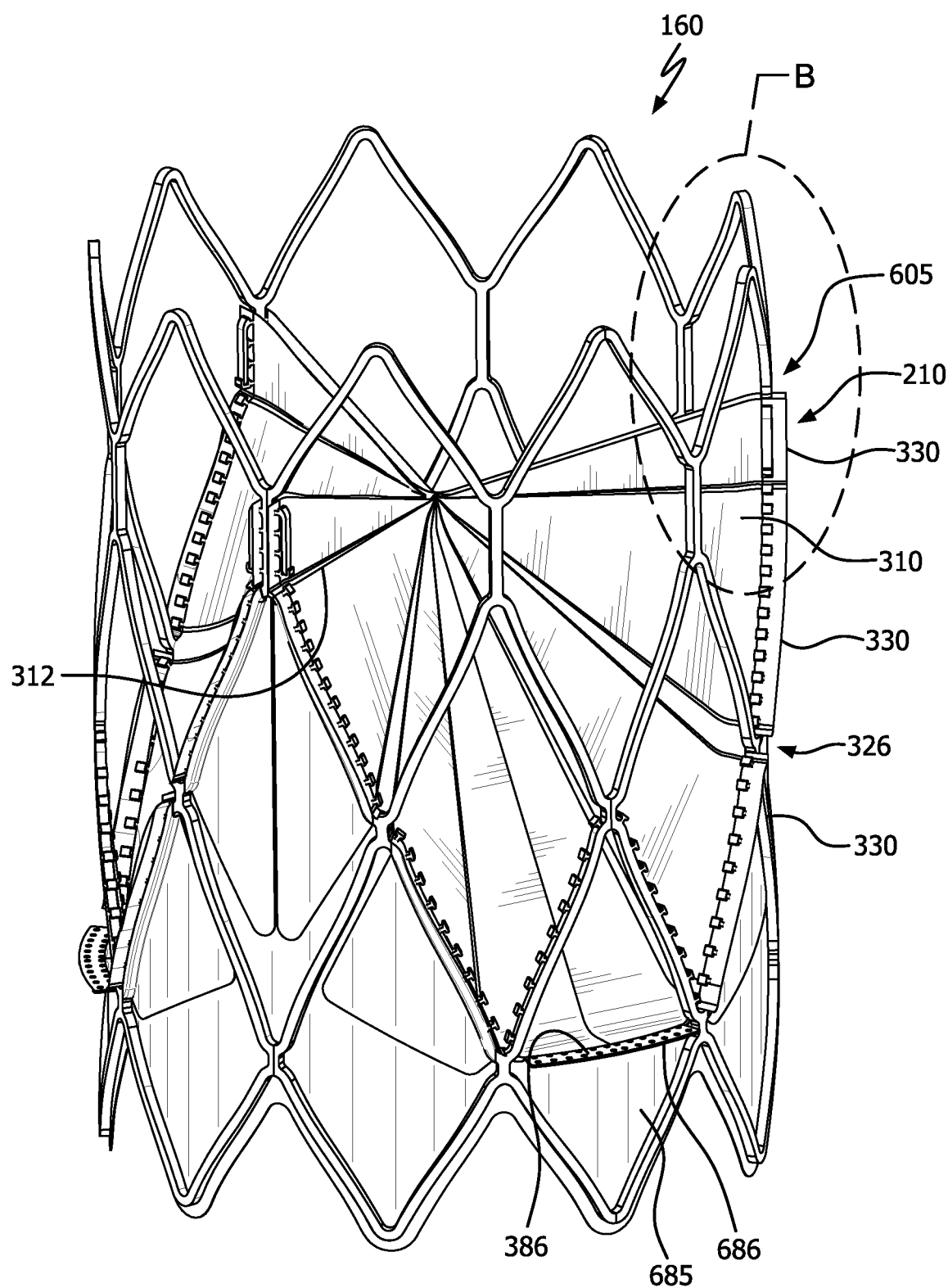
FIG. 18A is a perspective view of the leaflets of FIG. 17 assembled within the leaflet frame assembly of the leaflet frame and subcomponent, in accordance with an embodiment.
Figure 18B:
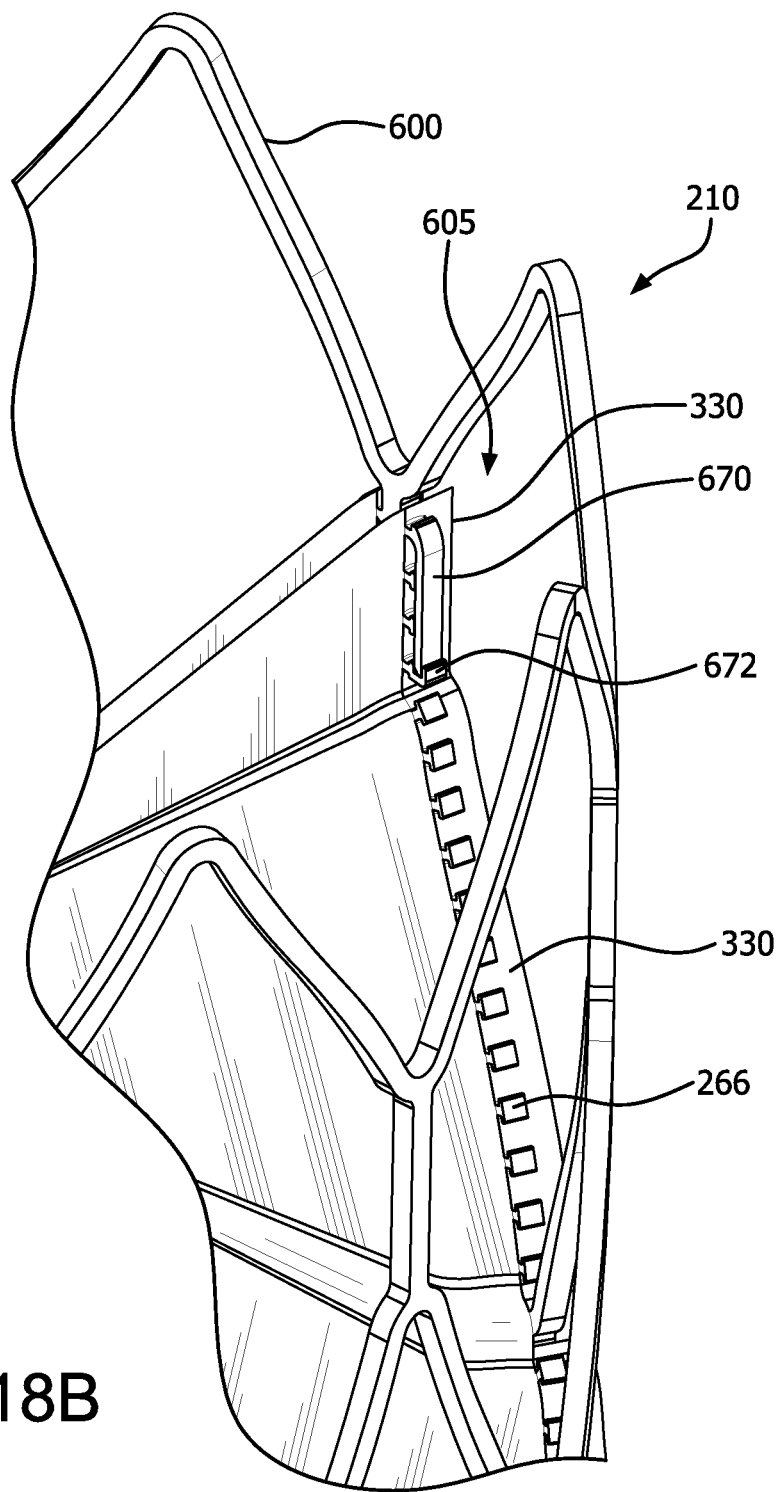
FIG. 18B is a magnified view of Box B in FIG. 18A showing the commissure post.
Figure 18C:
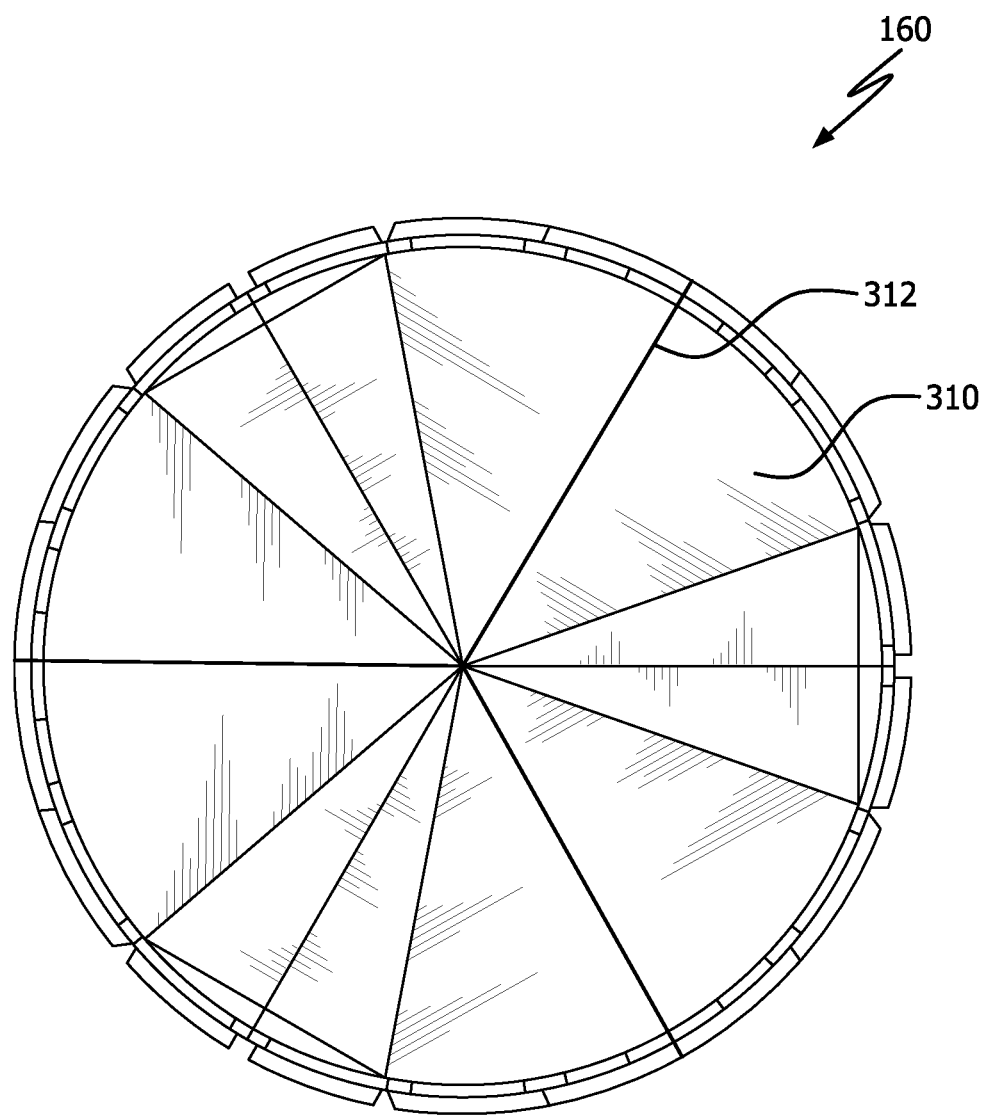
FIG. 18C is a top view of the prosthetic valve looking toward the outflow side in the closed position, in accordance with an embodiment.

In accordance with an embodiment of a transcatheter valve, the leaflet frame 600 and subcomponent 680 as a leaflet frame assembly 620 is provided with leaflets 310. FIG. 17 is a perspective view of three leaflets 310. FIG. 18A is a perspective view of the leaflets 310 assembled within the leaflet frame assembly 620 of the leaflet frame 600 and subcomponent 680. FIG. 18B is a magnified view of Box B in FIG. 18A showing the commissure post 210. FIG. 18C is a top view of the prosthetic valve 160 looking toward the outflow side in the closed position. The three leaflets 310 include leaflet attachment regions 330 that correspond to and are coupled to the leaflet frame projections 260 of the leaflet window sides 223. The portion of the leaflet attachment region associated with the commissure posts 210 is coupled to the leaflet frame projections 260 via the deformable locking bar restraining elements 605. Notches 326 are provided to correspond to and accommodate intersections of the leaflet frame elements. The leaflet base 325 defines a leaflet base flange 386 that includes a plurality of base flange apertures 327 that correspond to the first row of sewing apertures 608*a* and the second row of sewing apertures 608*b* of the subcomponent flange 686 of the subcomponent 680. The leaflet base flange 386 is coupled to the subcomponent flange 686 via suture that passes through the base flange apertures 327 and the first row of sewing apertures 608*a* and the second row of sewing apertures 608*b*. The attachment between the leaflet base flange 386 to the subcomponent flange 686 is effective to define a straight leaflet base that flexes about a straight line during the operation of the prosthetic valve.

Figure 19:
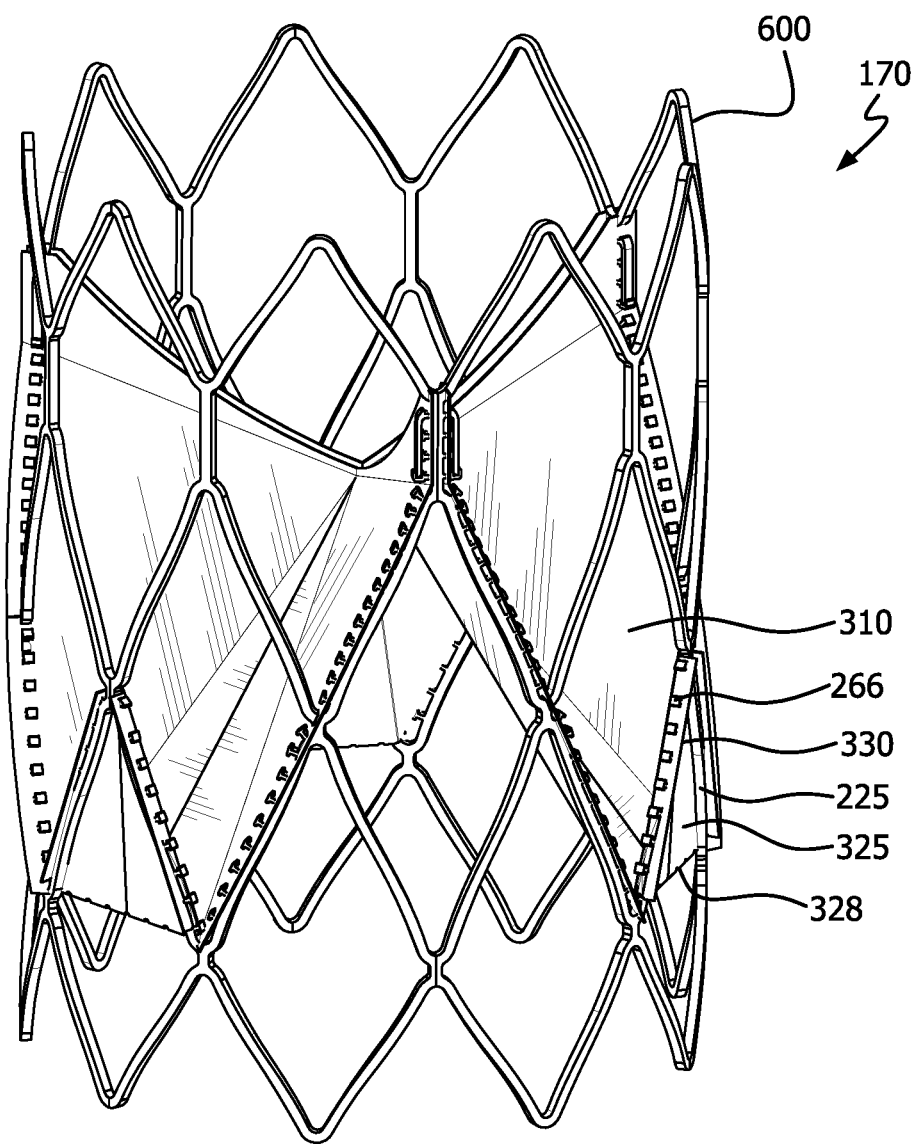
FIG. 19 is an alternative embodiment of a prosthetic valve.

FIG. 19 is an alternative embodiment of a prosthetic valve 170 wherein the leaflet base 325 of the leaflets 310 are coupled to the leaflet window base 225 via the leaflet frame projections 260 along the leaflet attachment region 330. The leaflet base 325 defines a fold 328 that is effective to define a straight leaflet base that flexes about a straight line defined by the fold 328 during the operation of the prosthetic valve. In an alternative embodiment, the fold 328 is sewn to a skirt of the subcomponent (not shown).

Sewing Cuff

In accordance with a prosthetic valve 100 suitable for surgical implantation, the prosthetic valve 100 further comprises a sewing cuff 285 about a leaflet frame 200 in accordance with an embodiment. The sewing cuff 285 is operable to provide structure that receives suture for coupling to the implant site. The sewing cuff 285 may comprise any suitable material, such as, but not limited to, double velour polyester and silicone. The sewing cuff 285 may be located circumferentially around a perimeter of the leaflet frame base 221 of the leaflet frame 200. The sewing cuff 285 may comprise a filler material, such as, but not limited to, a silicone ring.

Valved Conduit

Figure 20A:
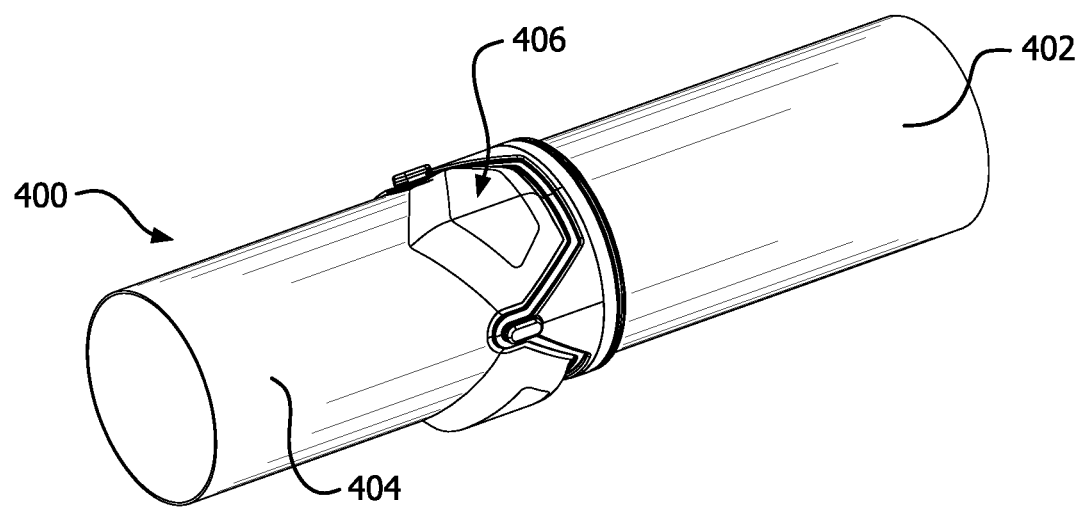
FIG. 20A is a perspective view of a prosthetic valved conduit incorporating a prosthetic valve shown in FIG. 1A, in accordance with an embodiment.
Figure 20B:
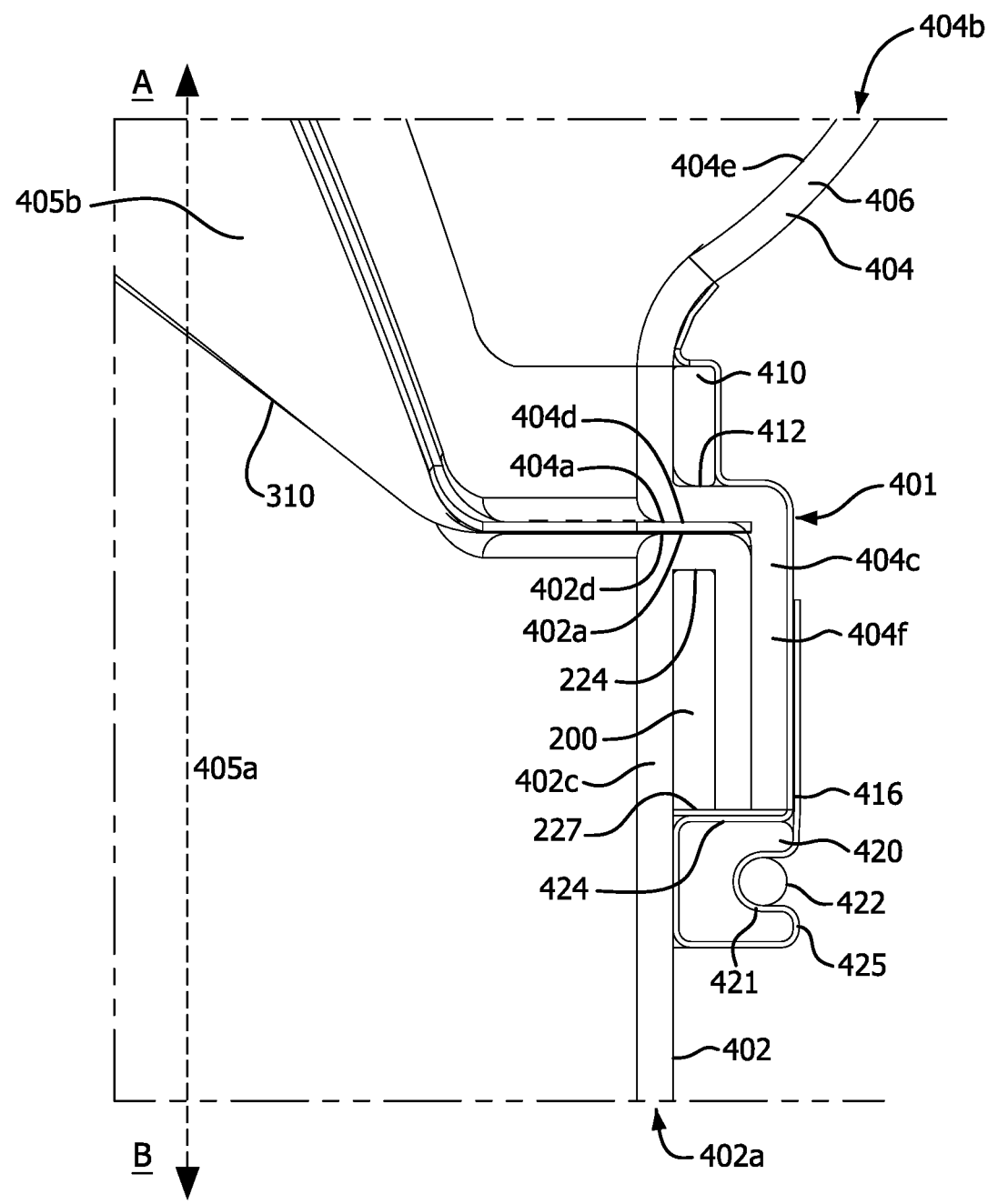
FIG. 20B(i) is a cross-sectional view of the valved conduit shown in FIG. 20A in the vicinity of a junction between the prosthetic valve, a first conduit, and a second conduit at the base of a leaflet frame concavity in between spaced-apart leaflet frame projections.
Figure 20C:
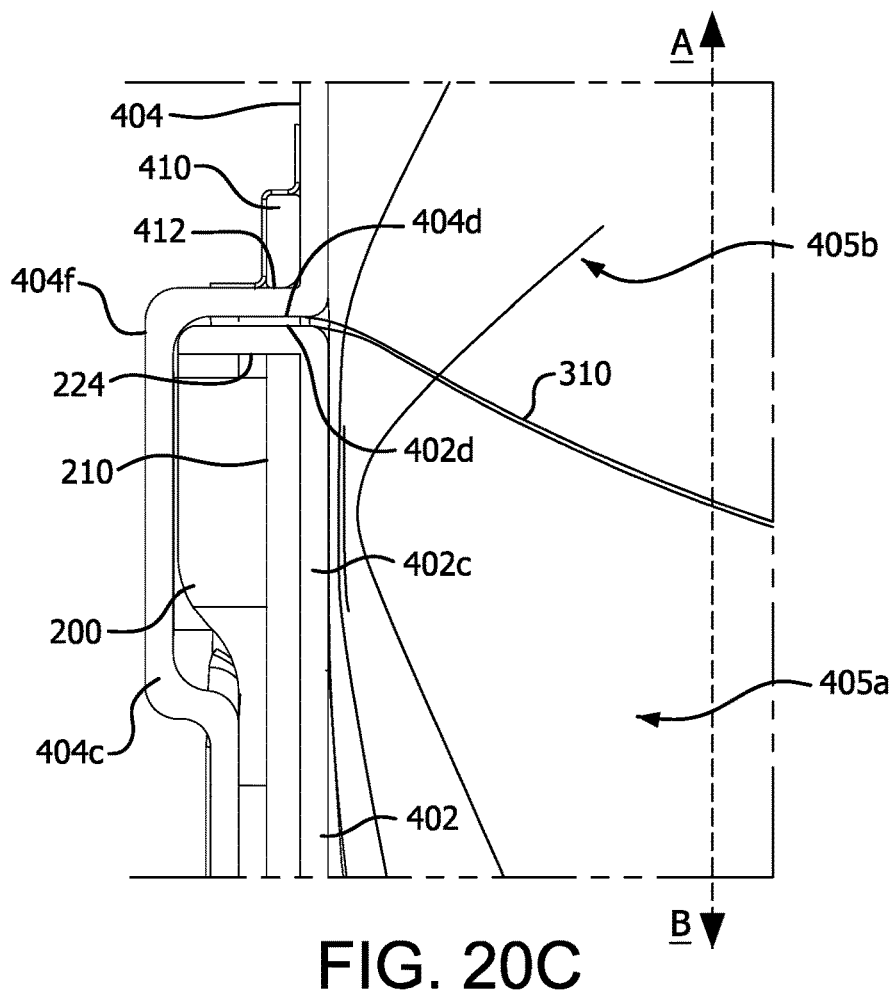
FIG. 20C is a cross-sectional view of the valved conduit shown in FIG. 9A in the vicinity of a junction between the prosthetic valve, the first conduit, and the second conduit at a commissure post.
Figure 20D:
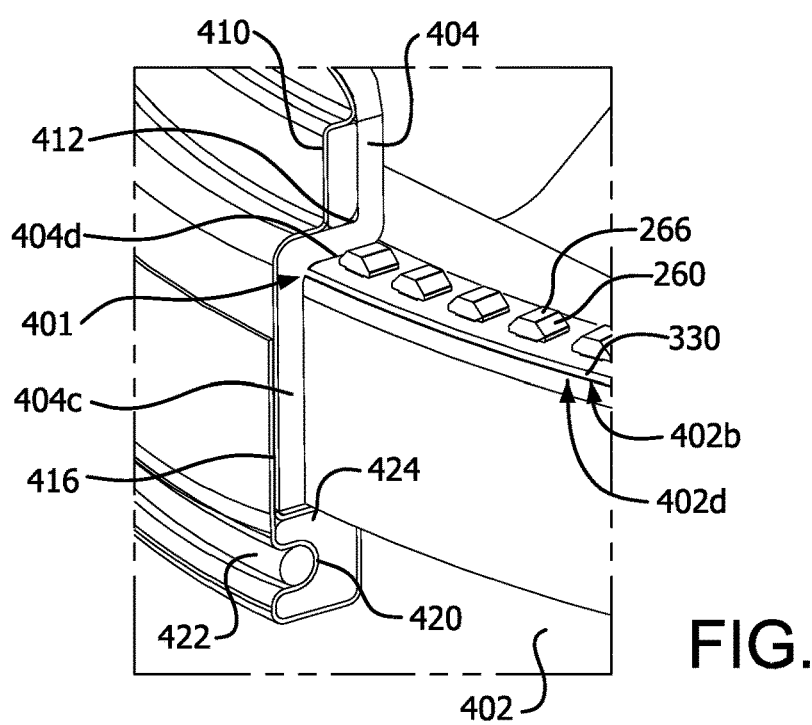
FIG. 20D is a cut-away, perspective view of the valved conduit shown in FIG. 20A in the vicinity of a junction between the prosthetic valve, the first conduit, and the second conduit at the base of a leaflet frame concavity.
Figure 20E:
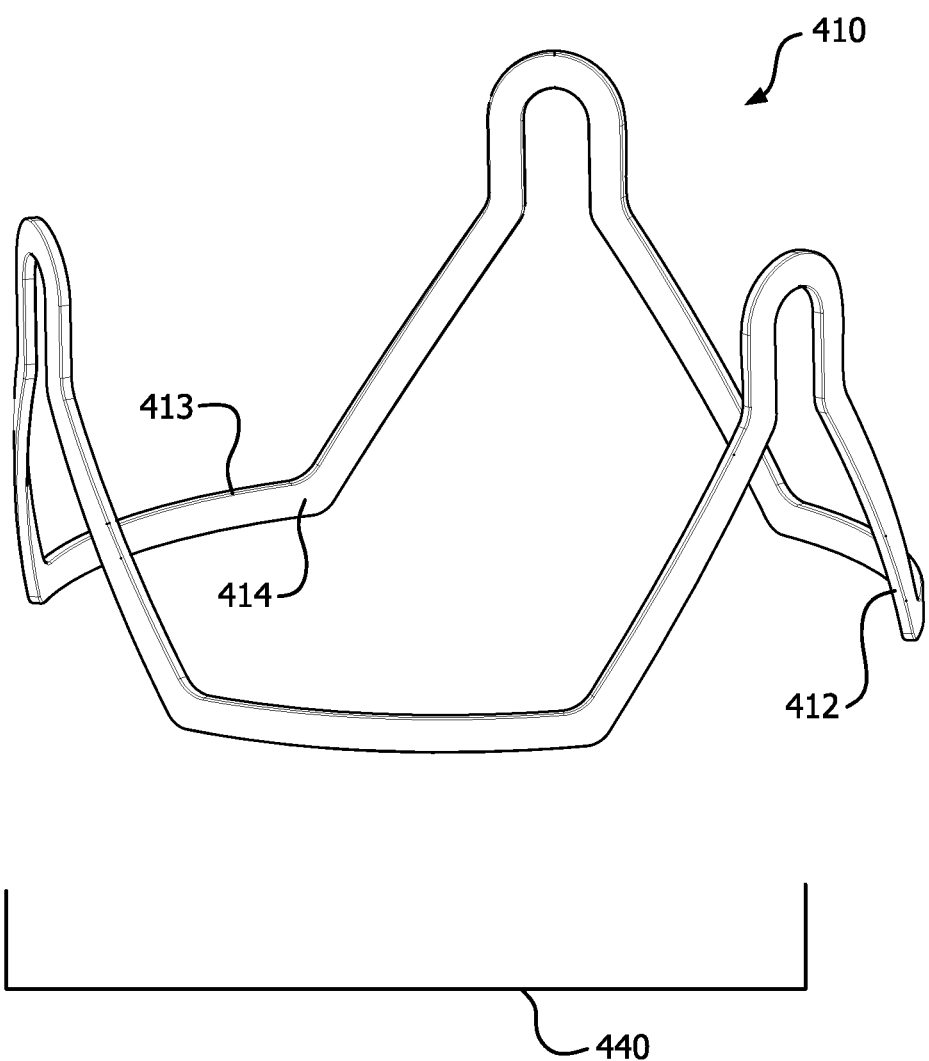
FIG. 20E is a perspective view of the first frame 410 incorporated in the embodiment shown in FIG. 20A to 20D.

In accordance with an embodiment, the prosthetic valve can be incorporated into a valved conduit. FIG. 20A is a perspective view a prosthetic valved conduit 400 incorporating a prosthetic valve 100, in accordance with an embodiment. FIGS. 20B(i) and (ii) are cross-sectional views of the prosthetic valved conduit 400 shown in FIG. 20A in the vicinity of the junction 401 between a prosthetic valve 100 and a first conduit 402 (shown as an inflow-side conduit) and a second conduit 404 (shown as an outflow-side conduit), at the base of a leaflet frame concavity 240. FIG. 20C is a cross-sectional view of the prosthetic valved conduit 400 shown in FIG. 20A in the vicinity of the junction 401 between the prosthetic valve 100 and the first conduit 402 and the second conduit 404 at a commissure post 210. FIG. 20D is a cut-away, perspective view of the valved conduit 400 shown in FIG. 20A at the junction 401 between the prosthetic valve 100 and the first conduit 402 and the second conduit 404 in the vicinity of the leaflet window base 225. The components of the prosthetic valved conduit 400 that are visible in FIGS. 20A to 20D include the first conduit 402, the second conduit 404, the leaflet frame 200, the leaflet 310, a first frame 410, a second frame 420, a retaining member 422, and a valve collar 416. FIG. 20E is a perspective view of the first frame 410 incorporated in the embodiment shown in FIG. 20A to 20D. In the embodiment shown in these figures, leaflet frame projections 260 are disposed on the leaflet frame second edge 224.

The valved conduit 400 may be used for replacing a native heart valve and an associated blood vessel in a patient. The pulmonary valve and the pulmonary artery are one non-limiting example of such a valve and an associated blood vessel. The aortic valve and the ascending aorta are another such example.

The valved conduit 400 comprises the prosthetic valve 100 and the first conduit 402 and the second conduit 404 arranged so that each conduit interfaces with one of the respective sides (namely, the leaflet first side 311 or the leaflet second side 313) of the leaflet attachment region 330 of the leaflet 310 (as previously described herein).

The first conduit 402 and the second conduit 404 each define a tubular structure that extends from a respective side of the leaflets 310 and outwardly therefrom to define together a conduit lumen 405 that is contiguous along axis A-B with the plurality of the leaflets 310 operable within the conduit lumen 405. In the embodiment shown, the leaflet frame 200 and the leaflets 310 are associated with the first conduit 402 and the second conduit 404 in such a way that the leaflets 310 control flow of blood through the first conduit 402 and the second conduit 404 by permitting blood flow into the first conduit 402 and the second conduit 404 during forward flow (in the B-to-A direction indicated by axis A-B) while substantially preventing flow of blood out of the first conduit 402 and the second conduit 404 in the reverse direction (in the A-to-B direction). The leaflet attachment region 330 is disposed at the junction 401 between the first conduit 402 and the second conduit 404.

In accordance with an embodiment, the prosthetic valved conduit 400 can be particularly adapted to create fluid turbulence within the second conduit 404 near the leaflets 310. To facilitate, the second conduit 404 can define one or more sinuses 406 within the second conduit lumen 405b. A sinus 406 can be a recess (such as a rounded concavity) on the second conduit inner surface 404e of the second conduit 404. A sinus 406 is disposed adjacent to and flanking each side of the commissure posts 210. In various embodiments, the second conduit 404 can be molded to define a plurality of sinuses 406. The sinus 406 of the second conduit 404 may be reinforced or rigidified to retain its shape; as such, it can be more rigid than other portions of the second conduit 404.

The valved conduit 400 incorporates a leaflet frame 200 and the leaflets 310 as previously described. The first conduit 402 defines a first conduit first luminal end 402a, a first conduit second luminal end 402b, and a first conduit lumen 405a therebetween. The second conduit 404 defines a second conduit first luminal end 404a, a second conduit second luminal end 404b, and a second conduit lumen 405b therebetween. The leaflet frame 200 circumscribes a first conduit section 402c adjacent the first conduit second luminal end 402b of the first conduit 402 such that the leaflet frame 200 does not have significant contact, if any, with a fluid flowing through the conduit lumen 405.

In accordance with some embodiments, a second conduit section 404c (a section not defining the conduit lumen 405) can circumscribe at least a portion of the leaflet frame 200. In particular, the second conduit section 404c and/or the valve collar 416 (described below) can define a circumferential recess 404f on the second conduit inner surface 404e that complements the outline of the leaflet frame 200 such that the leaflet frame 200 (and leaflet attachment region 330) substantially fills the circumferential recess 404f. The first conduit section 402c defines the section of conduit lumen 405 within the leaflet frame 200.

In various embodiments, the leaflets 310 can be coupled between the first conduit second luminal end 402b and the second conduit first luminal end 404a. More particularly, the first conduit second luminal end 402b and the second conduit first luminal end 404a define a first conduit mating surface 402d and a second conduit mating surface 404d, respectively. The first conduit mating surface 402d is disposed between the leaflet frame second edge 224 and the leaflet attachment region 330. In various embodiments, the first conduit 402 is everted about the leaflet frame second edge 224 such that at least a portion of the leaflet frame 200 is disposed between the everted section and the un-everted section of the first conduit 402, and the first conduit mating surface 402d is between these everted and un-everted sections. In addition, in various embodiments where the prosthetic valve 100 comprises the leaflet frame projections 260, the first conduit mating surface 402d can define a plurality of first conduit apertures 408 (see FIG. 21A) spaced apart from each other such that each of the leaflet frame projections 260 extend through a corresponding first conduit aperture 408. In this way, when assembled, the plurality of first conduit apertures 408 forms substantially the same spatial pattern as that of the leaflet apertures 308 and leaflet frame projections 260. With regard to the second conduit mating surface 404d, it is disposed between the first frame 410 and the leaflet attachment region 330.

The valved conduit 400 can further comprise one or more of the first frame 410, the second frame 420, and one or more bridge members, such as valve collar 416, that are configured to fixedly couple the second conduit 404 and/or the first conduit 402 to the leaflet frame 200. In various embodiments, the first frame 410 and the second frame 420 are configured to retain the leaflet frame 200, the leaflet attachment region 330, the first conduit mating surface 402d, and the second conduit mating surface 404d such that the leaflet attachment region 330 is retained therein and/or the junction 401 is substantially fluid-tight. As such, the second frame 420, the first frame 410, and the leaflet frame 200 are substantially coaxial. In addition, the second frame inner surface (not shown), the first frame inner surface 414, and the leaflet frame inner surface 202 are substantially aligned such that the transition between the first conduit 402 and the second conduit 404 at junction 401 is smooth (e.g., flush).

In various embodiments, the first frame 410 defines an annular ring that has a first frame first edge 412 (opposite a first frame second edge 413) that is substantially complementary to the leaflet frame second edge 224 or shaped to abut the plurality of projection tips 266 disposed above leaflet frame second edge 224. For example, the leaflet frame second edge 224 can define a plurality of leaflet frame concavities 240 and the first frame first edge can define a plurality of corresponding convexities 440 (see e.g., convexity 440 in FIG. 20E). In addition, the first frame 410 is adjacent to or abuts the leaflet frame second edge 224 such that the corresponding complementary features are in alignment with each other defining a junction 401 that is fluid tight. In some embodiments, a plurality of leaflet frame projections 260 can extend from the leaflet frame second edge 224 and be disposed between the leaflet frame second edge 224 and the first frame first edge 412. In addition, a projection tip 266 may press into or be embedded in the second conduit mating surface 404d, as shown in FIG. 20B(ii).

The first frame 410 circumscribes and is fixedly coupled to the second conduit outer surface 404g. In various embodiments, to couple the first frame to the second conduit 404, the valve collar 416 can comprise a film that is coupled to the second conduit 404 such that it circumscribes the first frame 410 to envelop the first frame 410 between itself and the second conduit 404. Stated another way, the valve collar 416 is fixedly coupled to a second conduit outer surface 404g adjacent to the first frame second edge 413. The film can be coupled to the second conduit 404 with an adhesive agent, through thermal bonding, and/or sewn. In other embodiments, the first frame 410 can be adhered, bonded, and/or sewn to the second conduit 404. While not explicitly recited, it is understood that other suitable coupling mechanisms or techniques may be used.

Similarly, the second frame 420 defines the shape of an annular ring that has a second frame second edge 424 that is substantially complementary to the leaflet frame first edge 227. The second frame 420 is adjacent the leaflet frame first edge 227 such that the corresponding complementary features, if any, are in alignment. The second frame 420 cooperates with the first frame 410 to retain to the leaflet frame 200, the first conduit mating surface 402d, the second conduit mating surface 404d, and the leaflet attachment region 330. To facilitate such cooperation, in various embodiments, the second frame 420 can be configured to be fixedly coupled to one or more bridge members, such as the valve collar 416, described below.

Both the first frame 410 and the second frame 420 comprise a semi-rigid or rigid structure. Specifically, the first frame 410 and the second frame 420 can comprise any semi-rigid or rigid metallic or polymeric material that is generally biocompatible, such as titanium alloys, stainless steel, cobalt-nickel alloy, polypropylene, acetyl homopolymer, acetyl copolymer, other alloys or polymers, or any other material that is generally biocompatible having adequate physical and mechanical properties to function as either the first frame 410 and the second frame 420 as described herein.

In various embodiments, the valve collar 416 can be configured to maintain a distance (or resist an increase in distance) between the first frame 410 and the second frame 420 such that the two frames can retain the leaflet frame 200 therebetween, such as by a frictional fit. In various embodiments, the valve collar 416 can define a tubular shape that extends from the second conduit first luminal end 404a and circumscribes the leaflet frame 200. The valve collar 416 can be fixedly coupled to and can extend between the first frame 410 and the second frame 420. As discussed above, the valve collar 416 can also be configured to fixedly couple the first frame 410 to the second conduit 404.

The valve collar 416 can be any pliable material that is generally biocompatible. In various embodiments, the valve collar 416 can be a pliable, inelastic film or a strained elastic film. The film can comprise an adhesive that facilitates securement of the valve collar 416 to the second conduit 404 and/or the first frame 410. For example, the film can comprise biocompatible material such as ePTFE, polyethylene such as polyethylene terephthalate (PET), and polypropylene, among others. Suitable adhesive can be a biocompatible elastomeric polymer such as FEP, urethanes, silicones, and isobutylene/styrene copolymers, block polymers and combinations thereof, among others. While the valve collar 416 is described, other types of bridging members can be used to fixedly couple the first frame 410 and the second frame 420 to the leaflet frame 200, such as a plurality of rigid rods that are spaced apart from each other and coupled to and extending between the first frame 410 and the second frame 420.

To facilitate fixedly coupling the valve collar 416 to the second frame 420, in various embodiments, the second frame 420 can define a channel 421 on a second frame outer surface 425 that extends along its circumference and is configured to receive a retaining member 422, such as a tied cord (as shown in FIGS. 20A, 20B, and 20C), spring retaining ring, or clamp ring, among others. In the embodiment shown, the valve collar 416 is everted about the second frame 420 such that the second frame 420 is disposed about the valve collar 416 and a section of the valve collar 416 is disposed between the second frame 420 and the retaining member 422 disposed in the channel 421 thereby restricting movement of the valve collar 416 relative to the second frame 420. Retaining member 422 can be any generally semi-rigid to flexible structure made of metal or polymeric material that is generally biocompatible. While not explicitly recited, it is understood that other suitable retention mechanisms or techniques may be used.

The first conduit 402 and the second conduit 404 can be any cylindrical textile structure suitable for use as a prosthetic vascular graft. In various embodiments, the first conduit 402 and the second conduit 404 can comprise ePTFE or PET. The first conduit 402 and the second conduit 404 can be an extruded tube of expanded polytetrafluoroethylene, such as GORE-TEX® Vascular Grafts.

Methods of Making

A method of making a prosthetic valve, in accordance various embodiments, comprises forming (such as by cutting a metal tube, casting, molding, printing, or the like) a leaflet frame defining leaflet frame windows and one or more leaflet retention surfaces, having commissure posts therebetween, and a plurality of projections spaced apart from each other extending from one or more leaflet retention surfaces. Each leaflet frame projection is configured to couple to a leaflet. The leaflet frame projections can have a projection base portion and a projection head portion, where the projection base portion meets the leaflet retention surface at one side and the projection head portion on the opposite side. Some embodiments of the leaflet frame can further define one or more slots that extend through one or more frame elements that define the leaflet frame windows. Each slot is dimensioned to receive at least a single thickness of the leaflet, e.g., the leaflet attachment region. The slot can be a base receiving slot or a side receiving slot. In addition, each commissure post defines a post slot dimensioned to receive a double thickness of the leaflet. In further embodiments, the frames can comprise one or more attachment slots or other frame openings that defines an internal edge from which leaflet frame projections can extend.

The same or different method can comprise obtaining a sheet or tube of material comprising one or more layers of expanded PTFE composite and cutting a leaflet from the sheet or tube, where one or more apertures are formed in the leaflet attachment region of the leaflet. The apertures can be cut to dimensions suitable for coupling to a leaflet frame projection on a leaflet frame. In particular, the aperture can have a size and shape that is substantially the same as a transverse, cross-sectional size and shape of the projection base portion of the leaflet frame projection. The method can further comprise coupling a leaflet reinforcement to the leaflet and further, cutting the leaflet apertures into both the leaflet and the leaflet reinforcement simultaneously.

The same or different method can comprise coupling the leaflet to the leaflet frame by aligning an aperture on the leaflet with the corresponding projection on the leaflet frame, pressing the leaflet so that the leaflet projection extends through the aperture, and/or pressing the leaflet frame so that the leaflet projections extends through the apertures. In a further embodiment, the method can comprise pressing either the leaflet or the leaflet frame so that a leaflet surface defining the aperture contacts the leaflet retention surface. These steps can be repeated for the adjacent aperture and the corresponding adjacent projection until each aperture extends through a corresponding one of the leaflet frame projections.

In further embodiments, the method can comprise placing a commissure post cap about the commissure post. More particularly, the method can comprise aligning the commissure post cap so that the commissure post slot is aligned with the one or two leaflets extending through the commissure post slot, and then placing the cap about the post.

Alternatively, coupling the leaflet to the leaflet frame can comprise passing a portion of the leaflet defining the leaflet attachment region through the base receiving slot, the side receiving slot, and/or the post slot and wrapping the leaflet attachment region around the outer side of a commissure post, the two leaflet window sides, and/or the leaflet window base, aligning one of the apertures on the leaflet with the corresponding projection on the leaflet frame, pressing the leaflet frame projection through the aperture, and seating the leaflet about the leaflet frame projection. These steps can be repeated for the adjacent aperture and corresponding projection until all apertures extend through a projection.

A method of making a prosthetic valved conduit, in accordance with various embodiments, comprises forming an inflow assembly by coupling an first conduit to the leaflet frame (such as one made in accordance with the above described method) and coupling the leaflets (such as ones made in accordance with the above described method) to the first conduit and the leaflet frame. In various embodiments, coupling the first conduit to the leaflet frame can comprise everting an end of the first conduit about the leaflet frame at the leaflet frame second edge such that at least a portion of the leaflet frame is disposed between the everted portion and the un-everted portion and/or pressing the adjacent section of the first conduit against the leaflet frame projections to form one or more apertures in the first conduit at the first conduit mating surface. In various embodiments, coupling the leaflets to the first conduit and the leaflet frame can comprise aligning a leaflet aperture with the corresponding leaflet frame projection, pressing the leaflet frame projection through the leaflet aperture, and/or seating the leaflet about the leaflet frame projection.

The same or different method comprises forming an outflow assembly by coupling a first frame to a second conduit such that the first frame circumscribes the second conduit at a location intermediate to the ends of the second conduit and coupling a valve collar to the first frame and/or second conduit such that the valve collar extends from an end of the second conduit. In various embodiments, the outflow assembly is formed by laminating an inelastic tubular film to the second conduit such that the first frame is sealed therebetween and the tubular film extends from an end of the conduit, thereby forming the valve collar.

The method can further comprise shape setting/molding the second conduit to form a plurality of sinuses in the second conduit sidewall of second conduit adjacent to the first frame second edge. The second conduit can also be shape set so that the second conduit abuts the first frame first edge to define a second conduit mating surface on the second conduit inner surface of the second conduit. In an embodiment, a generally cylindrical mold comprises sinus mold features and a annular ledge about the circumference adjacent the sinus mold features. The ledge can define the shape of the first frame first edge to facilitate positioning the first frame relative to the sinus mold features and/or to mold the second conduit to abut the leaflet frame second edge. In various embodiments, the sinus mold features can be extendible from the interior of the cylindrical mold, and optionally retractable into the interior of the cylindrical mold. The cylindrical mold can comprise one sinus mold per leaflet. In various embodiments, the sinus molds can be extended into position after applying (such as wrapping) a tubular film about the second conduit and the first frame but prior to heating (e.g., laminating) the tubular film to the second conduit. More particularly, in various embodiments, the sinuses can be extended into position before or after an overwrap (e.g., sacrificial layers) is applied to the film and the second conduit prior to heating (e.g., laminating). Also, in various embodiments, lamination can be done in a positive pressure oven to facilitate better contact of the film with the outer surface of the second conduit, particularly in and around the area where the sinuses are being molded.

The same or different method comprises coupling the inflow assembly to the outflow assembly and can comprise inserting the leaflet frame end of the inflow assembly into the valve collar end of the outflow assembly; pressing the ends together such that the corresponding features on the complementary mating surfaces are aligned; placing a second frame about the valve collar and adjacent to the leaflet frame first edge; and fixedly coupling the second frame to the valve collar. In various embodiments, the second frame can be coupled to the first frame by everting the valve collar about the first frame and placing a retaining member about the everted section of the valve collar such that the valve collar's movement is restricted. In various embodiments, the retaining member is disposed in a channel on the first frame outer surface of the first frame.

Having generally described this disclosure, a further understanding can be obtained by reference to certain specific examples illustrated below which are provided for purposes of illustration only and are not intended to be all inclusive or limiting unless otherwise specified.

Example 1: Prosthetic Valve

Leaflet Construction: A leaflet material was prepared having multiple layers of ePTFE membrane imbibed with a fluoroelastomer. More specifically, the ePTFE membrane that had been subjected to temperatures at or above the crystalline melt temperature of PTFE was manufactured according to the general teachings described in U.S. Pat. No. 7,306,729. The ePTFE membrane had a mass per area of about 0.5 g/m$^2$, a thickness of about 500 nm, a IPA bubble point of about 200 KPa, a matrix tensile strength of about 700 MPa in the longitudinal direction and about 380 MPa in the transverse direction. This membrane was imbibed with a fluoroelastomer that was formulated according to the general teachings described in U.S. Pat. No. 7,462,675. The copolymer consists essentially of between about 60 and 65 weight percent perfluoromethyl vinyl ether and complementally about 40 and 35 weight percent tetrafluoroethylene.

The percent weight of the fluoroelastomer relative to the ePTFE was about 70%.

The fluoroelastomer was dissolved in Fluorinert Electronic Liquid FC-72 (3M, St Paul, Minn.) in a 1.5% concentration. The solution was coated onto a polyolefin backer film and the ePTFE membrane was laminated to the coating solution. The resulting package was dried in a convection oven set to 110° C. for 45 seconds. The resulting composite material had a mass per area of 1.52 g/m$^2$.

The above composite material was circumferentially wrapped about 60 times with the elastomer coated side facing inward around stainless steel mandrel with a diameter of about 25 mm to form a tube. The tube was longitudinally cut and removed from the mandrel to form a loose stack measuring about 75 mm×75 mm.

The loose stack was placed on a sheet of laser absorbent glass. A polyethylene terephthalate release liner was placed on top of the loose stack and a sacrificial ePTFE cushion layer was placed on top of that. The assembly was placed between the platens of a heated press set to 240° C. and compressed with a pressure setting of about 200 kPa for about 5 minutes. The assembly was removed from the press and allowed to cool. The release liner and the sacrificial ePTFE cushion layer were removed from the thermally bonded coupon. The thermally bonded coupon was then removed from the glass.

A second thermally bonded coupon was created in the same manner except that it was not removed from the glass.

A leaflet with reinforcement strip was formed from these two thermally bonded coupons using a $CO_2$ laser to cut the coupons in the following manner.

First, the thermally-bonded coupon remaining on the glass was cut to form an edge defining the inner curve of a reinforcement strip. The shape of the cut line is illustrated in FIG. 10C at dashed line 331. The excess material of the coupon interior to the dashed line 331, labeled as region X in FIG. 10C, was removed from the glass.

The second thermally-bonded coupon was placed over the remaining portion of the first thermally-bonded coupon. These two thermally-bonded coupons were thermally-bonded together with a press in the manner described above. After bonding, a laser cut was made to the bonded coupons to form the perimeter of the leaflet according to the shape illustrated in FIG. 10C by solid line 334 such that the inner curve of reinforcement strip was disposed along the leaflet base 325. Apertures 308 according to the pattern shown in FIG. 10C were also laser cut from the dual layers where the reinforcement strip was located. The foregoing process was repeated two more times to make three leaflets.

Frame Construction: To form the leaflet frame, a tube of cobalt chromium (MP35N, full hard and aged) having a 25 mm OD and 0.4 mm wall thickness was obtained. The tube was laser cut with to form the leaflet frame. The pattern cut in the tube provided a leaflet frame in accordance with that shown in FIGS. 2A and 2B. The leaflet frame defined 50 projections per leaflet window. The dimensions of the leaflet frame projections were as follows: 0.2 mm base portion height, 0.25 mm base portion width, 0.4 mm base portion thickness, 0.1 mm head portion height, 0.375 mm head portion width, and 0.4 mm head portion thickness. The laser cut tube was electro-polished, completing the formation of the leaflet frame.

Prosthetic Valve Assembly: Three leaflets and a leaflet frame formed in the manner described above were obtained. The leaflet frame and leaflets were coupled to each other to form the prosthetic valve in the following manner.

First, the leaflet frame was immobilized by press-fitting the first edge of the leaflet frame onto a mandrel-like holder so that the second edge of the leaflet frame was disposed above the end of the mandrel-like holder. One of the leaflets was placed over the leaflet frame at one of the leaflet windows so that the reinforcement strip was facing away from the leaflet frame, the leaflet free edge was extending into the interior of the frame, and each aperture was generally aligned with a corresponding one of the leaflet frame projections. A blunted razor blade was used to press, in a sequential manner, the leaflet material in the region of the reinforcement strip between each leaflet frame projection so that each leaflet frame projection extended through the corresponding aperture. This process was repeated for the remaining two leaflets on the remaining two leaflet windows.

Three commissure post caps like that illustrated in FIG. 13B were obtained by machining a PEEK solid body. The post cap was slid onto each post and an adhesive (Nusil MED1511) was applied to ensure a more permanent coupling.

A sewing ring can also be coupled to the base of the leaflet frame.

Example 2: Pulmonary Valved Conduit

Leaflet Frame and Leaflet Construction: A leaflet frame was prepared as per Example 1, except that the dimensions of the leaflet frame projections were as follows: 0.4 mm base portion height, 0.25 mm base portion width, 0.4 mm base portion thickness, 0.1 mm head portion height, 0.375 mm head portion width, and 0.4 mm head portion thickness. Three leaflets were prepared as per Example 1, except that the leaflets did not have a reinforcement strip.

First Conduit and Second Conduit: Each conduit was an ePTFE round tube with an ID of about 23.7 mm and a wall thickness of about 1.2 mm. Each extruded tube was about 150 mm in length.

First Frame Construction: The first frame was formed from a tube of cobalt chromium (MP35N, full hard and aged) with a 25 mm OD, a 0.35 mm wall thickness. The tube was laser cut to form a first frame as shown in FIG. 20E. The laser cut first frame was electro-polished, completing the formation of the first frame.

Second Frame Construction: The second frame was made of stainless steel 303 and has a 24.4 mm ID, a 26.9 mm OD, and a 1.0 mm height and defined a channel having a depth of 0.5 mm on the outer-facing surface along the circumference.

Film used to form the Valve Collar: An ePTFE/FEP film was used to form the valve collar. The film was a thin, non-porous ePTFE provided with an adhesive coating of thermoplastic fluorinated ethylene propylene (FEP). The ePTFE/FEP film had a thickness of about 0.0064 mm, a bubble point of greater than about 0.6 MPa, a Gurley No. (permeability) of greater than 60 (minute/1 square inch/100 cc); (or 60 (minute/6.45 square cm/100 cc)), a density of 2.15 g/cc and a tensile strength of about 300 MPa in the longitudinal direction (i.e., the strongest direction).

Figure 21A:
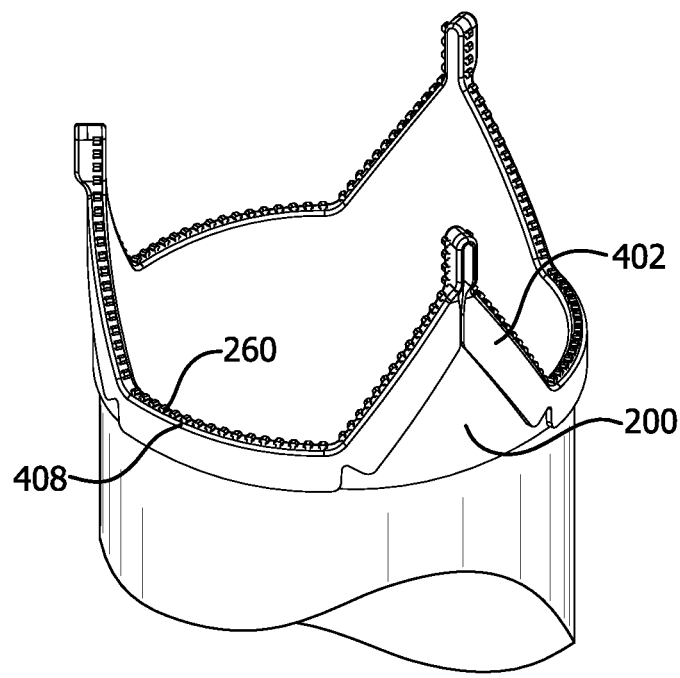
FIG. 21A is a perspective view of an intermediate structure in making the valved conduit shown in FIG. 20A, in accordance with an embodiment.

Inflow Assembly Construction: One of the two ePTFE tubes (referred to as the first conduit) and a leaflet frame as described above were obtained. The first conduit was slid onto a tapered stainless steel mandrel that had a 22-26 mm diameter range. The leaflet frame was then placed about the first conduit so that the leaflet frame second edge faced the tapered (smaller diameter) end. The leaflet frame was positioned at an intermediate location between the ends of the first conduit such that at least 20 mm of tube extended beyond the second edge of the leaflet frame. A series of nine generally longitudinal cuts were made on the section of the first conduit that extended beyond the second edge of the leaflet frame. Each cut started 2-3 mm above the second edge. Three of the cuts started above a commissure post. The other cuts started above the point where a leaflet window side interfaced with a leaflet window base. Each of the strips was everted over the corresponding one of the leaflet windows. Pressure was applied so that the leaflet frame projections on the leaflet frame second edge penetrated the first conduit wall. The strips were then trimmed to obtain the intermediate leaflet frame-conduit structure. This structure is shown in FIG. 21A with the leaflet frame 200 and the first conduit 402.

Figure 21B:
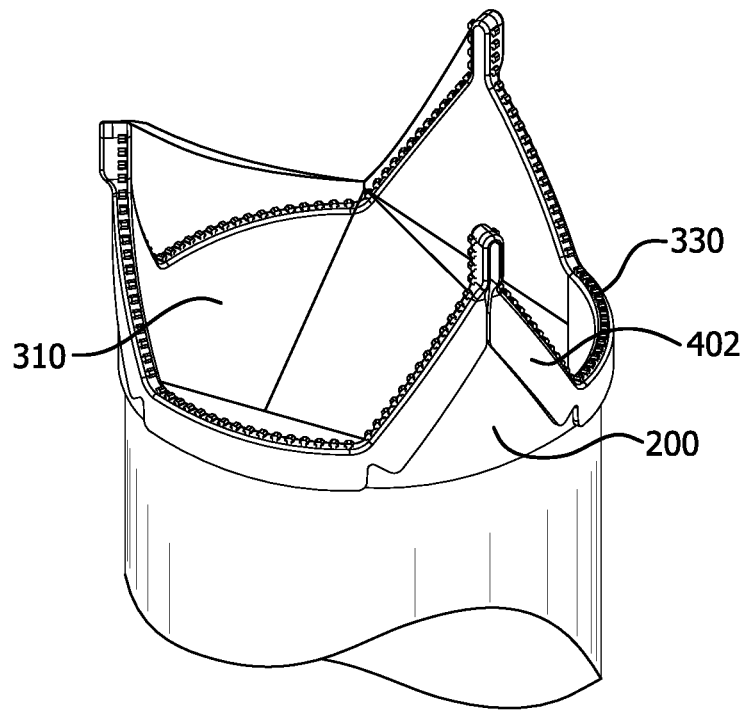
FIG. 21B is a perspective view of another intermediate structure in making the valved conduit shown in FIG. 20A, in accordance with an embodiment.

A leaflet formed in the manner described above (except without reinforcement strip) was then coupled to each of the leaflet windows. One of the leaflets was placed over the leaflet frame at one of the leaflet windows so that the leaflet free edge was extending into the interior of the frame and each aperture was generally aligned with a corresponding one of the leaflet frame projections. A blunted razor blade was used to press, in a sequential manner, the leaflet material in the region of the attachment region between each leaflet frame projection so that each leaflet frame projection extended through the corresponding aperture. This process was repeated for the remaining two leaflets on the remaining two leaflet windows. The attachment process began near the center of the leaflet and advanced toward each of the commissure posts in a sequential fashion, but this can begin at any point and need not be sequential. The intermediate frame-conduit-leaflet structure is shown in FIG. 21B with the leaflet frame 200, the first conduit 402, and the leaflet 310.

Figure 21C:
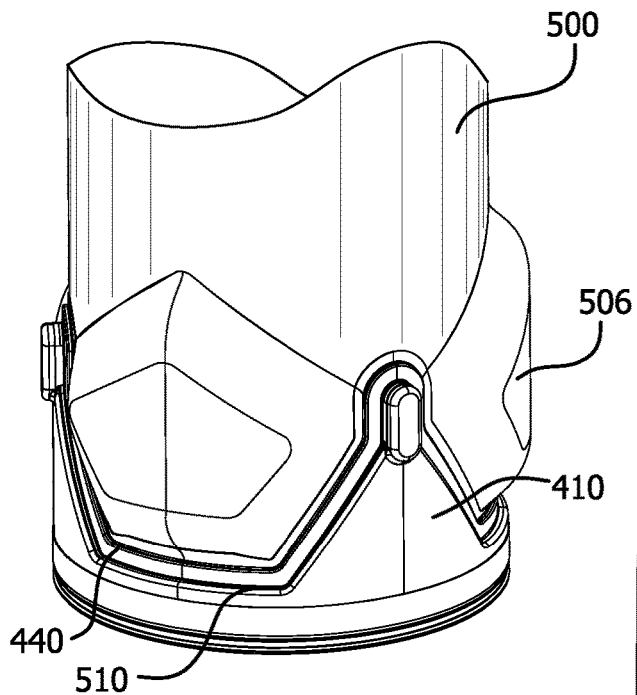
FIG. 21C is a perspective view of an intermediate section of a sinus mold used in the making of the valved conduit shown in FIG. 20A, in accordance with an embodiment.

Out-flow Assembly Construction: The other of the two ePTFE tubes (referred to as the second conduit) and a first frame as described above were obtained. The second conduit was slid over a custom mandrel with radially extendible sinus molds. The surface of the mold defines an annular ledge adjacent the sinuses that defines a surface contoured to mimic the leaflet frame second edge. The OD of the diameter above the ledge (disregarding extendible sinus molds) was approximate 23.7 mm, and below the ledge, it was approximately 25.6 mm. (To better illustrate, an intermediates section of the mold 500 is shown in FIG. 21C defining an annular ledge 510 and radially extendible sinuses 506.) An end of the second conduit was positioned on the mold to extend slightly below the annular ledge and to cover the sinus region of the mold. The first frame was positioned about the second conduit abutting the underlying annular ledge. The sinus molds are then extended into position. A protective covering made of polyimide film was placed around the mold below the second conduit and the first frame. The second conduit portion overlapping the sinus region of the mold, the second frame, and a portion (~20 mm) of the mold beyond the second conduit end were then wrapped with a layer of fluorinated ethylene propylene (FEP) followed by ten layers of the above-described PTFE/FEP film with the FEP side facing inward. Sacrificial release layers were then wrapped around the PTFE/FEP film in preparation for shape-setting of the sinus molds and lamination of the PTFE/FEP film extending from the end of the second conduit luminal first end. The sacrificial layers were a heat-resistant layer, excess ePTFE tube material for cushion, and an ePTFE compression wrap. The position of the second conduit at the opposite end was fixed to prevent shrinking during lamination. The resulting assembly was placed into a forced air oven set to around 320° C. for approximately 40 minutes. The assembly was removed from the oven and allowed to cool to room temperature (~22° C.), and the sacrificial layers were removed.

Figure 21D:
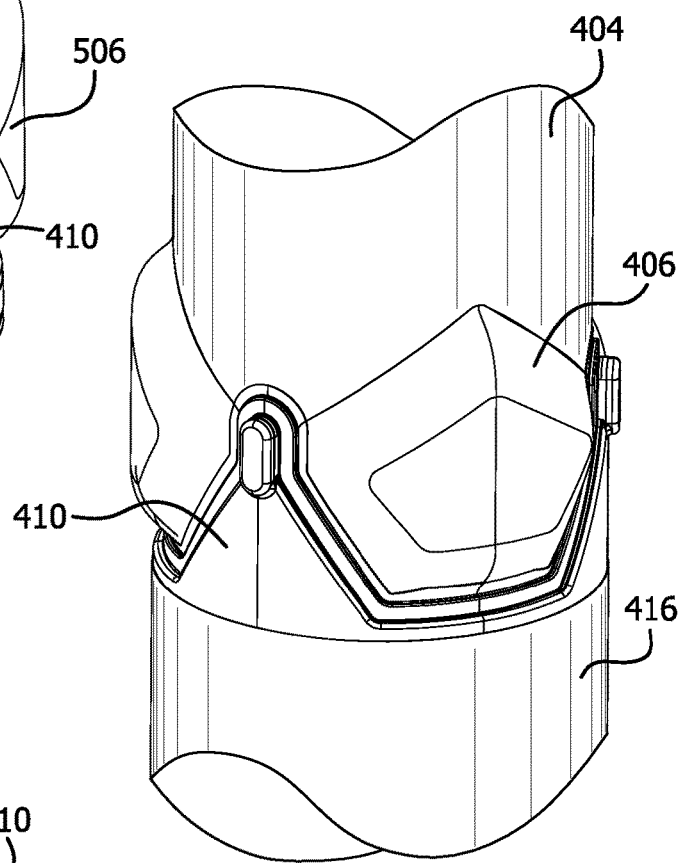
FIG. 21D is a side view of intermediate conduit-frame-collar structure formed in making the valved conduit shown in FIG. 20A, in accordance with an embodiment.
Figure 21E:
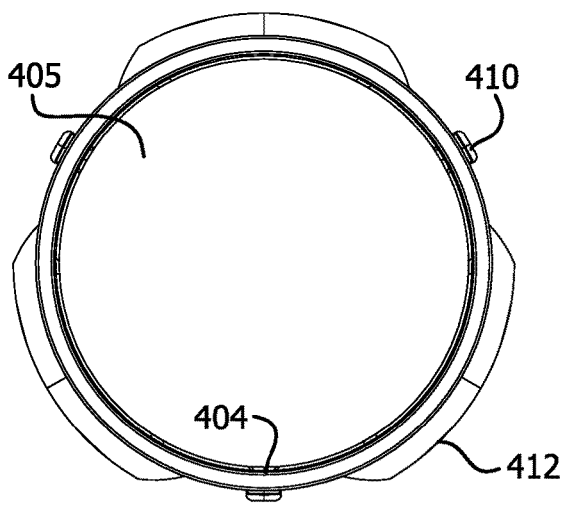
FIG. 21E is a top view of intermediate conduit-frame-collar structure formed in making the valved conduit shown in FIG. 20A, in accordance with an embodiment.

While the conduit-frame-collar structure was still on the mold, the laminate valve collar precursor was everted to trim any excess conduit material underneath. A side view of intermediate conduit-frame-collar structure is depicted in FIG. 21D with the first frame 410, the second conduit 404 defining a plurality of sinuses 406, and the valve collar 416. A top view of the intermediate conduit-frame-collar structure is depicted in FIG. 21E with the first frame 410 and the second conduit 404 defining a plurality of sinuses 406 and a conduit lumen 405, with the valve collar 416 not visible in this view.

Joining of Inflow Assembly and Outflow Assembly to Form Valved Conduit: To accommodate the insertion of the leaflet frame side of the inflow assembly into the first frame side of the outflow assembly, three longitudinal cuts were made in the valve collar 416 at the end about half the length of the valve collar precursor. The leaflet frame side of the inflow assembly was inserted into the first frame side of the outflow assembly such that the first conduit luminal second end mated with the second conduit luminal first end adjacent to the first frame first edge. The second frame was then slid over the combined assembly and into a position around the valve collar abutting the leaflet frame first edge of the leaflet frame. The valve collar was then everted over the second frame and pulled taut to press against the second frame. A suture, as the retaining member, was tied around the valve collar into the channel of the second frame such that the inflow and outflow assemblies were securely joined. The excess valve collar was then trimmed up to the second frame, and a pulmonary valved conduit as shown in FIG. 20A was formed.

Example 3: Transcatheter Self-Expanding Prosthetic Valve Frame Preparation

A cylindrical stainless steel hollow mandrel with a diameter of 23.6 mm was obtained. The mandrel had about 1 mm diameter perforations through the wall distributed over about a 100 mm length of the mandrel. About a 90 mm length of sacrificial release material (4:1 PTFE heat shrink tubing, initial ID 25.4 mm, item number 96974, Zeus, Inc., Orangeburg, S.C.) was placed over the mandrel, leaving perforations at the end exposed, and shrunk tight to the mandrel by heating in an air oven set at 300° C. for 15 minutes. The assembly was allowed to cool to room temperature.

A FEP/ePTFE component was obtained having the following properties: mass per area of 50.6 grams per square meter and tensile break strength of 1.7 kgf/cm in the longitudinal direction and 1.64 kgf/cm in the transverse direction. The tensile tests were conducted at 23° C. on a 25.4 mm wide sample, using a gage length of 25.4 mm and a strain rate of 100% per minute. Two layers of the FEP/ePTFE construct, 85 mm wide, were wrapped circumferentially around the mandrel over the sacrificial release material with the FEP side away from the mandrel. The film layers were bonded by placing the mandrel and film in an air oven set at 360° C. for 15 minutes and allowed to cool resulting in a composite component. The composite component, while still on the mandrel, was laser trimmed and perforated to form a subcomponent 680 shown in FIG. 16A, using a CO2 laser and left on the mandrel. The subcomponent 680 comprises subcomponent apertures 608, a skirt 685, first fold-over portions 683, second fold-over portions 682, and third fold-over portions 684. The third fold-over portions 684 further comprise a first row of sewing apertures 608a and a second row of sewing apertures 608b which are parallel to each other.

A 5.79 mm diameter, 0.406 mm thick nitinol tube was obtained (Alloy ASTM F 2063-05, Part number 11437-99, Vascotube, Birkenfeld, Germany). The tubing was laser cut into a leaflet frame 600 with leaflet frame projections 260, deformable locking bar restraining elements 605 at the commissure post 610 comprising deformable locking bars 670 and locking clips 672. The leaflet frame 600 was shape set at an inner diameter of 23 mm. The leaflet frame 600 is illustrated in FIGS. 11A, 16A, 11B, and 11D.

The leaflet frame 600 was placed on the mandrel on top of the subcomponent 680 and aligned with the corresponding subcomponent apertures 608. The subcomponent 680 was attached to the leaflet frame 600 by pushing the subcomponent apertures 608 in the subcomponent 680 over the leaflet frame projections 260. The first fold-over portions 683 and second fold-over portions 682 were folded over respective frame elements and placed against the leaflet frame outer surface 204 with the skirt 685 placed against the leaflet frame inner surface 202, as shown in FIG. 16B. The third fold-over portions 684 were folded about a fold line between the first row of sewing apertures 608a and the second row of sewing apertures 608b aligning the first row of sewing apertures 608a with the second row of sewing apertures 608b such that they may receive suture therethrough during a leaflet base attachment process.

An additional layer of the FEP/ePTFE construct, referred to as a covering 690, was applied to the leaflet frame outer surface 204 adjacent to the subcomponent 680, with the FEP side toward the mandrel, and bonded to the assembly on the mandrel utilizing a conventional autoclave vacuum bag technique. The autoclave temperature was ramped to 310° C., held for 20 minutes, and cooled to room temperature. A vacuum of about 0.8 bar (12 psi) and pressure of 6.8 bar (100 psi) were applied. This technique bonded the skirt 685 to the leaflet frame inner surface 202 and bonded the first fold-over portions 683, second fold-over portions 682, and third fold-over portions 684 to the leaflet frame outer surface 204 and the covering 690, as well as bonding the covering 690 to adjacent portions of the skirt 685. The sacrificial vacuum bag system was removed and discarded.

Figure 22:
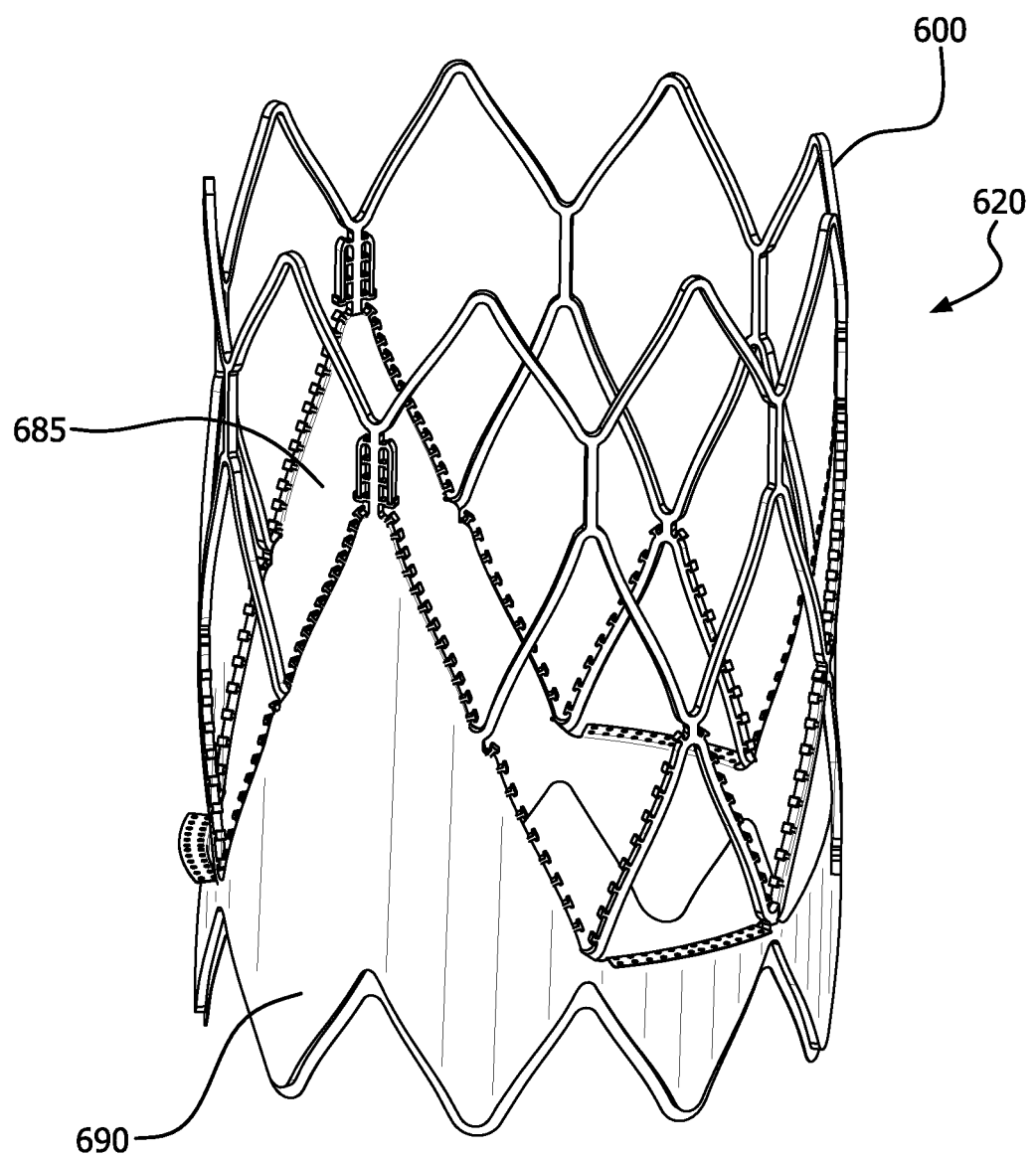
FIG. 22 is a perspective view of a covering over the leaflet frame assembly, in accordance with an embodiment.

The covering 690 was trimmed to the shape shown in FIG. 22.

Leaflet Construction

Leaflets were constructed in the same manner as described in Example 1 with two exceptions.

The multiple layers of ePTFE membrane imbibed with a fluoroelastomer were bonded together utilizing an autoclave. These multiple layers were wrapped onto a perforated hollow mandrel that had been wrapped with sacrificial release material, and subsequently bonded utilizing a conventional autoclave vacuum bag technique. The autoclave temperature was ramped to 280° C., held for about 30 minutes, then cooled to room temperature. A vacuum of about 0.8 bar (12 psi) and a pressure of about 6.8 bar (100 psi) were applied. The sacrificial vacuum bag system was removed and discarded. The resulting leaflet material and sacrificial release material were cut axially and removed from the mandrel. The sacrificial release material was then removed. The resulting leaflet material was spread flat.

The other exception was that only a single coupon was laser trimmed to form leaflets, thereby resulting in the absence of a reinforcement strip.

Leaflet Attachment

The leaflets 310 were coupled to the leaflet frame 600 to form the prosthetic valve 160, as shown in FIG. 19. The leaflet frame 600 was first immobilized by placing it on a holding mandrel. Then one of the leaflets 310 was placed over the leaflet frame 600 with the free edge 312 extending into the interior of the leaflet frame assembly 620. Each leaflet aperture 308 in the leaflet 310 was aligned with a corresponding leaflet frame projection 260. A blunted razor blade was used to press the leaflet attachment region 330 in the region between the leaflet apertures 308 so that each leaflet frame projection 260 extends through the corresponding leaflet aperture 308. This was repeated for all of the leaflet frame projections 260 and leaflet apertures 308 of the first leaflet 310, then repeated for the remaining two leaflets 310.

A leaflet base portion 616 of each leaflet 310 was sewn to the subcomponent 680 along the first row of sewing apertures 608a and the second row of sewing apertures 608b using ePTFE suture (CV6 Suture, W. L. Gore & Associates, Inc, Elkton, Md.). At each commissure post 610, the deformable locking bar 670 was folded down toward the locking clip 672 and clipped into the clip groove 673 in the locking clip 672 to restrain the leaflet 310, as illustrated in FIG. 17B. The deformable locking bar 670 was laser welded to the locking clip 672.

Figure 23:
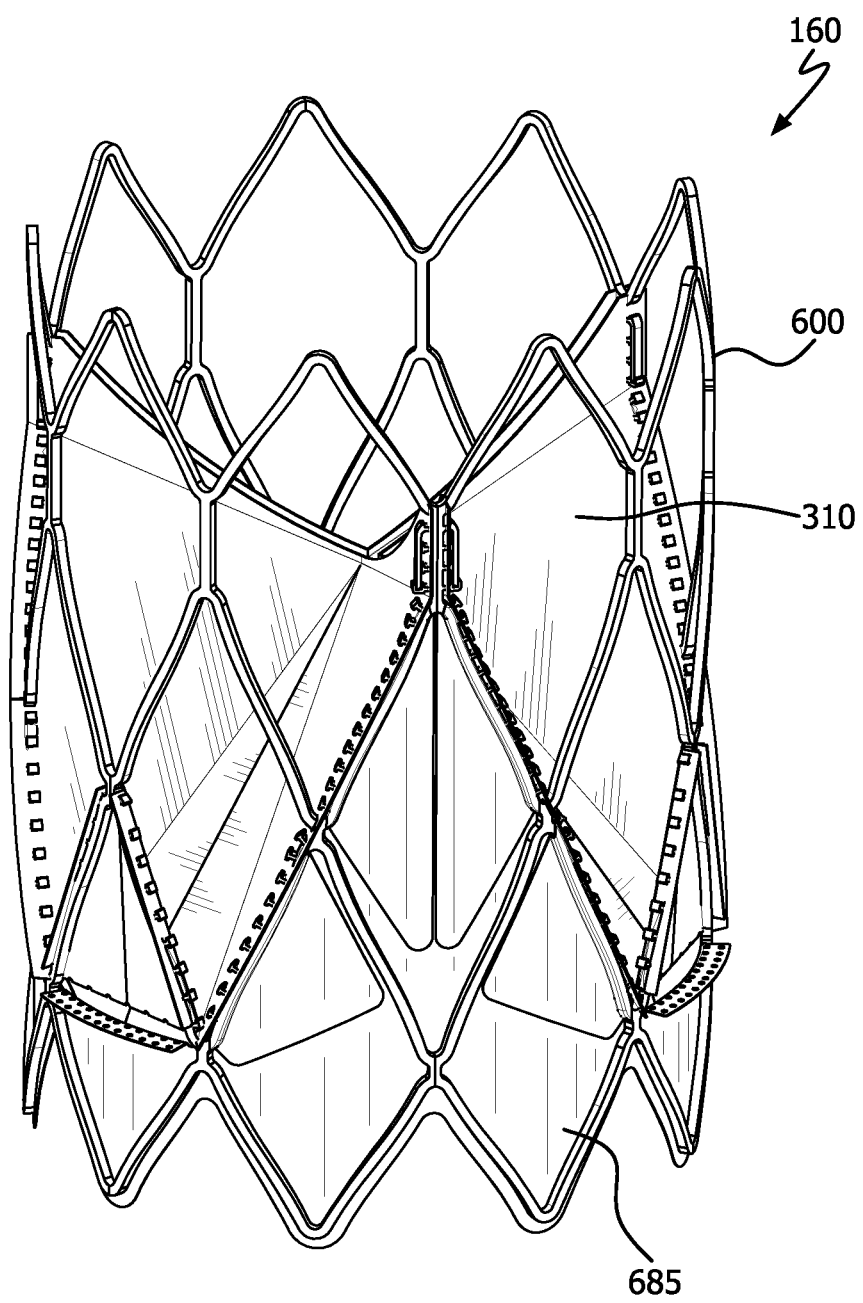
FIG. 23 is a perspective view of a transcatheter prosthetic valve, in accordance with an embodiment.

The resulting transcatheter prosthetic valve 160 is illustrated in FIG. 23.

Example 4: Transcatheter Balloon Expandable Prosthetic Valve

The leaflet frame 700 was prepared in the same manner as in Example 3, except that the frame was formed of 316L stainless steel tube with an inner diameter of 23 mm and the frame had an attachable locking bar restraining element including an attachable locking bar 770 and two locking clips 672 that are operable to couple with the attachable locking bar 770, as illustrated in FIGS. 12A and 12B. The attachable locking bar 770 includes a locking bar retention hook 771 at each end of the attachable locking bar 770 that is operable to couple with the respective locking clips 672, as shown in FIG. 12C.

The leaflets were prepared in the same manner as in Example 3. The leaflets were attached in the same manner as in Example 3, except that leaflets were restrained at the commissure post 710 by coupling the attachable locking bars 770 to respective locking clips 672, as illustrated in FIG. 12B.

The resulting transcatheter prosthetic valve 160 had the leaflets 310 attached to the leaflet frame 200 by the leaflet frame projections 260 extending through the leaflet apertures 308 and further retained on the leaflet frame projections 260 by the attachable locking bar restraining elements 705.

Methods: The above described physical characteristics of the materials used can be determined according to the following methods. However, it should be understood that any method or equipment determined suitable by one of ordinary skill in the art may be alternatively utilized.

Thickness: The thickness of films and membranes was measured by placing the membrane between the two plates of a Käfer FZ1000/30 thickness snap gauge Käfer Messuhrenfabrik GmbH, Villingen-Schwenningen, Germany. For thin membranes, multiple layers were measured at one time and the thickness of a single membrane was obtained by dividing the measured thickness by the number of layers measured. It should be appreciated that any suitable method for measuring thickness may be used.

Air Permeability Test: The air permeability test method assessed the porosity of a sample according to the general teachings of ISO 5636-5 by measuring the ability of air to flow through a material using a Gurley Densometer (Gurley Precision Instruments, Troy, N.Y.).

Density & Mass per Area: The density and mass per area are properties of membranes. An analytical balance (Mettler PM400 New Jersey, USA) was used to determine the mass of a sample of known area. Density was calculated with the following formula: $\rho=m/A*t$, in which: $\rho$=density, m=mass, A=area, and t=thickness. Mass per Area was calculated by dividing the mass by the sample area.

Tensile Strength of ePTFE Membranes: The Matrix Tensile Strength (MTS) of membranes was measured by first measuring the tensile strength of the membrane using an Instron 122 tensile test machine (Instron, Norwood, Mass.) equipped with flat grips and an 0.445 kN load cell. The gauge length was about 5.08 cm and the cross-head speed was about 50.8 cm/min. The sample dimensions were about 2.54 cm by about 15.24 cm. The matrix tensile strength, MTS, was calculated from the tensile strength and density according to the equation: MTS=(maximum load/cross-section area)*(bulk density of PTFE)/(density of the porous membrane), wherein the bulk density of the PTFE was taken to be about 2.2 g/cm$^3$.

Bubble Point Test: The IPA Bubble Point was measured by an IPA bubble point tester, Pressure Regulator Industrial Data Systems Model LG-APOK, Salt Lake City, Utah, USA, with a Ramp Rate of 1.38 KPa/s (0.2 psi/s), 3.14 cm$^2$ test area. Specifically, the bubble point is the minimum pressure required to force air through an IPA-saturated article. Raising the pressure slightly should produce steady streams of bubbles at many sites. Thus, the measurements are not biased by artifacts such as puncture holes in the material.

Numerous characteristics and advantages have been set forth in the preceding description, including various alternatives together with details of the structure and function of the devices and/or methods. The disclosure is intended as illustrative only and as such is not intended to be exhaustive. For example, embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet attachment region defines a plurality of leaflet apertures spaced apart from each other, each of the leaflet frame projections extending at least partially through a corresponding one of the plurality of leaflet apertures, wherein the one or more restraining elements are coupled to or unitary with the leaflet frame projections configured to impede decoupling of the leaflets from the leaflet frame, wherein the restraining element is integral to each of the leaflet frame projections, wherein the restraining element includes a projection head portion.

2. The prosthetic valve of claim 1, wherein a transverse dimension of the projection head portion is greater than a transverse dimension of the projection base portion.

3. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet attachment region defines a plurality of leaflet apertures spaced apart from each other, each of the leaflet frame projections extending at least partially through a corresponding one of the plurality of leaflet apertures, wherein the one or more restraining elements are coupled to or unitary with the leaflet frame projections configured to impede decoupling of the leaflets from the leaflet frame, wherein the restraining element is an attachable locking bar restraining element comprising an attachable locking bar including a bar-shaped element, the attachable locking bar having a length that spans a distance between at least two leaflet frame projections, wherein the attachable locking bar extends over the at least two leaflet frame projections and coupled thereto so as to impede decoupling of a respective leaflet from the respective leaflet frame projections.

4. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet attachment region defines a plurality of leaflet apertures spaced apart from each other, each of the leaflet frame projections extending at least partially through a corresponding one of the plurality of leaflet apertures, wherein the one or more restraining elements are coupled to or unitary with the leaflet frame projections configured to impede decoupling of the leaflets from the leaflet frame, wherein the restraining element is a cap that covers at least a portion of one or more leaflet frame projections suitable to impede decoupling of the leaflet attachment region from the one or more leaflet frame projections.

5. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein a distance between adjacent leaflet frame projections is less than 2 mm.

6. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein a distance between adjacent leaflet frame projections is at least 0.5 mm.

7. The prosthetic valve of claim 1, wherein the plurality of leaflet frame projections are unitary with the leaflet frame.

8. The prosthetic valve of claim 1, wherein the leaflet frame has a leaflet frame first edge, a leaflet frame second edge opposite the leaflet frame first edge, and optionally at least one leaflet frame internal edge, and wherein a leaflet retention surface is one or more of the leaflet frame second edge, the leaflet frame first edge, and the at least one leaflet frame internal edge.

9. The prosthetic valve of claim 8, wherein a leaflet retention surface is the leaflet frame second edge.

10. The prosthetic valve of claim 8, wherein the leaflet frame has a plurality of commissure posts and a set of leaflet window frame elements flanking each side of each commissure post, wherein each set of leaflet window frame elements and two of the plurality of commissure posts defines one of a plurality of leaflet windows.

11. The prosthetic valve of claim 10, wherein each commissure post has a post slot therethrough, wherein a portion of the leaflet attachment region that is adjacent to the leaflet free edge extends through the post slot adjacent thereto such that a portion of two leaflets extends through each post slot.

12. The prosthetic valve of claim 11, wherein the set of leaflet window frame elements includes two leaflet window sides and a leaflet window base therebetween.

13. The prosthetic valve of claim 12, wherein the leaflet window sides each define a side receiving slot therethrough and the leaflet window base defines a base receiving slot therethrough, wherein the leaflet window sides include a portion of the leaflet retention surface and wherein the leaflet window base includes a portion of the leaflet retention surface, and wherein a first portion of the leaflet attachment region extends through one of the two side receiving slots with respective leaflet frame projections extending through the leaflet attachment region, a second portion of the leaflet attachment region extends through the other of the two side receiving slots with respective leaflet frame projections extending through the leaflet attachment region, and a third portion of the leaflet attachment region extends through the base receiving slot with respective leaflet frame projections extending through the leaflet attachment region.

14. The prosthetic valve of claim 13, wherein the leaflet attachment region defines one or more notches.

15. The prosthetic valve of claim 13, wherein the leaflet retention surface is the leaflet frame second edge.

16. The prosthetic valve of claim 13, wherein the one or more of the leaflet window frame elements defines a leaflet frame opening therethrough that is adjacent to a respective receiving slot and is on the side opposite from the leaflet frame second edge, wherein the leaflet retention surfaces includes a portion of the leaflet frame internal edge defining each leaflet frame opening.

17. The prosthetic valve of claim 13, wherein the set of leaflet window frame elements together defines three sides of an isosceles trapezoid, wherein the leaflet window base defines a leaflet window base second edge that is substantially straight.

18. The prosthetic valve of claim 8, wherein the leaflet frame projections extend in a direction that is substantially normal to the leaflet retention surface.

19. The prosthetic valve of claim 8, wherein the restraining element is a deformable locking bar restraining element comprising:

a deformable locking bar including a bar base end and a bar free end opposite the bar base end, the deformable locking bar extending from the leaflet retention surface at the bar base end, the deformable locking bar having a length that spans a distance between the bar base end and at least one leaflet frame projection so as to impede decoupling of a respective leaflet from the respective leaflet frame projections.

20. The prosthetic valve of claim 19, wherein the locking bar is coupled with the at least one leaflet frame projection.

21. The prosthetic valve of claim 19, further comprising a locking clip coupled to the leaflet retention surface, wherein the locking clip is operable to couple with the bar free end, the deformable locking bar having a length that spans a distance between the bar base end and the locking clip, wherein at least one leaflet frame projection is located between the bar base end and the locking clip, wherein the deformable locking bar extends over the at least one leaflet frame projection so as to impede decoupling of a respective leaflet from the respective leaflet frame projections.

22. The prosthetic valve of claim 21, wherein the locking clip includes a clip groove operable to receive and retain the bar free end therein so as to couple the deformable locking bar to the locking clip.

23. The prosthetic valve of claim 19, wherein the leaflet frame has a plurality of commissure posts, wherein the plurality of commissure posts include a portion of the leaflet frame edges having the leaflet retention surface from which the deformable locking bar restraining element and a plurality of the leaflet frame projections extend.

24. The prosthetic valve of claim 8, wherein the restraining element is an attachable locking bar restraining element comprising:

an attachable locking bar including a bar-shaped element with a retention hook at each end; and a pair of locking clips spaced apart and coupled to the leaflet retention surface, wherein each of the locking clips is operable to couple with a respective retention hook of the locking bar, the attachable locking bar having a length that spans a distance between the pair of locking clips, wherein at least one leaflet frame projection is located between the pair of locking clips, wherein the attachable locking bar extends over the projection head portion of the at least one leaflet frame projection so as to impede decoupling of a respective leaflet from the respective leaflet frame projections.

25. The prosthetic valve of claim 24, wherein each of the retention hooks defines a C-shape operable to receive a portion of the locking clip therein, wherein each retention hook defines a retention flange operable to retain the portion of the locking clip within the retention hook.

26. The prosthetic valve of claim 25, wherein each of the locking clips includes a clip groove operable to receive and retain a portion of the bar-shaped element that is adjacent the retention hook therein so as to couple the attachable locking bar to the locking clip by capturing the locking clip between the bar-shaped element and the retention hook.

27. The prosthetic valve of claim 24, wherein the leaflet frame has a plurality of commissure posts, wherein the plurality of commissure posts include a portion of the leaflet frame edges having the leaflet retention surface from which the attachable locking bar restraining element and a plurality of the leaflet frame projections extend.

28. A prosthetic valve comprising:

a plurality of leaflets, each leaflet having a leaflet attachment region and a leaflet free edge;

a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and one or more restraining elements configured to impede decoupling of the leaflets from the leaflet frame, wherein the leaflet is formed of a leaflet material that is reinforced at the leaflet attachment region.

29. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet frame projections extend in a direction that is substantially parallel with a central longitudinal axis of the prosthetic valve.

30. The prosthetic valve of claim 29, further comprising a leaflet frame jacket coupled to the leaflet frame and having a lip that projects inward and is configured to impede the leaflets decoupling from the leaflet frame.

31. The prosthetic valve of claim 30, wherein the lip defines one or more recesses into which the leaflet frame projections extend and received therein.

32. The prosthetic valve of claim 1, wherein each leaflet is extendible substantially perpendicular from a leaflet frame inner surface such that each leaflet is biased towards a closed position.

33. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet frame projections comprise a shape memory material, wherein the leaflet frame projections define a first shape suitable to allow the advancement of the leaflet attachment region onto the leaflet frame projections and wherein the leaflet frame projections define a second shape that is suitable to impede decoupling of the leaflet attachment region from the leaflet frame projections.

34. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet frame projections comprise a plastically deformable material, wherein the leaflet frame projections define a first shape suitable to allow the advancement of the leaflet attachment region onto the leaflet frame projections and wherein the leaflet frame projections define a second shape by plastically deforming that is suitable to impede decoupling of the leaflet attachment region from the leaflet frame projections.

35. The prosthetic valve of claim 1, wherein the leaflet frame is operable to have one diameter suitable for use as a surgical prosthetic valve.

36. The prosthetic valve of claim 1, wherein the leaflet frame is operable to have a first diameter and a second diameter that is larger than the first diameter suitable for use as a transcatheter prosthetic valve.

37. A prosthetic valve comprising:
a plurality of leaflets, each leaflet having a leaflet attachment region and a leaflet free edge;
a leaflet frame defining an annular shape having one or more leaflet frame edges, the leaflet frame having a plurality of leaflet frame projections extending from at least one of the leaflet frame edges, each of the leaflet frame projections extending at least partially through the leaflet attachment region; and
one or more restraining elements configured to impede decoupling of the leaflets from the leaflet frame, wherein the leaflet frame is operable to have a first diameter and a second diameter that is larger than the first diameter suitable for use as a transcatheter prosthetic valve, wherein when the leaflet frame is at the first diameter opposing leaflet frame projections abut each other so as to prevent further compression of leaflet frame elements preventing crushing of the leaflet.

38. The prosthetic valve of claim 37, wherein when the leaflet frame is at the first diameter opposing leaflet frame projections are in a staggered configuration with respect to each other so as to prevent abutment therebetween so as to minimize the first diameter of the leaflet frame.

39. The prosthetic valve of claim 1, wherein the leaflet comprises a material that is synthetic or of animal origin.

40. The prosthetic valve of claim 1, wherein the leaflet comprises at least one fluoropolymer membrane layer.

* * * * *